D*US008946395B1*

US008946395B1

(12) United States Patent
Herigstad et al.

(10) Patent No.: US 8,946,395 B1
(45) Date of Patent: Feb. 3, 2015

(54) PURIFICATION OF PROTEINS USING HYDROPHOBIC INTERACTION CHROMATOGRAPHY

(71) Applicants: Matthew Omon Herigstad, Charlestown, MA (US); Linda E. Rich, Worcester, MA (US); Stephen Ming-teh Lu, Worcester, MA (US); Natarajan Ramasubramanyan, Westborough, MA (US)

(72) Inventors: Matthew Omon Herigstad, Charlestown, MA (US); Linda E. Rich, Worcester, MA (US); Stephen Ming-teh Lu, Worcester, MA (US); Natarajan Ramasubramanyan, Westborough, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/077,574

(22) Filed: Nov. 12, 2013

Related U.S. Application Data

(60) Provisional application No. 61/893,131, filed on Oct. 18, 2013.

(51) Int. Cl.
A23J 1/00 (2006.01)
C07K 1/00 (2006.01)
C07K 14/16 (2006.01)
C07K 17/00 (2006.01)
C07K 16/00 (2006.01)
C07K 1/16 (2006.01)
C07K 16/24 (2006.01)
C07K 1/20 (2006.01)

(52) U.S. Cl.
CPC ............. C07K 1/16 (2013.01); C07K 16/241 (2013.01); C07K 1/20 (2013.01)
USPC .......................................... 530/412; 530/415

(58) Field of Classification Search
None
See application file for complete search history.

(56) References Cited

U.S. PATENT DOCUMENTS

| 4,801,687 A | 1/1989 | Ngo |
| 4,877,608 A | 10/1989 | Lee et al. |
| 4,933,435 A | 6/1990 | Ngo |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,126,250 A | 6/1992 | McDonough et al. |
| 5,231,024 A | 7/1993 | Moeller et al. |
| 5,328,985 A | 7/1994 | Sano et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |

(Continued)

FOREIGN PATENT DOCUMENTS

| CN | 1299370 A | 6/2001 |
| CN | 1563090 A | 1/2005 |

(Continued)

OTHER PUBLICATIONS

Senezuk et al. "Hydrophobic interaction chromatography in dual salt system increases protein binding capacity" Biotechnology and Bioengineering, 103(5), 2009.*
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS.

(Continued)

Primary Examiner — Daniel E Kolker
Assistant Examiner — James Rogers
(74) Attorney, Agent, or Firm — McCarter & English, LLP; Maria Laccotripe Zacharakis; Maneesh Gulati

(57) ABSTRACT

The present invention is directed to methods for purifying a protein of interest, e.g., an antibody, from a sample comprising the protein of interest and at least one impurity, e.g., an aggregate, by employing a hydrophobic interaction chromatography (HIC) method that allows for binding of both the protein of interest and the at least one impurity under strong binding conditions. The present invention is based, at least in part, on the finding that both flow through and bind-elute techniques can be combined to achieve greater purification and recovery of a protein of interest, e.g., an antibody, under isocratic wash conditions and strong binding conditions.

92 Claims, 17 Drawing Sheets

(56) References Cited

U.S. PATENT DOCUMENTS

| | | | |
|---|---|---|---|
| 6,075,181 | A | 6/2000 | Kucherlapati et al. |
| 6,090,382 | A | 7/2000 | Salfeld et al. |
| 6,113,898 | A | 9/2000 | Anderson et al. |
| 6,150,584 | A | 11/2000 | Kucherlapati et al. |
| 6,171,586 | B1 | 1/2001 | Lam et al. |
| 6,255,458 | B1 | 7/2001 | Lonberg et al. |
| 6,258,562 | B1 | 7/2001 | Salfeld et al. |
| 6,270,766 | B1 | 8/2001 | Feldman et al. |
| 6,300,129 | B1 | 10/2001 | Lonberg et al. |
| 6,339,142 | B1 | 1/2002 | Basey et al. |
| 6,399,381 | B1 | 6/2002 | Blum et al. |
| 6,406,909 | B1 | 6/2002 | Shibuya et al. |
| 6,410,270 | B1 | 6/2002 | Strittmatter et al. |
| 6,413,746 | B1 | 7/2002 | Field |
| 6,436,397 | B1 | 8/2002 | Baker et al. |
| 6,448,380 | B2 | 9/2002 | Rathjen et al. |
| 6,451,983 | B2 | 9/2002 | Rathjen et al. |
| 6,489,447 | B1 | 12/2002 | Basey et al. |
| 6,498,237 | B2 | 12/2002 | Rathjen et al. |
| 6,509,015 | B1 | 1/2003 | Salfeld et al. |
| 6,528,286 | B1 | 3/2003 | Ryll |
| 6,593,458 | B1 | 7/2003 | Rathjen et al. |
| 6,673,986 | B1 | 1/2004 | Kucherlapati et al. |
| 6,680,181 | B2 | 1/2004 | Castan |
| 6,870,034 | B2 | 3/2005 | Breece et al. |
| 6,872,549 | B2 | 3/2005 | Van Ness et al. |
| 6,890,736 | B1 | 5/2005 | Reddy et al. |
| 6,900,056 | B2 | 5/2005 | Lee et al. |
| 6,914,128 | B1 | 7/2005 | Salfeld et al. |
| 6,924,124 | B1 | 8/2005 | Singh |
| 6,974,681 | B1 | 12/2005 | McGrew |
| 7,070,775 | B2 | 7/2006 | Le et al. |
| 7,084,260 | B1 | 8/2006 | Lonberg et al. |
| 7,122,641 | B2 | 10/2006 | Vedantham et al. |
| 7,189,820 | B2 | 3/2007 | Ruben |
| 7,192,584 | B2 | 3/2007 | Le et al. |
| 7,223,394 | B2 | 5/2007 | Salfeld et al. |
| 7,250,165 | B2 | 7/2007 | Heavner et al. |
| 7,276,239 | B2 | 10/2007 | Le et al. |
| 7,323,553 | B2 | 1/2008 | Fahrner et al. |
| 7,332,303 | B2 | 2/2008 | Schilling et al. |
| 7,390,660 | B2 | 6/2008 | Behrendt et al. |
| 7,429,491 | B2 | 9/2008 | Luan et al. |
| 7,504,485 | B2 | 3/2009 | Salfeld et al. |
| 7,521,206 | B2 | 4/2009 | Heavner et al. |
| 7,521,210 | B2 | 4/2009 | Knudsen |
| 7,541,031 | B2 | 6/2009 | Salfeld et al. |
| 7,588,761 | B2 | 9/2009 | Salfeld et al. |
| 7,645,609 | B2 | 1/2010 | Follstad |
| 7,714,112 | B2 | 5/2010 | Engstrand et al. |
| 7,750,129 | B2 | 7/2010 | Johansson et al. |
| 7,767,207 | B2 | 8/2010 | Ghayer et al. |
| 7,863,426 | B2 | 1/2011 | Wan et al. |
| 7,883,704 | B2 | 2/2011 | Salfeld et al. |
| 7,919,264 | B2 | 4/2011 | Maksymowych et al. |
| 7,947,471 | B2 | 5/2011 | Knudsen |
| 7,972,810 | B2 | 7/2011 | Crowell et al. |
| 8,067,182 | B2 | 11/2011 | Kelley et al. |
| 8,093,045 | B2 | 1/2012 | Pla et al. |
| 8,192,951 | B2 | 6/2012 | Wang et al. |
| 8,197,813 | B2 | 6/2012 | Salfeld et al. |
| 8,206,714 | B2 | 6/2012 | Salfeld et al. |
| 8,209,132 | B2 | 6/2012 | Bosques et al. |
| 8,231,876 | B2 | 7/2012 | Wan et al. |
| 8,361,797 | B2 | 1/2013 | Osborne et al. |
| 8,372,400 | B2 | 2/2013 | Salfeld et al. |
| 8,372,401 | B2 | 2/2013 | Salfeld et al. |
| 8,414,894 | B2 | 4/2013 | Salfeld et al. |
| 8,420,081 | B2 | 4/2013 | Fraunhofer et al. |
| 8,436,149 | B2 | 5/2013 | Borhani et al. |
| 8,663,945 | B2 | 3/2014 | Pla et al. |
| 8,753,633 | B2 | 6/2014 | Salfeld et al. |
| 2002/0045207 | A1 | 4/2002 | Krummen et al. |
| 2002/0132299 | A1 | 9/2002 | Field |
| 2002/0187526 | A1 | 12/2002 | Ruben et al. |
| 2003/0012786 | A1 | 1/2003 | Teoh et al. |
| 2003/0049725 | A1 | 3/2003 | Heavner et al. |
| 2003/0096414 | A1 | 5/2003 | Ciccarone et al. |
| 2003/0125247 | A1 | 7/2003 | Rosen et al. |
| 2003/0153735 | A1 | 8/2003 | Breece et al. |
| 2003/0157108 | A1 | 8/2003 | Presta |
| 2003/0161828 | A1 | 8/2003 | Abdelghany et al. |
| 2003/0166869 | A1 | 9/2003 | Vedantham et al. |
| 2003/0175884 | A1 | 9/2003 | Umana et al. |
| 2003/0178368 | A1 | 9/2003 | van Reis |
| 2003/0206898 | A1 | 11/2003 | Fischkoff et al. |
| 2003/0219438 | A1 | 11/2003 | Salfeld et al. |
| 2003/0229212 | A1 | 12/2003 | Fahrner et al. |
| 2003/0235585 | A1 | 12/2003 | Fischkoff et al. |
| 2004/0009172 | A1 | 1/2004 | Fischkoff et al. |
| 2004/0029229 | A1 | 2/2004 | Reeves et al. |
| 2004/0033228 | A1 | 2/2004 | Krause et al. |
| 2004/0038878 | A1 | 2/2004 | Tanikawa et al. |
| 2004/0101939 | A1 | 5/2004 | Santora et al. |
| 2004/0120952 | A1 | 6/2004 | Knight et al. |
| 2004/0126372 | A1 | 7/2004 | Banerjee et al. |
| 2004/0126373 | A1 | 7/2004 | Banerjee et al. |
| 2004/0131614 | A1 | 7/2004 | Banerjee et al. |
| 2004/0132140 | A1 | 7/2004 | Satoh et al. |
| 2004/0136989 | A1 | 7/2004 | Banerjee et al. |
| 2004/0136990 | A1 | 7/2004 | Banerjee et al. |
| 2004/0136991 | A1 | 7/2004 | Banerjee et al. |
| 2004/0151722 | A1 | 8/2004 | Banerjee et al. |
| 2004/0162414 | A1 | 8/2004 | Santora et al. |
| 2004/0166111 | A1 | 8/2004 | Kaymakcalan et al. |
| 2004/0171152 | A1 | 9/2004 | Price et al. |
| 2004/0191243 | A1 | 9/2004 | Chen et al. |
| 2004/0214289 | A1 | 10/2004 | deVries et al. |
| 2004/0219142 | A1 | 11/2004 | Banerjee et al. |
| 2005/0004354 | A1 | 1/2005 | Salfeld et al. |
| 2005/0100965 | A1 | 5/2005 | Ghayur et al. |
| 2005/0123541 | A1 | 6/2005 | Heavner et al. |
| 2005/0175611 | A1 | 8/2005 | Mahler et al. |
| 2005/0249735 | A1 | 11/2005 | Le et al. |
| 2005/0271654 | A1 | 12/2005 | Rinderknecht et al. |
| 2005/0272124 | A1 | 12/2005 | Chen et al. |
| 2006/0009385 | A1 | 1/2006 | Hoffman et al. |
| 2006/0018907 | A1 | 1/2006 | Le et al. |
| 2006/0024293 | A1 | 2/2006 | Salfeld et al. |
| 2006/0083741 | A1 | 4/2006 | Hoffman et al. |
| 2006/0149042 | A1 | 7/2006 | Konstantinov et al. |
| 2006/0153846 | A1 | 7/2006 | Krause et al. |
| 2006/0246073 | A1 | 11/2006 | Knight et al. |
| 2006/0252672 | A1 | 11/2006 | Betenbaugh et al. |
| 2006/0269479 | A1 | 11/2006 | Colton et al. |
| 2006/0287432 | A1 | 12/2006 | Christensen et al. |
| 2007/0003548 | A1 | 1/2007 | Heavner et al. |
| 2007/0004009 | A1 | 1/2007 | Dixit et al. |
| 2007/0041905 | A1 | 2/2007 | Hoffman et al. |
| 2007/0060741 | A1 | 3/2007 | Kelley et al. |
| 2007/0071747 | A1 | 3/2007 | Hoffman et al. |
| 2007/0081996 | A1 | 4/2007 | Hoffman et al. |
| 2007/0110743 | A1 | 5/2007 | Drapeau et al. |
| 2007/0111284 | A1 | 5/2007 | Ryll |
| 2007/0161084 | A1 | 7/2007 | Crowell et al. |
| 2007/0172475 | A1 | 7/2007 | Matheus et al. |
| 2007/0172897 | A1 | 7/2007 | Maksymowych et al. |
| 2007/0184045 | A1 | 8/2007 | Doctor et al. |
| 2007/0184529 | A1 | 8/2007 | Etcheverry et al. |
| 2007/0190057 | A1 | 8/2007 | Wu et al. |
| 2007/0196373 | A1 | 8/2007 | Le et al. |
| 2007/0202051 | A1 | 8/2007 | Schuschnig |
| 2007/0202104 | A1 | 8/2007 | Banerjee et al. |
| 2007/0269463 | A1 | 11/2007 | Donovan |
| 2007/0292442 | A1 | 12/2007 | Wan et al. |
| 2007/0298040 | A1 | 12/2007 | Le et al. |
| 2008/0025976 | A1 | 1/2008 | Le et al. |
| 2008/0112953 | A1 | 5/2008 | McAuley et al. |
| 2008/0118496 | A1 | 5/2008 | Medich et al. |
| 2008/0131374 | A1 | 6/2008 | Medich et al. |
| 2008/0160577 | A1 | 7/2008 | Dell'Orco et al. |
| 2008/0166348 | A1 | 7/2008 | Kupper et al. |
| 2008/0193466 | A1 | 8/2008 | Banerjee et al. |
| 2008/0219952 | A1 | 9/2008 | Fischer et al. |

(56) References Cited

U.S. PATENT DOCUMENTS

| | | |
|---|---|---|
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1* | 1/2011 | Wan et al. .................. 424/142.1 |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1* | 4/2011 | Hasslacher et al. ............ 435/174 |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0154270 A1 | 6/2014 | Wang et al. |
| 2014/0206038 A1 | 7/2014 | Pla et al. |

FOREIGN PATENT DOCUMENTS

| | | |
|---|---|---|
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |

(56) References Cited

FOREIGN PATENT DOCUMENTS

| | | |
|---|---|---|
| EP | 2574677 A1 | 4/2013 |
| GB | 2160530 A | 12/1985 |
| GB | 2279077 A | 12/1994 |
| JP | 7289288 A | 11/1995 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-9957246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-2004/058944 A2 | 7/2004 |
| WO | WO-2004058800 A2 | 7/2004 |
| WO | WO-2005042569 A1 | 5/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009023562 A2 | 2/2009 |
| WO | WO-2009/027041 A1 | 3/2009 |
| WO | WO-2009058769 A1 | 5/2009 |
| WO | WO-2009/073569 A2 | 6/2009 |
| WO | WO-2009135656 A1 | 11/2009 |
| WO | WO-2010036443 A1 | 4/2010 |
| WO | WO-2010043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013/011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |

OTHER PUBLICATIONS

"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS.

"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS.

"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.

"Plaintiffs' Memorandum in Support of Their Motion for Partial Summary Judgment", dated Aug. 1, 2013 and submitted by plaintiff in Civil Action No. 09-40089-FDS.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al. J. Am. Acad. Dermatol 2004;51 :660-2.

Altamirano, C., et al., "Strategies for fed batch cultivation of t-PA producing CHO cells: substitution of glucose and glutamine and rational design of culture medium", *J. Biotechn*. 110:171-179, 2004.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Avgerinos et al. (GAb '04 Abstracts—GE Healthcare Life Sciences, France Oct. 3-5, 2004, pp. 15-16 published 2005).

(56) References Cited

OTHER PUBLICATIONS

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Barbuto, J. et al. "Production of Neutralizing Antibodies to Tumor Necrosis Factor by Human Tumor-Infiltrating B Lymphocytes" *Proc. Am. Assoc. Cancer Res,.* 34:487, Abstr. 2904 (1993).

Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).

Biblia, T.A. et al., "In Pursuit of the Optimal Fed-Batch Process for Monoclonal Antibody Production", Biotechnol. Prog 11(1):1-13, Jan.-Feb. 1995.

Birch, JR. et al., "Antibody production", Adv. Drug Delivery Reviews 58:671-685, 2006.

Blaker, GJ, et al., "The Glucose, Insulin and Glutamine Requirements of Suspension Cultures of HeLa Cells in a Defined Culture Medium", J. Cell Sci. 9:529-537, 1971.

Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).

Bollati-Fogolin M., et al., "Temperature Reduction in Cultures of hGM-CSF-expressing CHO Cells: Effects on Productivity and Product Quantity", Biotechnol. Prog. 21:17-21, 2005.

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.

Boyle, P. et al. "A Novel Monoclonal Human IgM Autoantibody which Binds Recombinant Human and Mouse Tumor Necrosis Factor-α" *Cell. Immunol.*, 152:556-68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).

Brekke, O. et al., "Therapeutic Antibodies for Human Diseases at the Dawn of the Twenty-first Century," *Nature*, vol. 2:52-62 (2002).

Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).

Bruggemann et al., "Production of human antibody repertoires in transgenic mice" Cur. Op. Biotechnol. *;455-458 (1997).

Bruggemann, M., Neuberger, M.S., "Strategies for expressing human antibody repertoires in transgenic mice," *Immunol. Today* 17:391-397 (1996).

Cai B, et al. "C-Terminal Lysine Processing of Human; Immunoglobulin G2 Heavy Chain in Vivo" Biotechnol. Bioeng. 2011;108: 404-412.

Cambridge Antibody Technology, advertisement of phage display services, Science vol. 253, No. 5018 (1991).

Carter et al., "Humanization of an anti-p185HER2 antibody for human cancer therapy," *Proc. Nat. Acad. Sci*89:4285-4289 (1992).

Chang KH, et al., "N-Acetylcysteine Increases the Biosynthesis of Recombinant EPO in Apoptotic Chinese Hamster Ovary Cells", Free Radic Res. 30(2):85-91, 1999.

Charter, Edward A., "A New Process for the Separation and Purification of Egg Yolk; Antibodies," BASc., The University of British Columbia; A Thesis; Apr. 1993.

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chung et al., "Utilization of Lysozyme Charge Ladders to Examine the Effects of Protein Surface; Charge Distribution on Binding Affinity in Ion Exchange Systems," Lanqmuir 26(2):759-768 (2010).

Chung et al., "Cetuximab-Induced Anaphylaxis and IgE Specific for Galactose-α-1, 3-Galactose", *N. Engl. J. Med.*, 358:11, pp. 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).

Cox, J. et al. "A directory of human germ-line Vκ segments reveals a strong bias in their usage" *Eur. J. Immunol.*, 24(2):827-36 (1994).

Cromwell (GAB'04 Abstracts—GE Healthcare Life Sciences, Franc Oct. 3-5, 2004, pp. 17-18 published 2005).

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." *Biotechnology*, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

deZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.

Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).

Doring, E., "Identification and Characterization of a TNFa Antagonist Derived from a Monoclonal Antibody" (1994) *Mol. Immunol* .31(14): 1059-1067.

Elliot et al., "Repeated therapy with monoclonal antibody to tumour necrosis factor α (cA2) in patients with rheumatoid arthritis" (1994) *Lancet*, 344:1125-1127.

Elliot, "Treatment of rheumatoid arthritis with chimeric monoclonal antibodies to tumor necrosis factor α" (1993) *Arthritis & Rheumatism*, 36(12):1681-1690.

Emery, P. "Adalimumab therapy: Clinical findings and implications for integration into clinical guidelines for rheumatoid arthritis." *Drugs of Today*, 41(3): p. 155-153. (2005).

Erbitux (cetuximab) label, Revised Aug. 2013.

Ewert et al., "Biophysical Properties of Human Antibody Variable Domains," J. Mol. Biol. 324:531-; 553 (2003).

Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*.

Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y.

Exhibit dated Aug. 1, 2013 and cited by plaintiff in Civil Action No. 09-40089-FDS providing excerpts from the File History of U.S. Appl. No. 12/578,487.

(56) References Cited

OTHER PUBLICATIONS

Exhibit dated Aug. 1, 2013 and cited by defendant in Civil Action No. 09-40089-FDS providing the Jun. 24, 2009 trial transcript of the AM session in the matter of *Centocor, et al. v. Abbott Laboratories*, E.D. TX.

Exhibit dated Aug. 1, 2013 and cited by defendant in Civil Action No. 09-40089-FDS providing the Sep. 20, 2012 Day 8 trial transcript in the matter of *Abbott v. Centocor Ortho Biotech Inc.*, D. MA.

Exhibit dated Aug. 1, 2013 and cited by plaintiff in Civil Action No. 09-40089-FDS providing Declaration by Jochen Salfeld, dated Jan. 17, 2013.

FDA Package insert for Adalimumab, Sep. 26, 2003, pp. 1-18.

Feldmann, "Anti-TNF-alpha Therapy of Rheumatoid Arthritis: What Have We Learned?" (2001) *Annu. Rev. Immunol.*, 19:163-196.

Figini, "In Vitro assembly of Repertoires of Antibody Chains on the Surface of Phage by Renaturation" (1994) *J. Mol. Biol.*, 239:68-78.

Fishwild et al., "High-avidity human IgG kappa monoclonal antibodies from a novel strain of minilocus transgenic mice" (1996) *Nature Biotechnology*, 14:845-851.

Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.

Foote, J., "Antibody framework residues affecting the conformation of the hypervariable loops" (1992) *J. Mol .Biol.*, 224(2):487-499.

Freitag et al., "Displacement chromatography in biotechnological downstream processing," J. Chromatography, (1995) 691(1):101-112.

Gagnon et al., "A Systematic Approach to the Purification of Monoclonal Antibodies," *LC-GC* 11 (1):26-34 (1993).

Gatto, B. "Biologics targeted at TNF: design, production and challenges", Reumatismo 58(2):94-103, 2006.

Genbank Entry for CHO Cathepsin L., EGW13555, Aug. 25, 2011, pp. 1-2.

Ghaderi, et al., "Implications of the Presence of N-glycolylneuraminic acid in Recombinant Therapeutic Glycoproteins", *Nature Biotechnology*, 28(8):863-868 (2010).

Ghaderi, et al., "Production platforms for biotherapeutic glycoproteins. Occurrence, impact, and challenges of non-human sialylation", *Biotechnology and Genetic Engineering Reviews*, 28:147-176 (2012).

Gonzalez et al. "Purification of Lactic Acid from Fermentation Broths by Ion-Exchange Resins" Ind. Eng. Chem. Res. 45:3243 (2006).

Graf et al., "Ion exchange resins for the purification of monoclonal antibodies from animal cell culture" Bioseparation 4 (1) :7-20 (Feb. 1994).

Gram et al., "In vitro selection and affinity maturation of antibodies from a naive combinatorial immunoglobulin library" (1992) *PNAS*, 89:3576-3580.

Gramer et al., "Glycosidase Activities of the 293 and NS0 Cell Lines, and of an Antibody-Producing Hybridoma Cell Line", *Biotechnology and Bioengineering*, 43:423-428 (1994).

Green et al., "Antigen-specific human monoclonal antibodies from mice engineered with human Ig heavy and light chain YACs" (1994) *Nature Genetics*, 7:13-21.

Griffiths et al., "Isolation of high affinity human antibodies directly from large synthetic repertoires" (1994) *EMBO J.*, 13:3245-3260.

Griffiths, "Human anti-self antibodies with high specificity from phage display libraries" (1993) *The EMBO J.* 12(2):725-34.

Grunberg, J. et al., "High-Yield Production of Recombinant Antibody Fragments in HEK-293 Cells Using Sodium Butyrate", BioTechniques 34(5):968-972, May 2003.

Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4): 1154-1164, 2005.

Harding et al., "Class switching in human immunoglobulin transgenic mice" (1995) *Ann. NY Acad. Sci.*, 764:536-547.

Harlow and Lane, Antibodies A Laboratory Manual, Purification of Antibodies by using a; Deae-matrix (Batch), Storing and Purifying Antibodies; Chapter 8: 302-303 (1988).

Harris et al. "Processing of C-terminal lysine and argnine residues of proteins isolated from mammalian cell culture" Journal of Chromatography, (1995) 705; 129-123.

Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).

Hawkins, "Selection of Phage Antibodies by Binding Affinity Mimicking Affinity Maturation" (1992) *J. Mol. Biol.*, 226:889-896.

Heidemann, R. et al., "The use of peptones as medium additives for the production of a recombinant therapeutic protein in high density perfusion cultures of mammalian cells", Cytotechnology 32:157-167, 2000.

Helms et al., "Destabilizing loop swaps in the CDRs of an immunoglobulin VL domain," Protein; Science 4:2073-2081 (1995).

Hiatt et al., "Characterization and Applications of Antibodies Produced in Plants", *Intern. Rev. Immunol.*, 10:139-152 (1993).

Hiatt et al., "Production of Antibodies in Transgenic Plants", *Nature*, 342:76-78 (1989).

Hillgren, A. et al., "Protection mechanism of Tween 80 during freeze-thawing of a model protein LDH," *International Journal of Pharmaceutics*, vol. 237:57-69 (2002).

Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).

Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.

Holt, L. et al., "Domain antibodies: proteins for therapy," Trends in Biotechnology, vol. 21(11):484-490 (2003).

Hoogenboom et al., "By-passing immunisation : Human antibodies from synthetic repertoires of germline VH gene segments rearranged in vitro" (1992) *J. Mol. Biol.*, 227:381-388.

Hoogenboom, "Converting rodent into human antibodies by guided selection" (1996) *Antibody Engineering*, Oxford University Press, pp. 169-185.

Horvath et al: "Characterization of a Monoclonal Antibody Cell Culture Production Process Using a Quality by; Design Approach", Molecular Biotechnology, vol. 45, No. 3, Jul. 1, 2010, pp. 203-206.

Huang et al. "Effects of anti-TNF monoclonal antibody infusion in patients with hairy cell leukaemia" (1992) *Br. J. Haematol.*, 81(2):231-234.

Hui et al., "Recovery and purification process development for monoclonal antibody production," MABS (2010) 2(5):480-499.

Humira (adalimumab) label, Revised Sep. 2013.

Huse, "Generation of a large combinatorial library of the immunoglobulin repertoire in phage lambda" (1989) *Science*, 246:1275-81.

International Preliminary Report on Patentability for Application No. PCT/US07/08359, dated Dec. 12, 2011.

International Preliminary Report on Patentability for Application No. PCT/US2011/060388, dated May 30, 2012.

International Search Report and Written Opinion for Application No. PCT/US2008/085066, dated May 12, 2009.

International Search Report and Written Opinion for Application No. PCT/US2010/033387, dated Aug. 7, 2012.

International Search Report and Written Opinion for Application No. PCT/US2013/031380, dated Feb. 5, 2014.

International Search Report and Written Opinion for Application No. PCT/US2013/041954, dated Dec. 17, 2013.

International Search Report and Written Opinion for Application No. PCT/US2013/041958, dated Dec. 17, 2013.

International Search Report and Written Opinion for Application No. PCT/US2013/065720, dated Dec. 16, 2013.

International Search Report and Written Opinion for Application No. PCT/US2013/065797, dated Nov. 26, 2013.

(56) References Cited

OTHER PUBLICATIONS

International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
Invitation to Pay Additional Fees for International Application No. PCT/US2013/031380, Dated Nov. 28, 2013.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGI: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. 1)144-145.
Kempeni, J, "Preliminary results of early clinical trials with the fully human anti-TNFα monoclonal antibody D2E7", Ann. Rheum. Dis., 1999, pp. 170-172, vol. 58, (Suppl. 1).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Lerner, "Antibodies without immunization" (1992) *Science*, 258:1313-1314.
Leusch, "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low, "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Luo et al., "Understanding of C-terminal lysine variants in antibody production using mammalian cells" Abstract of papers, ACS, Anaheim, CA, US, Mar. 2011.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*Proteins: Structure, Function and Genetics*, 25:130-133.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).

(56) References Cited

OTHER PUBLICATIONS

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh, D-K. et al., "Increased erythritol production in fed-batch cultures of *Torula* sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Perchiacca et al., "Aggregation-resistance domain antibodies engineered with charged mutations; near the edges of the complementarity-determining regions," Protein Engineering Design & Selection, 25:10 (591-601) 2012.
Pietersz et al., "In vitro and in vivo Antitumor Activity of a Chimeric anti-CD19 Antibody", *Cancer Immunol. Immunother.*, 41:53-60 (1995).
Potter et al., "Antibody Production in the Baculovirus Expression System", *Intern. Rev. Immunol.*, 10:103-112 (1993).
Poul et al., "Design of Cassette Baculovirus Vectors for the Production of Therapeutic Antibodies in Insect Cells", *Immunotechnology*, 1:189-196 (1995).
Queen, C., "A humanized antibody that binds to the interleukin 2 receptor" (1989) *Proc. Natl. Acad. Sci. USA*, 86(24):10029-10033.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International.*, 44-53 (2003).
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Rube et al. (Int. J. Radiation Oncology Biol. Phys., vol. 56, No. 5, pp. 1414-1425,2003).
Rudikoff et al., "Single amino acid substitution altering antigen-binding specificity" (1982) *Proc. Natl. Acad. Sci. USA*, 70:1979-1983.
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.
Schwieterman, "Immunosuppression in Combination with Monoclonal Antibodies" in Biologic Agents in Autoimmune Disease (Mar. 2-4, 1995).
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shih, "Effects of Anions on the Deamidation of Soy Protein". Journal of Food Science. 1991, 56: 452-454.
Shukla et al., "Host cell protein clearance during protein A chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.
Tan et al. (Biotechnol. Appl. Biochem. (1999) 30, 59-64).
Taylor et al.,"Human immunoglobulin transgenes undergo rearrangement, somatic mutation and class switching in mice that lack endogenous IgM" (1994) *Int. Immunol.*, 6:579-591.
Teichmann, S. Declaration dated Dec. 7, 2010 from opposition proceedings in EP 0929578.
The Kennedy Institute of Rheumatology, 1995 Annual Scientific Report, "Anti-TNF trials and studies of mechanisms of action".
*The MW Calculator available at the Sequence Manipulation Suite* (see http://bioinformatics.org/sms2/index.html), downloaded Feb. 25, 2014.
The pI Calculator available at the Sequence Manipulation Suite (see <http://bioinformatics.org/sms2/index.html>) downloaded Feb. 25, 2014, p. 1).
The Statement on a Nonproprietary Name Adopted by the USAN Council for Adalimumab, page 1, downloaded on May 19, 2011 from http://www.ama-assn.org/resources/doc/usan/adalimumab.doc.
Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.
Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.
Tomiya et al., "Comparing N-glycan processing in mammalian cell lines to native and engineered; lepidopteran insect cell lines," Glycoconjuqate Journal 21 :343-360 (2004).
Tomlinson, "The repertoire of human germline VH sequences reveals about fifty groups of VH segments with different hypervariable loops" (1992) *J. Mol. Biol.*, 227:776-98.
Tomlinson, "The structural repertoire of the human Vk domain" (1995) *The EMBO J.*, 14(18):4628-38.

(56) References Cited

OTHER PUBLICATIONS

Tracey, "Tumor necrosis factor: A pleiotropic cytokine and therapeutic target" (1994) *Annu. Rev. Med.*, 45:491-503.
Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:1601 2-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.
Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vaughan, "Human antibodies by design" (1998) *Nature Biotechnology*, 16:535-539.
Wagner et al., "Antibodies generated from human immunoglobulin miniloci in transgenic mice" (1994) *Nucl. Acids Res*. 22:1389-1393.
Wagner et al., "The diversity of antigen-specific monoclonal antibodies from transgenic mice bearing human immunoglobulin gene miniloci" (1994) *Eur. J. Immunol.*, 24:2672-2681.
Ward, "Binding activities of a repertoire of single immunoglobulin variable domains secreted from *Escherichia coli*" (1989) *Nature*, 341:544-546.
Wedemayer et al., "Structural insights into the evolution of an antibody combining site" (1997) *Science*, 276:1665-1669.
Wiendl et al. (BioDrugs. 2002;16(3):183-200).
Williams et al., "Kinetic analysis by stopped-flow radiationless energy transfer studies: effect of anions on the activity of carboxypeptidase A". Biochemistry. 1986, 25, 94-100.
Winter, "Humanized antibodies" (1993) *Immunol. Today*, 14(6):243-246.
Winter, "Making antibodies by phage display technology" (1994) *Annu. Rev. Immunol.*, 12:433-455.
Wurm, FM, "Production of recombinant protein therapeutics in cultivated mammalian cells", Nature Biotechnology 22(11):1393-1398, 2004.
Yigzaw et al., "Exploitation of the adsorptive properties of depth filters for host cell protein removal during monoclonal antibody purification," Biotechnology Progress, (2006) 22(1):288-296.
Yumioka et al., "Screening of effective column rinse solvent for Protein—A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) *FASEB J.*, 10:1227-1232.
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Gramer M.J. et al: "Modulation of Antibody Galactosylation Through Feeding of Uridine, Manganese Chloride, and Galactose",Biotechnology and Bioengineering, Wiley & Sons, Hoboken, NJ, US, vol. 108, No. 7, Jul. 1, 2011, pp. 1591-1602.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Pink, T. et al.: "Regulation of S-layer protein synthesis of *Bacillus stearothermophilus* PV72 through variation of continuous cultivation conditions", Journal of Biotechnology, Elsevier Science Publishers, Amsterdam, NL, vol. 50, No. 2, Oct. 1, 1996, pp. 189-200.
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.
Wong, N.S.C. et al: "An investigation of intracellular glycosylation activities in CHO cells: Effects of nucleotide sugar precursor feeding", Biotechnology and Bioengineering, vol. 107, No. 2, Oct. 1, 2010, pp. 321-336.
Abbott Laboratories Press Release, "Abbott Laboratories Receives FDA Approval Earlier Than Expected for Humira (adalimumab) for the Treatment of Rheumatoid Arthritis," Dec. 31, 2002, pp. 1-4.
Averginos, Gab '04 Abstracts—GE Healthcare Life Sciences, "Humira manufacturing: challenges and the path taken", France, Oct. 3-5, 2004, published 2005, pp. 14-16.
Barnes et al., "Stability of Protein Production from Recombinant Mammalian Cells," Biotechnology and Bioengineering, 81:6, Mar. 20, 2003, pp. 631-639.
Byun, et al. Archives of Biochemistry and Biophysics, "Transport of anti-IL-6 binding fragments into cartilage and the effects of injury," 532 (2013), pp. 15-22.
Du et al., "Chromatographic analysis of the acidic and basic species of recombinant monoclonal antibodies" *mAbs*, Sep.-Oct. 2012; 4(5):578-85.
Feng et al., "Cell Culture Processes for Monoclonal Antibody Production," mAbs, 2:5, 466-477, Sep./Oct. 2010.
Folk et al., "Carboxypeptidase B, Purification and Characterization of the Porcine Enzyme," J. Biological Chem, 1960, 235:2272-2277.
Humira (adalimumab) prescribing information, Dec. 20, 2002, pp. 1-16.
ICH Topic Q6B "Specifications:Test Procedures and Acceptance Criteria for Biotechnological/Biological Products," Sep. 1999, pp. 1-17.
International Search Report from PCT/US2014/024256 dated Jul. 30, 2014, pp. 1-15.
Sundaram et al., "An innovative approach for the characterization of the isoforms of a monoclonal antibody product," Mabs, 3(6):505-512, 2011.
Invitation to Pay Additional Fees for International Application No. PCT/US2014/026606, Dated Jul. 8, 2014, pp. 1-8.
Wolff et al., "The Kinetics of Carboxypeptidase B Activity," J. Biological Chem, 1962, 237:3094-3099.

(56) References Cited

OTHER PUBLICATIONS

Worthington Biochemical Corporation, porcine pancreas carboxypeptidase B, one page, Feb. 25, 2012.

Boswell et al. "Effects of Charge on Antibody Tissue Distribution and Pharmacokinetics" Bioconjugate Chem.(21) 2153-2163 (2010).

Clincke et al. "Effect of surfactant pluronic F-68 on CHO cell growth, metabolism, production and glycosylation of human recombinant INF-γ in mild operating conditions" Biotechnology Progress, 27(1): 181-190 (2011).

http://www.cygnustechnologies.com/product_detail/host-cell-protein-antibodies/anti-cho-h...CYGNUS Technologies, Anti-CHO HCP (Apr. 18, 2012).

Martinelle, K. et al., Cells and Culture, Proceedings of the 20th ESACT Meeting v4 819-822, Jun. 17-20, 2007.

Hossler P. et al. "Improvement of mammalian cell culture performance through surfactant enabled concentrated feed media" Biotechnology Progress, 29(4):1023-1033 (2013).

Schiestl et al. "Acceptable changes in quality attributes of glycosylated biopharmaceuticals" Nature Biotechnology, 29(4): 310-312 (2011).

Senczuk et al. "Hydrophobic interaction chromatography in dual salt system increases protein binding capacity" Biotechnology and Bioengineering, 103(5): 930-935 (2009).

\* cited by examiner

SEQUENCE LISTING

<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Leu Val Gln Pro Gly Arg
 1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

-continued

```
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
  1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
  1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
  1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
  1               5                  10                  15

Gly

<210> SEQ ID NO 7
<211> LENGTH: 11
<212> TYPE: PRT
```

<213> ORGANISM: Artificial Sequence
<220> FEATURE:
<223> OTHER INFORMATION: adalimumab light chain variable region CDR1

<400> SEQUENCE: 7

```
Arg Ala Ser Gln Gly Ile Arg Asn Tyr Leu Ala
 1               5                  10
```

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

```
Asp Tyr Ala Met His
 1               5
```

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9

```
gacatccaga tgacccagtc tccatcctcc ctgtctgcat ctgtagggga cagagtcacc     60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321
```

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10

```
gaggtgcagc tggtggagtc tgggggaggc ttggtacagc ccggcaggtc cctgagactc     60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

<210> SEQ ID NO 11
<211> LENGTH: 214
<212> TYPE: PRT
<213> ORGANISM: Artificial Sequence
<220> FEATURE:
<223> OTHER INFORMATION: adalimumab light chain

<400> SEQUENCE: 11

```
Asp Ile Gln Met Thr Gln Ser Pro Ser Ser Leu Ser Ala Ser Val Gly
```

```
               1               5              10              15
           Asp Arg Val Thr Ile Thr Cys Arg Ala Ser Gln Gly Ile Arg Asn Tyr
                          20              25              30
           Leu Ala Trp Tyr Gln Gln Lys Pro Gly Lys Ala Pro Lys Leu Leu Ile
                          35              40              45
           Tyr Ala Ala Ser Thr Leu Gln Ser Gly Val Pro Ser Arg Phe Ser Gly
                          50              55              60
           Ser Gly Ser Gly Thr Asp Phe Thr Leu Thr Ile Ser Ser Leu Gln Pro
           65              70              75              80
           Glu Asp Val Ala Thr Tyr Tyr Cys Gln Arg Tyr Asn Arg Ala Pro Tyr
                          85              90              95
           Thr Phe Gly Gln Gly Thr Lys Val Glu Ile Lys Arg Thr Val Ala Ala
                          100             105             110
           Pro Ser Val Phe Ile Phe Pro Pro Ser Asp Glu Gln Leu Lys Ser Gly
                          115             120             125
           Thr Ala Ser Val Val Cys Leu Leu Asn Asn Phe Tyr Pro Arg Glu Ala
                          130             135             140
           Lys Val Gln Trp Lys Val Asp Asn Ala Leu Gln Ser Gly Asn Ser Gln
           145             150             155             160
           Glu Ser Val Thr Glu Gln Asp Ser Lys Asp Ser Thr Tyr Ser Leu Ser
                          165             170             175
           Ser Thr Leu Thr Leu Ser Lys Ala Asp Tyr Glu Lys His Lys Val Tyr
                          180             185             190
           Ala Cys Glu Val Thr His Gln Gly Leu Ser Ser Pro Val Thr Lys Ser
                          195             200             205
           Phe Asn Arg Gly Glu Cys
                          210

<210> SEQ ID NO 12
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12

Glu Val Gln Leu Val Glu Ser Gly Gly Gly Leu Val Gln Pro Gly Arg
           1               5              10              15
           Ser Leu Arg Leu Ser Cys Ala Ala Ser Gly Phe Thr Phe Asp Asp Tyr
                          20              25              30
           Ala Met His Trp Val Arg Gln Ala Pro Gly Lys Gly Leu Glu Trp Val
                          35              40              45
           Ser Ala Ile Thr Trp Asn Ser Gly His Ile Asp Tyr Ala Asp Ser Val
                          50              55              60
           Glu Gly Arg Phe Thr Ile Ser Arg Asp Asn Ala Lys Asn Ser Leu Tyr
           65              70              75              80
           Leu Gln Met Asn Ser Leu Arg Ala Glu Asp Thr Ala Val Tyr Tyr Cys
                          85              90              95
           Ala Lys Val Ser Tyr Leu Ser Thr Ala Ser Ser Leu Asp Tyr Trp Gly
                          100             105             110
           Gln Gly Thr Leu Val Thr Val Ser Ser Ala Ser Thr Lys Gly Pro Ser
                          115             120             125
           Val Phe Pro Leu Ala Pro Ser Ser Lys Ser Thr Ser Gly Gly Thr Ala
                          130             135             140
           Ala Leu Gly Cys Leu Val Lys Asp Tyr Phe Pro Glu Pro Val Thr Val
```

```
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
                210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
    355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
    450
```

PURIFICATION OF PROTEINS USING HYDROPHOBIC INTERACTION CHROMATOGRAPHY

RELATED APPLICATIONS

This application is related and claims priority to U.S. provisional application Ser. No. 61/893,131 filed Oct. 18, 2013, the entire contents of which is hereby incorporated herein by reference.

FIELD OF INVENTION

The instant invention relates to the field of protein production and purification, and in particular to compositions and processes for reducing the levels of impurities, including process-related impurities (e.g., host cell proteins and media components) and/or product-related substances (e.g., product charge variants, aggregates, and fragments).

BACKGROUND OF THE INVENTION

Hydrophobic interaction chromatography (HIC) is a purification technique that exploits the interaction of HIC media with hydrophobic regions present on a protein of interest, such as an antibody, and/or those present on an impurity to separate a protein of interest present in a sample mixture. HIC is often utilized in either a bind-elute mode, in which the protein of interest remains bound to HIC media until eluted during an elution phase, or a flow through mode, in which the protein of interest flows through the column while the impurity binds to the media.

Recently, a chromatographic method termed "weak partitioning mode" has been described for the purification of proteins (U.S. Pat. No. 8,067,182). According to U.S. Pat. No. 8,067,182, this method allows for the binding of both product and impurity and is defined by a intermediate partition coefficient (Kp) for the product. Compared to the flow-through mode, in which the Kp for the product is typically low (e.g., <0.1), thereby allowing the product to flow through the column while the impurity is bound, and the bind-elute mode, in which the Kp for the product is typically high (e.g., >20), thereby allowing the product to remain bound until eluted during an elution phase, in the weak portioning mode, the Kp for the product is in the range of 0.1-20.

Importantly, U.S. Pat. No. 8,067,182 teaches the criticality of this Kp range. Specifically, U.S. Pat. No. 8,067,182 teaches that Kp values greater than 20 result in a decreased load challenge at the point of contaminant breakthrough as the product begins to compete with the contaminant for binding sites on the media. In addition, U.S. Pat. No. 8,067,182 teaches that Kp values greater than 20 result in decreased product recovery in that the isocratic wash conditions are not effective at washing the bound product off the column in a reasonable number of wash volumes. Accordingly, U.S. Pat. No. 8,067,182, stresses the criticality of a Kp range to achieve desired purification (see columns 9 and 10).

When applied to HIC, the weak partitioning mode described in U.S. Pat. No. 8,067,182 requires an even more narrow Kp range. As set forth in Example 4, weak partitioning for HIC required a Kp less than 10. Patentees report that HIC performance deteriorates with respect to both contaminant reduction and product recovery at stronger binding conditions.

SUMMARY OF THE INVENTION

The present invention is directed to methods for purifying a protein of interest, e.g., an antibody, from a sample including the protein of interest and at least one impurity, e.g., an aggregate, by employing a novel hydrophobic interaction chromatography (HIC) method. The present invention is based, at least in part, on the finding that both flow through and bind-elute techniques can be combined to achieve greater purification and recovery of a protein of interest. Moreover, the present invention is predicated, at least in part, on the surprising finding that such methodology can be employed under isocratic wash conditions and at stronger binding conditions than previously appreciated, for example, at a Kp greater than 10, so as to achieve greater purification and recovery.

In one aspect, the present invention is directed to a method for producing a preparation including a protein of interest and having a reduced level of at least one impurity, said method comprising: (a) contacting a sample including the protein of interest and at least one impurity, to a hydrophobic interaction chromatography (HIC) media, in the presence of a load buffer such that (i) a portion of the protein of interest binds to the HIC media and (ii) a substantial portion of the at least one impurity binds to the HIC media; (b) collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein each of the flow through and wash fractions include the protein of interest and have a reduced level of the at least one impurity.

In various embodiments, the portion of the protein of interest binds to the HIC media at a Kp of greater than 10, 15, 20, 50, 60, 70, 80, 90, 100, 110, 120, 130, 140, 150, 160, 170, 180, 190, 200, 220, 250 or 300. For example, in various embodiments, the portion of the protein of interest binds to the HIC media at a Kp of greater than 10, the portion of the protein of interest binds to the HIC media at a Kp of greater than 20, or the portion of the protein of interest binds to the HIC media at a Kp of greater than 100.

In a particular embodiment, the protein of interest is adalimumab.

In one embodiment, a substantial portion of the impurity bound to the HIC media remains bound upon washing with the wash buffer. In one embodiment, the flow through and/or wash fractions are substantially free of the at least one impurity.

In one embodiment, the at least one impurity is an aggregate of the protein of interest, for example, selected from the group consisting of a multimer, a dimer, a trimer, a tetramer, an oligomer and other high molecular weight species. In a particular embodiment, the protein of interest is adalimumab and the at least one impurity is an aggregate of adalimumab. For example, the aggregate may be selected from the group consisting of multimer 1, multimer 2 and multimer 3.

In another embodiment, the impurity is a process-related impurity or a product-related substance. For example, the impurity may be a process-related impurity selected from the group consisting of a host cell protein, a host cell nucleic acid, a media component, and a chromatographic material. Alternatively, the impurity may be a product-related substance selected from the group consisting of a charge variant, an aggregate of the protein of interest, a fragment of the protein of interest and a modified protein.

In a particular embodiment the impurity is an acidic or basic variant, for example, of adalimumab. In a particular embodiment, the basic variant is a lysine variant species, for example, an antibody, or antigen-binding portion thereof, having heavy chains with either zero, one or two C-terminal lysines. In another embodiment, the impurity is an acidic species (AR), for example, selected from the group consisting of a charge variant, a structure variant, a fragmentation variant, a process-related impurity and a product-related impurity. In a particular embodiment, the acidic species is AR1 and the charge variant is a deamidation variant, a glycation variant, an afucosylation variant, a MGO variant and/or a citric acid variant. In another embodiment, the acidic species is AR1 and the structure variant is a glycosylation variant and/or an acetonation variant. In yet another embodiment, the acidic species is AR1 and the fragmentation variant is a Fab fragment variant, a C-terminal truncation variant or a variant missing a heavy chain variable domain. In yet a further embodiment, the acidic species is AR2 and the charge variant comprises a deamidation variant and/or glycation variant.

In a particular embodiment, the impurity is a fragment such as an Fc or a Fab fragment. In another embodiment, the impurity is a modified protein such as a deamidated protein or glycosylated protein.

In one embodiment, the protein of interest is an antibody or antigen-binding fragment thereof, a soluble protein, a membrane protein, a structural protein, a ribosomal protein, an enzyme, a zymogen, an antibody molecule, a cell surface receptor protein, a transcription regulatory protein, a translation regulatory protein, a chromatin protein, a hormone, a cell cycle regulatory protein, a G protein, a neuroactive peptide, an immunoregulatory protein, a blood component protein, an ion gate protein, a heat shock protein, an antibiotic resistance protein, a functional fragment of any of the preceding proteins, an epitope-containing fragment of any of the preceding proteins, and combinations thereof.

In a particular embodiment, the protein of interest is an antibody or antigen-binding fragment thereof such as a humanized antibody or antigen-binding portion thereof, a human antibody or antigen-binding portion thereof, a chimeric antibody or antigen-binding portion thereof, or a multivalent antibody. In one embodiment, the antibody, or antigen-binding fragment thereof, comprises a heavy chain constant region selected from the group consisting of IgG1, IgG2, IgG3, IgG4, IgM, IgA and IgE constant regions. In another embodiment, the antibody, or antigen-binding fragment thereof is selected from the group consisting of a Fab fragment, a F(ab')2 fragment, a single chain Fv fragment, an SMIP, an affibody, an avimer, a nanobody, and a single domain antibody.

In one embodiment, the methods of the invention further include repeating steps (a)-(d) at least 1, 2, 3, 4, 5, 6, 7, 8, 9, 10, 11, 12, 13, 14, 15 or 20 times using the flow through fraction, wash fraction, or combination thereof having a reduced level of the at least one impurity. In certain embodiments, the flow through fraction and the wash fraction are combined.

In one embodiment, the portion of the protein of interest that binds to the HIC media is at least about 20%, at least about 30%, at least about 40%, at least about 50%, at least about 60%, at least about 70%, at least about 80% or at least about 90% of the protein of interest in the sample. Alternatively or in combination, the substantial portion of the protein of interest released from the HIC media upon washing with the wash buffer is about at least 20%, at least about 30%, at least about 40%, at least about 50%, at least about 60%, at least about 70%, at least about 80%, at least about 90% or about 100% of the amount of protein of interest bound to the HIC media. Alternatively or in combination, the substantial portion of the at least one impurity that binds to the HIC media is at least about 50%, at least about 55%, at least about 60%, at least about 65%, at least about 70%, at least about 75%, at least about 80%, at least about 85%, at least about 90%, at least about 95% or about 100% of the at least one impurity in the sample.

In certain embodiments, the accumulative yield of the protein of interest in the flow through fraction and/or wash fraction is at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%. Alternatively or in combination, the accumulative yield of the protein of interest in any one flow through fraction and/or wash fraction is at least about 4%, at least about 10%, at least about 20%, at least about 30%, at least about 40%, at least about 50%, at least about 55%, at least about 60%, at least about 65%, at least about 70%, at least about 75%, at least about 80%, at least about 85, at least about 90%, at least about 95% or about 100%. Alternatively or in combination, the reduced level of the at least one impurity of the flow through fraction and/or wash fraction is at least about 50%, at least about 55%, at least about 60%, at least about 65%, at least about 70%, at least about 75%, at least about 80%, at least about 85%, at least about 90%, at least about 95% or about 100% of the at least one impurity in the sample.

In certain embodiments, the accumulative aggregate reduction of the at least one impurity in any one flow through fraction and/or wash fraction is at least about 0.1%, at least about 0.2%, at least about 0.5%, at least about 1.0%, at least about 2.0%, at least about 3.0%, at least about 4.0%, at least about 5.0%, at least about 10.0%, or at least about 20.0%. Alternatively or in combination, the accumulative aggregate reduction of the at least one impurity in the flow through fraction and/or wash fraction is at least about 0.1%, at least about 0.2%, at least about 0.5%, at least about 1.0%, at least about 2.0%, at least about 3.0%, at least about 4.0%, at least about 5.0%, at least about 10.0%, or at least about 20.0%.

In certain embodiments, the at least one impurity binds to the HIC media at a Kp of greater than 250, greater than 300, greater than 400, greater than 500, greater than 600, greater than 700, greater than 800, greater than 900, or greater than 1000. In certain embodiments, the protein of interest and the at least one impurity have a Kp ratio less than 1:10, 1:9, 1:8, 1:7, 1:6, 1:5, 1:4, 1:3 or 1:2.

In certain embodiments, the $K_d$ for the binding of the protein of interest to the HIC media is at least about 0.2, at least about 0.3, at least about 0.4, at least about 0.5, or at least about 0.6. Alternatively or in combination, the $K_d$ for the binding of the at least one impurity to the HIC media is less than or equal to about 0.001, about 0.005, about 0.01, about 0.02, about 0.05, about 0.1, about 0.15 or about 0.2. In particular embodiments, the $K_d$ for the binding of the protein of interest to the HIC media is less than 50, 45, 40, 35, 30, 25, 20, 15, 10 or 5 times the $K_d$ for the binding of the at least one impurity to the HIC media.

In certain embodiments, the protein of interest has a Qmax of at least about 20, at least about 30, at least about 40, at least about 50, at least about 60 or at least about 100. In certain embodiments, the at least one impurity has a Qmax of at least about 2, at least about 5, at least about 10, at least about 20, at least about 30 or at least about 40.

In certain embodiments, the HIC media comprises at least one hydrophobic ligand. For example, the HIC media may be selected from the group consisting of alkyl-, aryl-ligands, and combinations thereof. For example, the HIC media may be selected from the group consisting of butyl, hexyl, phenyl, octyl, or polypropylene glycol ligands. In a particular embodiment, the HIC media is selected from the group consisting of CaptoPhenyl, Phenyl Sepharose™ 6 Fast Flow with low or high substitution, Phenyl Sepharose™ High Performance, Octyl Sepharose™ High Performance, Fractogel™ EMD Propyl, Fractogel™ EMD Phenyl, Macro-Prep™ Methyl, Macro-Prep™ t-Butyl, WP HI-Propyl (C3)™, Toyopearl™ ether, Toyopearl™ phenyl, Toyopearl™ butyl, ToyoScreen PPG, ToyoScreen Phenyl, ToyoScreen Butyl, ToyoScreen Hexyl, HiScreen Butyl FF, HiScreen Octyl FF, and Tosoh Hexyl. In one embodiment, the HIC media is a column.

In various embodiments, the load buffer and/or wash buffer comprise a salt selected from the group consisting of ammonium sulfate, sodium sulfate, sodium chloride, ammonium chloride, sodium bromide or a combination thereof. In a particular embodiment, the load buffer and the wash buffer include a sulfate salt, a citrate salt, or a combination thereof. For example, the sulfate salt may be ammonium sulfate or sodium sulfate. In certain embodiments, the citrate salt is sodium citrate. In various embodiments, the load buffer and/or the wash buffer comprise a cation selected from the group consisting of $Ba^{2+}$, $Ca^{2+}$, $Mg^{2+}$, $Li^+$, $Cs^+$, $Na^+$, $K^+$, $Rb^+$, and $NH_4^+$, and/or an anion selected from the group consisting of $PO_4^{3-}$, $SO_4^{2-}$, $CH_3CO_3^-$, $Cl^-$, $Br^-$, $NO_3^-$, $ClO_4^-$, $I^-$, and $SCN^-$ or a combination thereof.

In one embodiment, the salt has a concentration of between about 50 mM and 2000 mM. In a particular embodiment, the load buffer and the wash buffer have a pH between about 4.0 and 8.5 or between about 5.0 and 7.0. In certain embodiments, the load buffer and the wash buffer have a pH of about 4.0, about 4.5, about 5.0, about 5.5, about 6, about 6.5, about 7.0, about 7.5, about 8.0, or about 8.5.

In one embodiment, the load buffer and the wash buffer are the same. In one embodiment, the load buffer and the wash buffer are substantially the same. For example, the salt concentration and/or the pH of the wash buffer may be within about 20%, 15%, 10% or 5% of the salt concentration, and/or pH of the loading buffer.

In certain embodiments, about 100 g to about 800 g of the sample are contacted per one liter of HIC media. Alternatively or in combination, about 0.2 g to about 120 g of the at least one impurity is contacted per one liter of HIC media. In certain embodiments, the sample has a protein concentration of about 2 mg/ml to about 50 mg/ml. In certain embodiments, the sample has a protein of interest concentration of about 2 mg/ml to about 50 mg/ml. Alternatively or in combination, the concentration of the at least one impurity in the sample is about 0.01 to about 5.0 mg/ml.

In various embodiments, the level of the at least one impurity is reduced by at least 60%, at least 70%, at least 80%, at least 90%, or at least 95% of the at least one impurity in the sample.

In one embodiment, the at least one impurity is a host cell protein. For example, the host cell protein may be reduced by at least 0.25, at least 0.5, at least 0.75, at least 1.0, at least 1.25 or at least 1.5 log reduction fraction.

In one embodiment, the HIC media has a dynamic binding capacity of at least about 2 g, at least about 5 g, at least about 10 g, at least about 20 g, at least about 30 g, at least about 40 g, at least about 50 g, at least about 60 g, at least about 70 g, at least about 90 g, or at least about 100 g of sample per one liter of media.

In one embodiment, a precursor sample including the protein of interest has been subjected to affinity chromatography to generate the sample. Alternatively or in combination, the preparation including a protein of interest and having a reduced level of one impurity is subjected to affinity chromatography. In such embodiments, affinity chromatography may be performed using affinity chromatographic media selected from the group consisting of Protein A, G, A/G, L media, and MabSuRe Protein A media.

In one embodiment, a precursor sample including the protein of interest has been subjected to ion exchange chromatography to generate the sample. Alternatively or in combination, the preparation including a protein of interest and having a reduced level of one impurity is subjected to ion exchange chromatography. In such embodiments, ion exchange chromatography may be performed using ion exchange chromatography media selected from the group consisting of (i) a cation exchange media, for example, comprising carboxymethyl (CM), sulfoethyl(SE), sulfopropyl (SP), phosphate(P) or sulfonate(S) ligands, and (ii) an anion exchange media, for example, comprising diethylaminoethyl (DEAE), quaternary aminoethyl (QAE) or quaternary amine (Q) group ligands.

In one embodiment, a precursor sample including the protein of interest has been subjected to mixed mode chromatography to generate the sample. Alternatively or in combination, the method involves subjecting the preparation including a protein of interest and having a reduced level of one impurity to mixed mode chromatography, for example, using CaptoAdhere resin.

In one embodiment, a precursor sample including the protein of interest has been subjected to a filtration step to generate the sample. Alternatively or in combination, the method involves subjecting the preparation including a protein of interest and having a reduced level of one impurity to a filtration step, for example, a depth filtration step, a nanofiltration step, an ultrafiltration step, and an absolute filtration step, or a combination thereof.

In one aspect, the present invention is directed to a pharmaceutical composition including the preparation produced by any of the foregoing methods.

In another aspect, the present invention is directed to a method for producing a preparation including adalimumab and having a reduced level of at least one aggregate, by (a) contacting a sample of adalimumab and at least one aggregate, to a HIC media, in the presence of a load buffer such that (i) a portion of the adalimumab in the sample binds to the HIC media and (ii) a substantial portion of the at least one aggregate binds to the HIC media; (b) collecting a flow through fraction of the adalimumab unbound to the HIC media; (c) washing the HIC media with a wash buffer that is substantially the same as the load buffer such that a substantial portion of the adalimumab bound to the HIC media is released from the media; and (d) collecting a wash fraction of the adalimumab released from the HIC media, wherein each of the flow through and wash fractions comprise adalimumab and have a reduced level of the at least one aggregate.

In one embodiment of the foregoing method, adalimumab binds to the HIC media at a Kp of greater than 10, 15, 20, 50, 60, 70, 80, 90, 100, 110, 120, 130, 140, 150, 160, 170, 180, 190, 200, 220, 250 or 300. For example, adalimumab binds to the HIC media at a Kp of greater than 10. Alternatively, adalimumab binds to the HIC media at a Kp of greater than 20. Alternatively, adalimumab binds to the HIC media at a Kp of greater than 90.

In a particular embodiment, the aggregate is multimer 1, multimer 2 or multimer 3.

In various embodiments, the sample includes between 200 g and 700 g protein per liter of HIC media. In certain embodiments, the HIC media is selected from the group consisting of GE CaptoPhenyl, Tosoh Hexyl, GE Butyl FF, Butyl, Hexyl, Phenyl, Octyl, GE Butyl FF, PPG. In certain embodiments, the load buffer and the wash buffer include ammonium sulfate, sodium sulfate, sodium citrate, or a combination thereof. Alternatively or in combination, the pH of the load buffer and the wash buffer is between 5 and 7. Alternatively or in combination, the salt concentration of the load buffer and the wash buffer is between about 150 mM and 1000 mM.

In another aspect, the present invention provides a pharmaceutical composition comprising a low-aggregate composition and a pharmaceutical acceptable carrier.

In one aspect, the present invention provides a pharmaceutical composition comprising a preparation of adalimumab produced by the foregoing methods and a pharmaceutically acceptable carrier. In another aspect, the present invention provides a pharmaceutical composition comprising a low-aggregate composition of adalimumab and a pharmaceutically acceptable carrier. For example, the composition may include less than 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1% of aggregates, e.g., MM1, MM2 and MM3. Alternatively, the composition may include less than 2%, 1.5%, 1.4%, 1.3%, 1.2%, 1.1%, 1%, 0.5%, 0.1% of aggregates, e.g., MM1, MM2 and MM3. Alternatively, the composition may include less than 1%, 0.5%, 0.1% of aggregates, e.g., MM1, MM2 and MM3.

BRIEF DESCRIPTIONS OF THE DRAWINGS

FIG. 1 depicts a size exclusion chromatography (SEC) chromatogram used to determine the molecular weight distribution of a sample of adalimumab. In combination with multi-angle light scattering (MALS) analysis (data not shown), the apparent molecular weight of each peak was determined and identified as a multimer or the reference standard as indicated. Multimer 1 (MM1), Multimer 2 (MM2) and Multimer 3 (MM3) were identified as depicted.

FIGS. 2A-2B depicts schematic chromatograms for two modes of chromatographic operation: bind-elute mode (FIG. 2A) and flow-through mode (FIG. 2B). In the bind-elute mode, there is strong binding of the protein of interest and the impurity. Elution conditions are chosen to selectively elutes the protein of interest. In the flow-through mode there is weak binding of the product and strong binding of the impurity.

FIG. 3 depicts selection of operating conditions appropriate for an antibody:media:buffer combination. A sample was loaded at 20 g/L and a linear gradient elution was performed over 20 CVs to identify the salt concentration at the monomer and aggregate peak. The salt concentration at or near the elution peak of the monomer is the concentration at which the monomer is eluted from the HIC media.

FIG. 4 depicts a process chromatogram for the HIC purification of Adalimumab, wherein a GE CaptoPhenyl column was equilibrated at 1.1 M AmSO$_4$ pH 7.0 (Tris/Acetate) for 10 CVs, Adalimumab was prepared at 1.1 M AmSO$_4$ and loaded to the column at 20 g-protein/L of media. The column was then washed with 10 CVs of the equilibration buffer and a linear gradient from 1.1 M to 0 M AmSO$_4$ pH 7.0 (Tris/Acetate) over 20 CVs was performed. See Example 1.

FIG. 5 depicts a process chromatogram for the HIC purification of Adalimumab, wherein a GE CaptoPhenyl column was equilibrated with 400 mM NaCit pH 5.6 for 10 CVs, Adalimumab was prepared at 400 mM NaCit pH 5.6 and then loaded to the column at 500 g-protein/L-media. Finally, the column was washed with 7 CVs of the equilibration buffer. See Example 1.

FIG. 6 depicts results of an experiment wherein a feed stream was serially diluted to cover a range of load concentrations from 4 to 15 mg/mL and loaded at 500 g/L to a CaptoPhenyl column in 400 mM NaCit pH 5.6. The results indicate the impact that the concentration of loaded protein can have on aggregate reduction. See Example 7.

FIG. 7 depicts the effect of aggregate load concentration on dynamic binding capacity and aggregate clearance. The column is conditioned and loaded at different sample load concentrations. The flow-through is fractionated to determine the product quality at different times during the load and breakthrough. Using protein mass and product quality for each of the collected fractions, the accumulative impurity (e.g., aggregate) can be calculated. The accumulative impurity of the preparation is reduced when the concentration of the aggregate in the load is reduced, even when the total load is unchanged (e.g., 500 g/L). See Example 13.

FIGS. 8A-8C depicts the effect of overall load protein concentration in the sample. The column is conditioned and loaded at different sample load concentrations. The flow through is fractionated to determine the product quality at different times during the load and breakthrough (FIG. 8A). Using protein mass and product quality for each of the collected factions, the accumulative aggregate impurity can be calculated. The accumulative aggregate impurity of the preparation is reduced when the protein concentration of the sample is reduced. The Equilibrium Binding Isotherms for both the monomer and aggregate show that for all of the loading conditions (FIG. 8B and FIG. 8C), the monomer was in the non-linear part of its binding isotherm (e.g., equilibrium binding capacity is independent of monomer concentration), and the aggregate was in or near the linear part of its binding isotherm (e.g., equilibrium binding capacity is dependent on aggregate concentration). Aggregate dynamic binding capacity=$f(C_o,t)$. See Example 13.

Figure 13A:
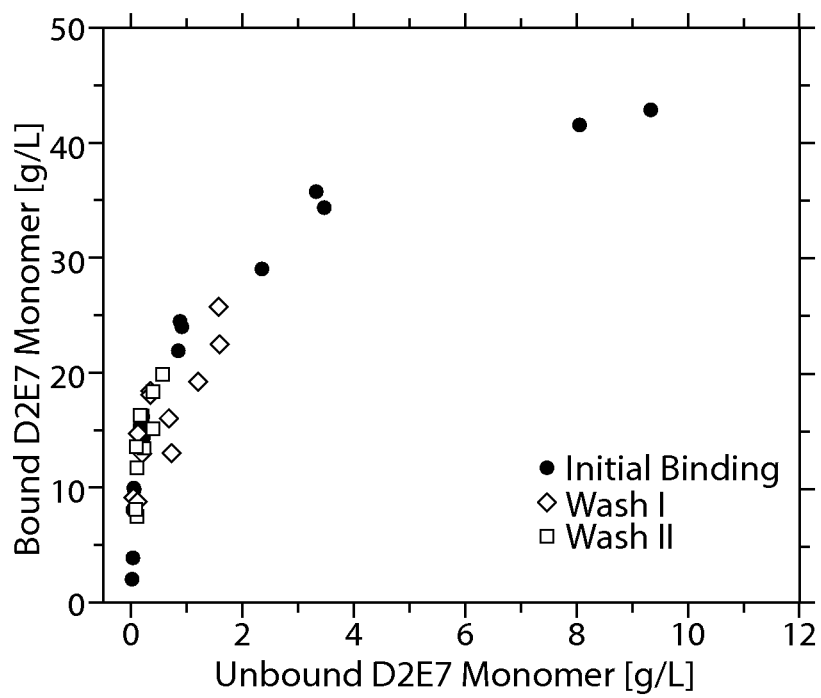
Figure 13B:
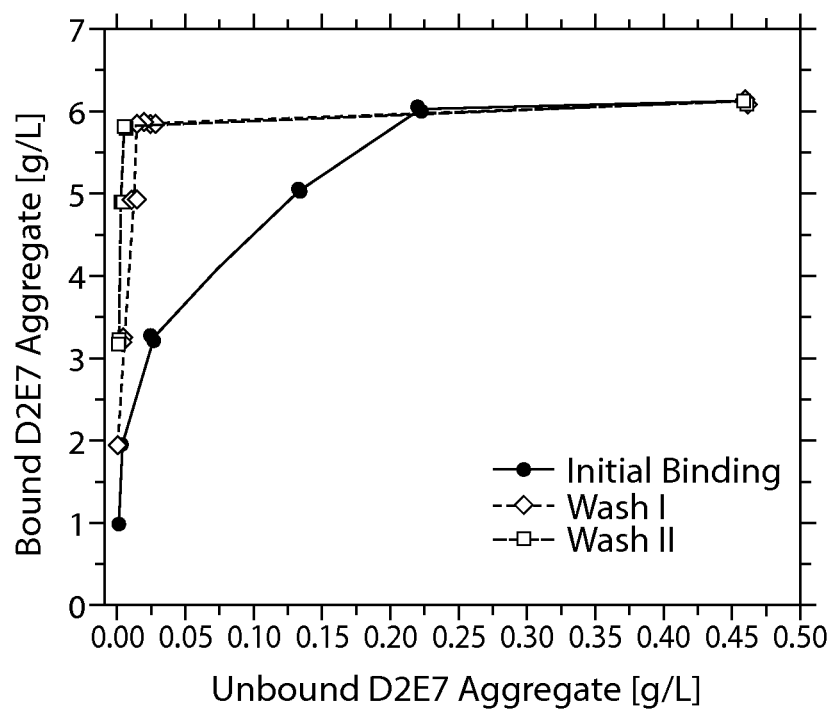

FIGS. 13A-13B depict the results of experiments wherein aliquots of resin are incubated with a load covering a range of protein concentrations at room temperature for 3 hours, after which the protein solution is then removed, and replaced with equilibration buffer (Wash simulation) and incubated at room temperature for 3 hours (repeated, Wash II). After each incubation, the concentration of the protein solution is measured and used to calculated the amount of protein ((FIG. 13A) monomer D2E7, (i.e., Adalimumab), and (FIG. 13B) aggregate D2E7) bound to the resin (g protein/L resin) and plotted against the concentration of the protein solution at the end of the incubation (e.g., equilibrium). See Example 11.

Figure 14A:
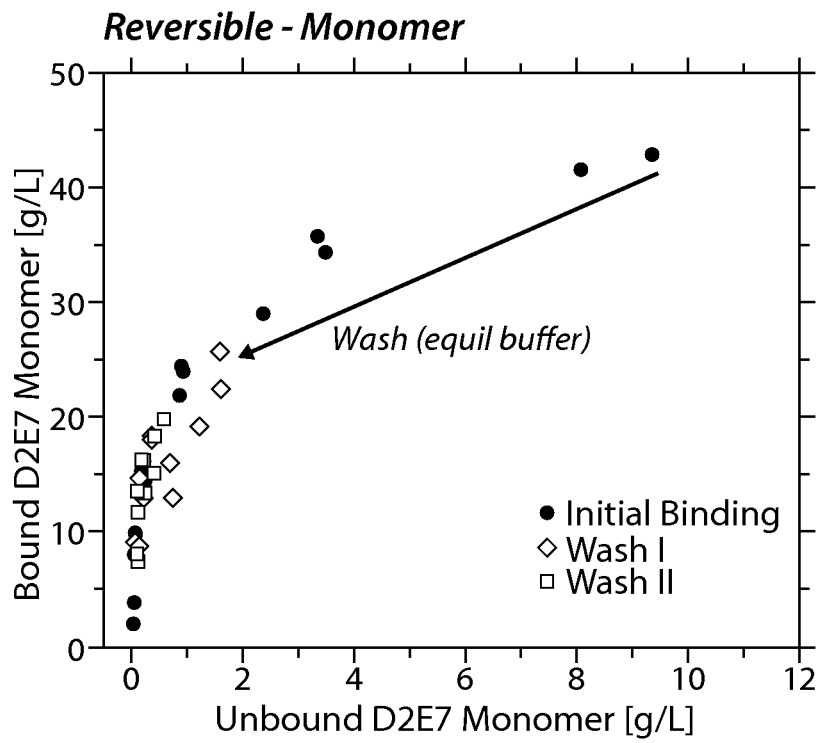
Figure 14B:
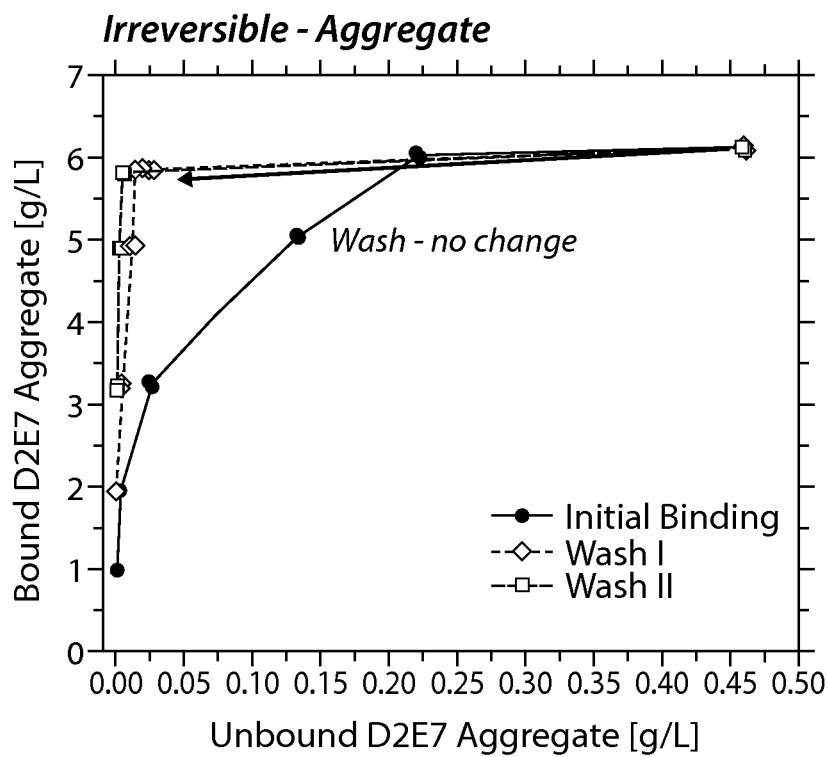

FIGS. 14A-14B depict the results outlined in FIGS. 13A-13B, highlighting the fact that at initial equilibrium a significant amount of monomer/aggregate is bound to the resin. However, after the protein solution is replaced with equilibration buffer (see arrow), the monomer desorbs from the resin and back into solution, whereas the aggregate remains bound. See Example 11.

Figure 15A:
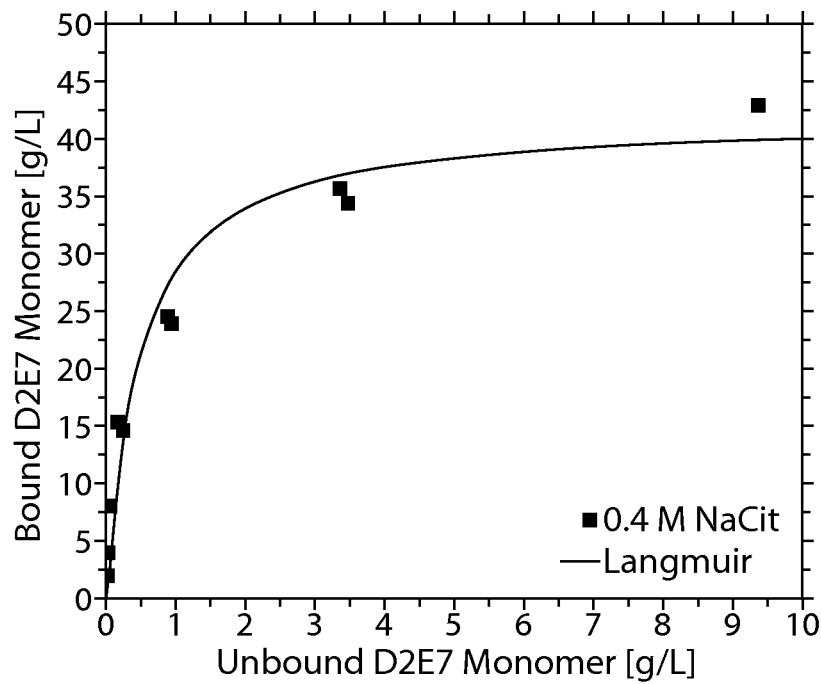
Figure 15B:
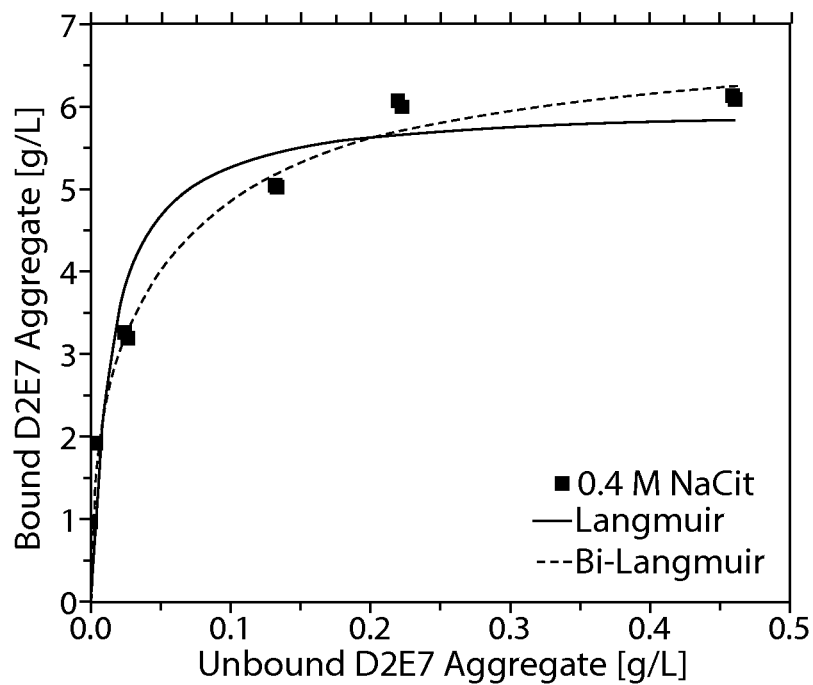

FIGS. 15A-15B depict a determination of the binding monomer and aggregate D2E7 (based on data provided in FIGS. 13A-13B) by fitting the experimental equilibrium binding data to the Langmuir Isotherm using the equation:

$q = (q_{max} \times C_{equil})/(K_d + C_{equil})$; where q=amount of protein bound to resin [=] g/L-resin; $q_{max}$=maximum amount of protein bound to resin [=] g/L-resin; $C_{equil}$=solution concentration of protein [=] g/L-soln; and $K_d$=equilibrium dissociation constant. See Example 11.

Figure 16:
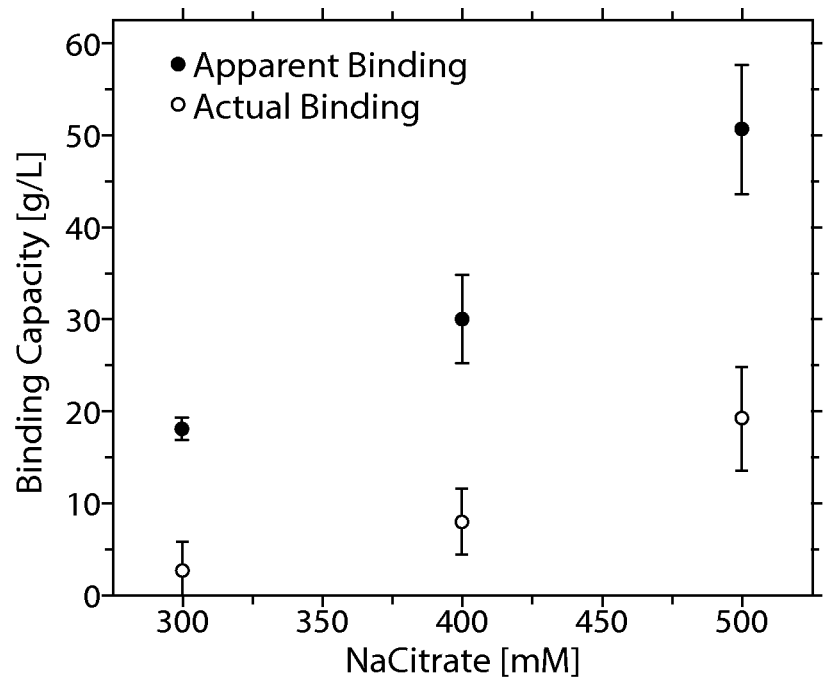

FIG. 16 depicts the comparison of Apparent and Actual bound protein under flow conditions (partial partitioning) as a function of salt concentration. Binding of the protein of interest is significant >10 g/L. The majority (>65%) of this monomer bound during the load desorbs during the isocratic wash (i.e., reversibly bound). The mass balance of the impurity demonstrates irreversible binding. See Example 12.

DETAILED DESCRIPTION OF THE INVENTION

The present invention is directed to methods for purifying a protein of interest, e.g., an antibody, from a sample comprising the protein of interest and at least one impurity, e.g., an aggregate, by employing a novel hydrophobic interaction chromatography (HIC) method. The present invention is based, at least in part, on the finding that both flow through and bind-elute techniques can be combined to achieve greater purification and recovery of a protein of interest, e.g., an antibody. Moreover, the present invention is predicated, at least in part, on the surprising finding that such methodology can be employed under isocratic wash conditions and at stronger binding conditions than previously appreciated, for example, at a Kp greater than 10 or at a Kp greater than 20, so as to achieve greater purification and recovery.

In one aspect, the present invention provides a method for producing a preparation including a protein of interest, e.g., an antibody such as adalimumab, and having a reduced level of at least one impurity, e.g., an aggregate, by (a) contacting a sample including the protein of interest and at least one impurity, to a hydrophobic interaction chromatography media, in the presence of a load buffer such that (i) a portion of the protein of interest binds to the hydrophobic interaction chromatography (HIC) media and (ii) a substantial portion of the at least one impurity binds to the HIC media; (b) collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein each of the flow through and wash fractions include the protein of interest and have a reduced level of the at least one impurity. In a particular embodiment, the portion of the protein of interest binds to the HIC media at a Kp of greater than 10. In another embodiment, the portion of the protein of interest binds to the HIC media at a Kp of greater than 20. In another embodiment, the portion of the protein of interest binds to the HIC media at a Kp of greater than 100.

In certain embodiments, the purification strategies of the present invention may include one or more chromatography and/or filtration steps to achieve a desired degree of purification prior to exposure of the sample comprising the protein of interest, e.g., an antibody such as adalimumab, to the HIC media. For example, in certain embodiments, such pre-HIC chromatography step(s) can include one or more steps of chromatography and/or filtration. In one embodiment the chromatography is ion exchange chromatography, mixed mode chromatography, and/or affinity chromatography. In another embodiment, the filtration step is depth filtration, nanofiltration, ultrafiltration and/or absolute filtration. In certain embodiments, the purification strategies of the present invention may include one or more additional chromatography and/or filtration steps after the HIC purification step. For example, in certain embodiments, such post-HIC chromatography step(s) can include one or more steps of chromatography and/or filtration. In one embodiment, the chromatography is ion exchange chromatography, mixed mode chromatography, and/or affinity chromatography. In another embodiment, the filtration step is depth filtration, nanofiltration, ultrafiltration and/or absolute filtration.

In addition, in certain embodiments, the present invention is directed toward pharmaceutical compositions comprising one or more proteins of interest purified by methods described herein. In a particular embodiment, the present invention is directed to a pharmaceutical composition comprising adalimumab and having a reduced level of aggregates.

Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms, for example, those characterized by "a" or "an", shall include pluralities, e.g., one or more impurities. In this application, the use of "or" means "and/or", unless stated otherwise. Furthermore, the use of the term "including," as well as other forms of the term, such as "includes" and "included", is not limiting. Also, terms such as "element" or "component" encompass both elements and components comprising one unit and elements and components that comprise more than one unit unless specifically stated otherwise.

As used herein, the term "sample", refers to a liquid composition including the protein of interest and one or more impurities. In a particular embodiment, the sample is a "clarified harvest", referring to a liquid material containing a protein of interest, for example, an antibody of interest such as adalimumab, that has been extracted from cell culture, for example, a fermentation bioreactor, after undergoing centrifugation to remove large solid particles and subsequent filtration to remove finer solid particles and impurities from the material.

In various embodiments, the sample may be partially purified. For example, the sample may have already been subjected to any of a variety of art recognized purification techniques, such as chromatography, e.g., ion exchange chromatography, mixed mode chromatography, and/or affinity chromatography, or filtration, e.g., depth filtration, nanofiltration, ultrafiltration and/or absolute filtration.

The term "precursor sample", as used herein refers to a liquid composition containing the protein of interest and, optionally, one or more impurities, either derived from the clarified harvest, or a partially purified intermediate sample that is subject to a purification or treatment step prior to being subjected to HIC. Impurities in a precursor sample may be derived from the production, purification or treatment of the protein of interest prior to subjecting the resulting sample to HIC.

The term "protein of interest", as used herein refers to a target protein present in a sample, purification of which is desired. In various embodiment, the protein of interest is an antibody or antigen-binding fragment thereof, a soluble protein, a membrane protein, a structural protein, a ribosomal protein, an enzyme, a zymogen, an antibody molecule, a cell surface receptor protein, a transcription regulatory protein, a translation regulatory protein, a chromatin protein, a hormone, a cell cycle regulatory protein, a G protein, a neuroactive peptide, an immunoregulatory protein, a blood component protein, an ion gate protein, a heat shock protein, an antibiotic resistance protein, a functional fragment of any of the preceding proteins, an epitope-containing fragment of any of the preceding proteins, and combinations thereof. In a particular embodiment, the protein of interest is a monomer.

In a particular embodiment, the protein of interest is an antibody, or an antigen binding portion thereof. The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody", as used herein, also includes alternative antibody and antibody-like structures, such as, but not limited to, dual variable domain antibodies (DVD-Ig).

The term "antigen-binding portion" of an antibody (or "antibody portion") includes fragments of an antibody that retain the ability to specifically bind to an antigen (e.g., hIL-12, hTNFα, or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody may be part of a larger immunoadhesion molecule, formed by covalent or non-covalent association of the antibody with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is Adalimumab (AbbVie).

As used herein, the term "adalimumab," also known by its trade name HUMIRA® (AbbVie) refers to a human IgG$_1$ antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The light chain variable region of adalimumab is provided herein as SEQ ID NO:1, and the heavy chain variable region of adalimumab is provided herein as SEQ ID NO:2. Adalimumab comprises a light chain variable region comprising a CDR1 of SEQ ID NO:7, a CDR2 of SEQ ID NO:5, and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. The nucleic acid sequence of the light chain variable region is set forth in SEQ ID NO:9. The nucleic acid sequence of the heavy chain variable region is set forth in SEQ ID NO:10. The full length amino acid sequence of the light chain is set forth as SEQ ID NO:11 and the full length amino acid sequence of the heavy chain is set forth as SEQ ID NO:12. Adalimumab is described in U.S. Pat. Nos. 6,090,382; 6,258,562; 6,509,015; 7,223,394; 7,541,031; 7,588,761; 7,863,426; 7,919,264; 8,197,813; 8,206,714; 8,216,583; 8,420,081; 8,092,998; 8,093,045; 8,187,836; 8,372,400; 8,034,906; 8,436,149; 8,231,876; 8,414,894; 8,372,401, the entire contents of each which are expressly incorporated herein by reference in their entireties. Adalimumab is also described in the "Highlights of Prescribing Information" for HUMIRA® (adalimumab) Injection (Revised January 2008) the contents of which are hereby incorporated herein by reference.

In one embodiment, adalimumab dissociates from human TNFα with a Kd of $1\times10^{-8}$ M or less and a K$_{off}$ rate constant of $1\times10^{-3}$ s$^{-1}$ or less, both determined by surface plasmon resonance, and neutralizes human TNFα cytotoxicity in a standard in vitro L929 assay with an IC50 of $1\times10^{-7}$ M or less. In another embodiment, adalimumab dissociates from human TNFα with a K$_{off}$ of $5\times10^{-4}$ s$^{-1}$ or less, or even more preferably, with a K$_{off}$ of $1\times10^{-4}$ s$^{-1}$ or less. In still another embodiment, adalimumab neutralizes human TNFα cytotoxicity in a standard in vitro L929 assay with an IC50 of $1\times10^{-8}$ M or less, an IC50 of $1\times10^{-9}$ M or less or an IC50 of $1\times10^{-10}$ M or less. The term "Koff", as used herein, is intended to refer to the off rate constant for dissociation of an antibody from the antibody/antigen complex.

The term "impurity", as used herein refers to any foreign or objectionable molecule, including a biological macromolecule such as a DNA, an RNA, or a protein other than the protein of interest being purified. Exemplary impurities include, for example, protein variants, such as aggregates, high molecular weight species, low molecular weight species and fragments, and deamidated species; host cell proteins; proteins that are part of an absorbent used for affinity chromatography (e.g. Protein A); endotoxins; and viruses.

The methods of the invention serve to generate a preparation comprising a protein of interest and having a reduced level of impurity. As used herein a "reduced level of impurity" refers to a composition comprising reduced levels of an impurity as compared to the levels of the impurity in the sample prior to purification by the methods of the present invention. In another embodiment, the methods of the invention generate a preparation comprising a protein of interest and having a reduced level of total impurity. As used herein a "reduced level of total impurity" refers to a composition comprising reduced levels of total impurity as compared to the levels of the impurity in the sample prior to purification by the methods of the present invention. In one embodiment, a preparation having a reduced level of total impurity is free of impurities or substantially free of impurities.

The present invention is further directed to low impurity compositions and methods of generating the same, for example, low impurity compositions of adalimumab. The term "low impurity composition," as used herein, refers to a composition comprising a protein of interest, wherein the composition contains less than about 15% total impurities. For example, a low impurity composition may contain about 10%, 9%, 8%, 7%, 6%, 5%, 4%, 3%, 2%, 1.5%, 1.4%, 1.3%, 1.2%, 1.1%, 1%, 0.5%, or less total impurities. In a particular embodiment, a low impurity composition comprises about 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less total impurities.

The term "non-low impurity composition," as used herein, refers to a composition comprising a protein of interest, which contains more than about 15% total impurity. For example, a non-low impurity composition may contain about 15%, 16%, 17%, 18%, 19%, 20%, 21%, 22%, 23%, 24%, 25%, or more total impurities.

In one embodiment, a low impurity composition has improved biological and functional properties, including increased efficacy in the treatment or prevention of a disorder in a subject, e.g., a disorder in which TNFα activity is detrimental, as compared to a non-low impurity composition. In one embodiment, the low impurity composition comprises an anti-TNFα antibody, or antigen-binding portion thereof, such as adalimumab or a fragment thereof. For example, in one embodiment, a low impurity composition comprising an antibody, or antigen-binding portion thereof, exhibits increased cartilage penetration, decreased bone erosion, and/or reduced cartilage destruction, as compared to a non-low impurity composition comprising the same antibody or antigen binding portion thereof, when administered to a subject suffering from a disorder in which TNFα activity is detrimental.

As used herein, the term "increased cartilage penetration" refers to increased penetration of cartilage in vivo by a low impurity composition as compared to a non-low impurity composition comprising the same antibody or antigen binding portion thereof.

As used herein, the term "reduced cartilage destruction" refers to measurable decrease in destruction of cartilage tissue in vivo by a low impurity composition as compared to a non-low impurity composition comprising the same antibody or antigen binding portion thereof. As used herein, the term "decreased bone erosion" refers to measurable decrease, in vivo, of the erosion of bone tissue by a low impurity composition as compared to a non-low aggregate composition comprising the same antibody or antigen binding portion thereof. For example, an in vivo model of a disease or disorder in which TNFα activity is detrimental, e.g., a mouse model of arthritis, can be used to measure cartilage penetration, bone erosion, and/or cartilage destruction by a composition comprising an anti-TNFα antibody or antigen binding portion thereof. One non-limiting example of an art-recognized mouse model of arthritis is the human TNF transgenic 197 mouse model of arthritis (TNF-Tg197) (see Keffer, J. et al., *EMBO J* (1991) 10:4025-4031 for further description of the TNF-Tg197 model of arthritis).

In another embodiment, a low impurity composition comprising an antibody, or antigen-binding portion thereof, exhibits increased protection against the development of arthritic scores and/or histopathology scores as compared to a non-low impurity composition when administered to an animal model of arthritis, e.g., the TNF-Tg197 model of arthritis. As used herein, "arthritic scores" refer to signs and symptoms of arthritis in an animal model of arthritis. As used herein, "histopathology scores" refer to radiologic damage involving cartilage and bone as well as local inflammation.

In another embodiment, a low impurity composition comprising an antibody, or antigen-binding portion thereof, exhibits reduced synovial proliferation, reduced cell infiltration, reduced chondrocyte death, and/or reduced proteoglycan loss as compared to a non-low impurity composition. In another embodiment, a low impurity composition comprising an anti-TNFα antibody, or antigen-binding portion thereof, exhibits increased TNFα affinity as compared to a non-low impurity composition.

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, or synovial fluid of the subject), which can be detected, for example, using an anti-TNFα antibody as described above. There are numerous examples of disorders in which TNFα activity is detrimental. In one embodiment, the disorder in which TNFα activity is detrimental is an autoimmune disorder. In one embodiment, the autoimmune disorder is selected from the group consisting of rheumatoid arthritis, juvenile idiopathic arthritis, rheumatoid spondylitis, ankylosing spondylitis, psoriasis, osteoarthritis, gouty arthritis, an allergy, multiple sclerosis, psoriatic arthritis, autoimmune diabetes, autoimmune uveitis, nephrotic syndrome, juvenile rheumatoid arthritis, Crohn's disease, ulcerative colitis, active axial spondyloarthritis (active axSpA) and non-radiographic axial spondyloarthritis (nr-axSpA). Disorders in which TNFα activity is detrimental are set forth in U.S. Pat. No. 6,090,382 and also in the Humira® Prescribing Information, the contents of each of which are hereby incorporated herein by reference. The use of TNFα antibodies and antibody portions obtained using methods of the invention for the treatment of specific disorders is discussed in further detail below.

In a particular embodiment, the impurity is a process-related impurity. As used herein, the term "process-related impurity," refers to impurities that are present in a composition comprising a protein of interest but are not derived from the protein itself. Process-related impurities include, but are not limited to, host cell proteins (HCPs), host cell nucleic acids, chromatographic materials, and media components. A "low process-related impurity composition," as used herein, refers to a composition comprising reduced levels of process-related impurities as compared to a composition wherein the impurities were not reduced. For example, a low process-related impurity composition may contain about 10%, 9%, 8%, 7%, 6%, 5%, 4%, 3%, 2%, 1%, 0.5%, or less process-related impurities. In one embodiment, a low process-related impurity composition is free of process-related impurities or is substantially free of process-related impurities.

In one embodiment, the impurity is a host cell protein. The term "host cell protein" (HCP), as used herein, is intended to refer to non-protein of interest proteinaceous impurities derived from host cells, for example, host cells used to produce the protein of interest.

In one embodiment, the impurity is a host cell nucleic acid. The term "host cell nucleic acids", as used herein, is intended to refer to nucleic acids derived from host cells, for example, host cells used to produce the protein of interest.

In a particular embodiment, the impurity is a product-related substance. As used herein, the term "product-related substance" refers to variants of the protein of interest formed during manufacturing and/or storage of the protein of interest. Specific examples of product-related substances include degradants of the protein, truncated forms of the protein, high molecular weight species, low molecular weight species, fragments of the protein, modified forms of the protein, including deamidated, isomerized, mismatched S—S linked, oxidized or altered conjugate forms (e.g., glycosylation, phosphorylation), aggregates including dimers and higher multiples of the protein of interest, and charge variants.

In a particular embodiment, the impurity is an aggregate. As used herein, the term "aggregate" refers to agglomeration or oligomerization of two or more individual molecules of the protein of interest to form, for example, dimers, trimers, tetramers, oligomers and other high molecular weight species. Protein aggregates can be soluble or insoluble. In a particular embodiment, the aggregate is a multimer of adalimumab. In a particular embodiment, the aggregate is a dimer of adalimumab. In another embodiment, the aggregate is a trimer of adalimumab. In another embodiment, the aggregate is a tetramer of adalimumab.

Figure 1:
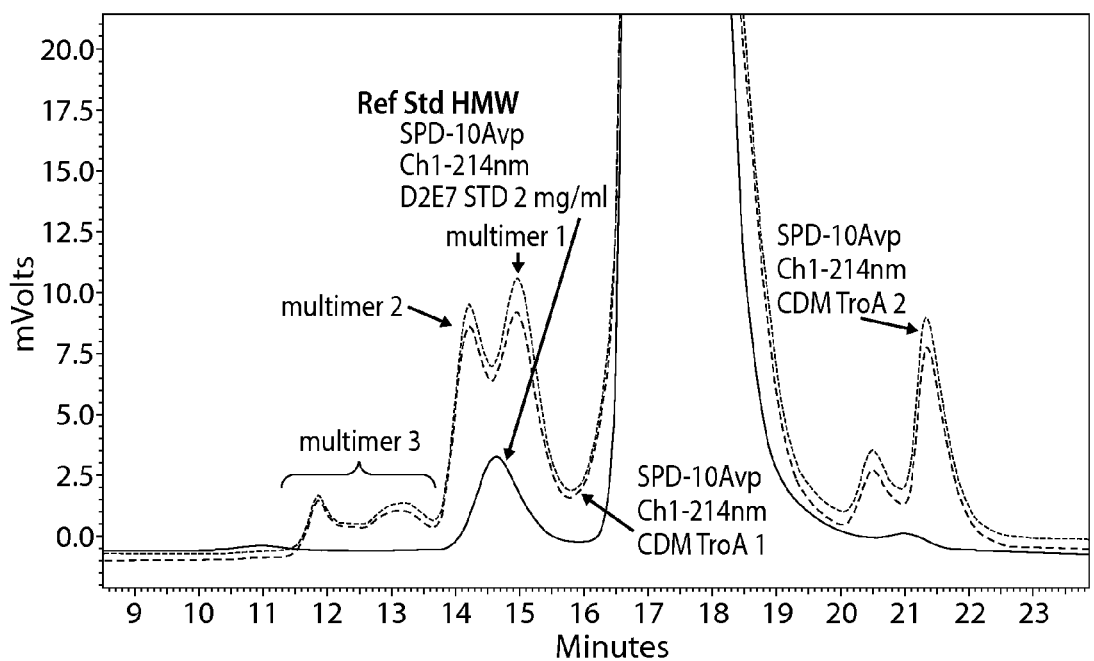
Figure 2A:
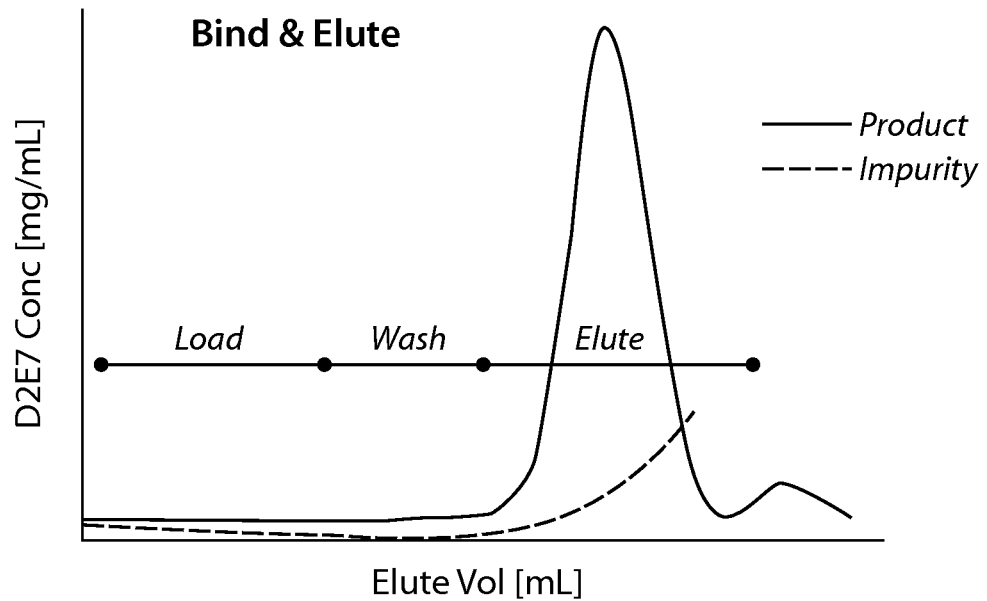
Figure 2B:
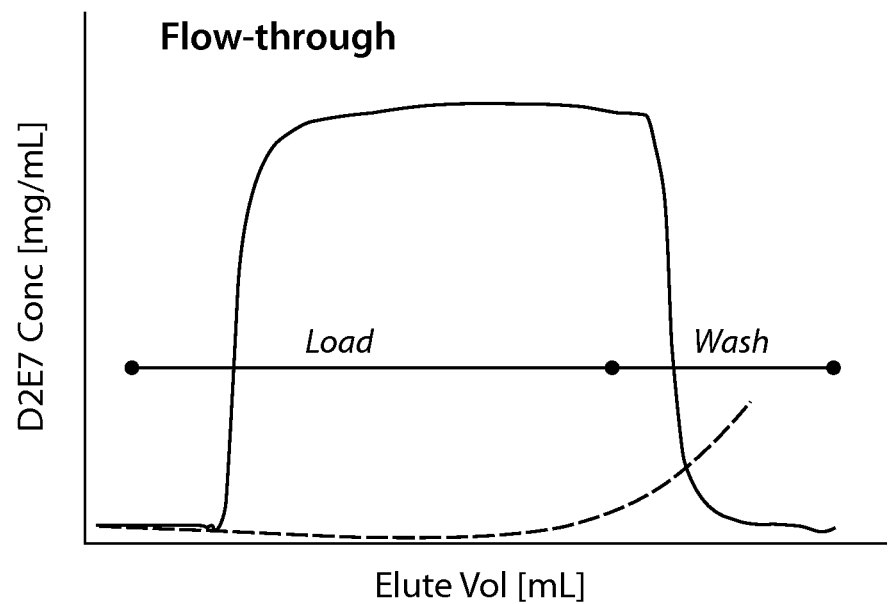
Figure 3:
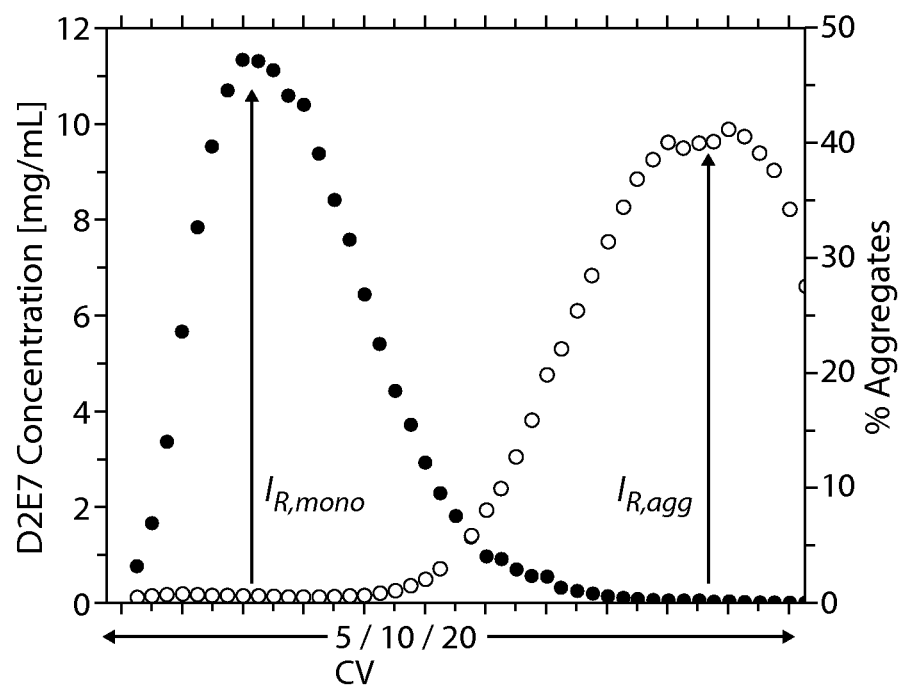

In certain embodiments, the sample can comprise more than one type of aggregate. For example, but not by way of limitation, the nature of the aggregates and total aggregate composition can be identified based on chromatographic residence time. For example, FIG. 1 depicts a size exclusion chromatography (SEC) chromatogram used to determine the molecular weight distribution of a sample of adalimumab.

As set forth therein, the total aggregate species associated with the expression of adalimumab can be divided into multimer 1 (MM1), multimer 2 (MM2) and multimer 3 (MM3). In various embodiments, the methods of the present invention serve to reduce the levels of one of MM1, MM2 or MM3. In another embodiment, the methods of the present invention serve to reduce the levels of MM1 and MM2. In another embodiment, the methods of the present invention serve to reduce the levels of MM1 and MM3. In another embodiment, the methods of the present invention serve to reduce the levels of MM2 and MM3. In yet another embodiment, the methods of the present invention serve to reduce the levels of MM1, MM2 and MM3.

In one embodiment, the methods of the invention generate a preparation comprising a protein of interest and having a reduced level of aggregate. As used herein, a "reduced level of aggregate" refers to a composition comprising reduced levels of an aggregate as compared to the levels of the aggregate in the sample prior to purification by the methods of the present invention. In one embodiment, a preparation having a reduced level of aggregate is free of the aggregate or substantially free of the aggregate. In another embodiment, the methods of the invention generate a preparation comprising a protein of interest and having a reduced level of total aggregate. As used herein a "reduced level of total aggregate" refers to a composition comprising reduced levels of total aggregate as compared to the levels of the impurity in the sample prior to purification by the methods of the present invention. In one embodiment, a preparation having a reduced level of total aggregate is free of aggregates or substantially free of the aggregates.

The present invention is further directed to low aggregate compositions and methods of generating the same, for example, low aggregate compositions of adalimumab. The term "low aggregate composition," as used herein, refers to a composition comprising a protein of interest, wherein the composition contains less than about 15% total aggregates. For example, a low aggregate composition may contain about 10%, 9%, 8%, 7%, 6%, 5%, 4%, 3%, 2%, 1.5%, 1.4%, 1.3%, 1.2%, 1.1%, 1%, 0.5%, or less total aggregates. In a particular embodiment, a low aggregate composition comprises about 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less total aggregates.

In one embodiment, a low aggregate composition of adalimumab can comprise about 10%, 9%, 8%, 7%, 6%, 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less of MM1, or 0.0% of MM1. In another embodiment, a low aggregate composition of adalimumab can comprise about 10%, 9%, 8%, 7%, 6%, 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less of MM2, or 0.0% of MM2. In another embodiment, a low aggregate composition of adalimumab can comprise about 10%, 9%, 8%, 7%, 6%, 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less of MM3, or 0.0% of MM3.

The term "non-low aggregate composition," as used herein, refers to a composition comprising a protein of interest, which contains more than about 15% total aggregates. For example, a non-low aggregate composition may contain about 15%, 16%, 17%, 18%, 19%, 20%, 21%, 22%, 23%, 24%, 25%, or more total aggregates. In one embodiment, a non-low aggregate composition of adalimumab can comprise about 15%, 16%, 17%, 18%, 19%, 20%, 21%, 22%, 23%, 24%, 25%, or more of MM1. In another embodiment, a non-low aggregate composition or adalimumab can comprise about 15%, 16%, 17%, 18%, 19%, 20%, 21%, 22%, 23%, 24%, 25%, or more of MM2. In another embodiment, a non-low aggregate composition or adalimumab can comprise about 15%, 16%, 17%, 18%, 19%, 20%, 21%, 22%, 23%, 24%, 25%, or more of MM3.

In one embodiment, a low aggregate composition has improved biological and functional properties, including increased efficacy in the treatment or prevention of a disorder in a subject, e.g., a disorder in which TNFα activity is detrimental, as compared to a non-low aggregate composition. In one embodiment, the low aggregate composition comprises an anti-TNFα antibody, or antigen-binding portion thereof, such as adalimumab or a fragment thereof. For example, in one embodiment, a low aggregate composition comprising an antibody, or antigen-binding portion thereof, exhibits increased cartilage penetration, decreased bone erosion, and/or reduced cartilage destruction, as compared to a non-low aggregate composition comprising the same antibody or antigen binding portion thereof, when administered to a subject suffering from a disorder in which TNFα activity is detrimental.

In another embodiment, a low aggregate composition comprising an antibody, or antigen-binding portion thereof, exhibits increased protection against the development of arthritic scores and/or histopathology scores as compared to a non-low aggregate composition when administered to an animal model of arthritis, e.g., the TNF-Tg197 model of arthritis, as described above.

In another embodiment, a low aggregate composition comprising an antibody, or antigen-binding portion thereof, exhibits reduced synovial proliferation, reduced cell infiltration, reduced chondrocyte death, and/or reduced proteoglycan loss as compared to a non-low aggregate composition. In another embodiment, a low aggregate composition comprising an anti-TNFα antibody, or antigen-binding portion thereof, exhibits increased TNFα affinity as compared to a non-low aggregate composition.

In a particular embodiment, the impurity is a fragment of the protein of interest. The term "fragment" as used herein refers to any truncated form of a protein of interest, resulting from, for example, dissociation of a peptide chain, or enzymatic and/or chemical modifications.

In a particular embodiment, the impurity is a charge variant. The term "charge variant", as used herein, refers to the full complement of product variants including, but not limited to acidic species, and basic species (e.g., Lys variants). In certain embodiments, such variants can include product aggregates and/or product fragments, to the extent that such aggregation and/or fragmentation results in a product charge variation as seen in an analytical technique used for that purpose.

As used herein, the terms "acidic species," "acidic region," and "AR," refer to the variants of a protein, e.g., an antibody or antigen-binding portion thereof, which are characterized by an overall acidic charge. For example, in monoclonal antibody (mAb) preparations, such acidic species can be detected by various methods, such as ion exchange, for example, WCX-10 HPLC (a weak cation exchange chromatography), or IEF (isoelectric focusing). Acidic species of an antibody may include charge variants, structure variants, and/or fragmentation variants. Exemplary charge variants include, but are not limited to, deamidation variants, afucosylation variants, methylglyoxal (MGO) variants, glycation variants, and citric acid variants. Exemplary structure variants include, but are not limited to, glycosylation variants and acetonation variants. Exemplary fragmentation variants include any truncated protein species from the target molecule due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants include variants containing unpaired disulfides, host cell proteins, and host nucleic acids, chromatographic materials, and media components.

In certain embodiments, a protein composition can comprise more than one type of acidic species variant. For example, but not by way of limitation, the total acidic species can be divided based on chromatographic residence time. For example, the total acidic species associated with the expression of adalimumab can be divided into a first acidic species region (AR1) and a second acidic species region (AR2).

AR1 can comprise, for example, charge variants such as deamidation variants, MGO modified species, glycation variants, and citric acid variants, structural variants such as glycosylation variants and acetonation variants, and/or fragmentation variants. Other acidic variants such as host cells and unknown species may also be present. In another embodiment, AR2 can comprise, for example, charge variants such as glycation variants and deamidation variants. Other acidic variants such as host cells and unknown species may also be present.

With respect, in particular, to adalimumab (and antibodies sharing certain structural characteristics of adalimumab, e.g., one or more CDR and/or heavy and light chain variable regions of adalimumab), AR1 charge variants can comprise, but are not limited to, deamidation variants, glycation variants, afucosylation variants, MGO variants or citric acid variants. In one embodiment, deamidation variants result from deamidation occurring at asparagine residues comprising Asn393 and Asn329 and at glutamine residues comprising Gln3 and Gln6. In another embodiment, the glycation variants result from glycation occurring at Lys98 and Lys151. AR1 structure variants can comprise, but are not limited to, glycosylation variants or acetonation variants. AR1 fragmentation variants can comprise Fc and Fab fragments, fragments missing a Fab, fragments missing a heavy chain variable domain, C-terminal truncation variants, variants with excision of N-terminal Asp in the light chain, and variants having N-terminal truncation of the light chain. AR2 charge variants can comprise, but are not limited to, deamidation variants or glycation variants, wherein the deamidation variants can result from deamidation occurring at asparagine residues comprising Asn393 and Asn329 and at glutamine residues comprising Gln3 and Gln6, and the glycation variants can result from glycation occurring at Lys98 and Lys151.

Acidic species may also include process-related impurities.

The acidic species may be the result of product preparation (referred to herein as "preparation-derived acidic species"), or the result of storage (referred to herein as "storage-derived acidic species"). Preparation-derived acidic species are acidic species that are formed during the preparation (upstream and/or downstream processing) of the protein, e.g., the antibody or antigen-binding portion thereof. For example, preparation-derived acidic species can be formed during cell culture ("cell culture-derived acidic species"). Storage-derived acidic species are acidic species that are not present in the population of proteins directly after preparation, but are formed while the sample is being stored. The type and amount of storage-derived acidic species can vary based on the formulation of the sample. Formation of storage-derived acidic species can be partially or completely inhibited when the preparation is stored under particular conditions. For example, an aqueous formulation can be stored at a particular temperature to partially or completely inhibit AR formation. For example, formation or storage-derived AR can be partially inhibited in an aqueous formulation stored at between about 2° C. and 8° C., and completely inhibited when stored at −80° C.

In addition, a low AR composition can be lyophilized to partially or completely inhibit the formation of storage-derived AR.

The term "low acidic species composition," as used herein, refers to a composition comprising an antibody or antigen binding portion thereof, wherein the composition contains less than about 15% acidic species. For example, a low acidic species composition may contain about 10%, 9%, 8%, 7%, 6%, 5%, 4%, 3%, 2%, 1.5%, 1.4%, 1.3%, 1.2%, 1.1%, 1%, 0.5%, or less acidic species. In one embodiment, a low acidic species composition can comprise about 10%, 9%, 8%, 7%, 6%, 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less of AR1, or 0.0% of AR1. In another embodiment, a low acidic species composition can comprise about 10%, 9%, 8%, 7%, 6%, 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less of AR2, or 0.0% of AR2. In a preferred embodiment, a low acidic species composition comprises about 5%, 4%, 3%, 2.5%, 2.4%, 2.3%, 2.2%, 2.1%, 2%, 1.5%, 1.4%, 1.3%, 1.2%, 1.1%, 1%, 0.5%, 0.1%, or less acidic species. In one embodiment, a low acidic species composition comprises about 0.1% or less AR1 and about 3% or less AR2. In another preferred embodiment, a low acidic species composition comprises about 1% or 0.1% or less AR1. In still another preferred embodiment, a low acidic species composition comprises about 3% or less AR2. In another preferred embodiment, the low AR composition comprises about 1.4% or less AR. For example, in one embodiment, the composition comprises about 1.4% AR2 and about 0.0% AR1.

The term "non-low acidic species composition," as used herein, refers to a composition comprising an antibody or antigen binding portion thereof, which contains more than about 15% acidic species. For example, a non-low acidic species composition may contain about 15%, 16%, 17%, 18%, 19%, 20%, 21%, 22%, 23%, 24%, 25%, or more acidic species. In one embodiment, a non-low acidic species composition can comprise about 15%, 16%, 17%, 18%, 19%, 20%, 21%, 22%, 23%, 24%, 25%, or more of AR1. In another embodiment, a non-low acidic species composition can comprise about 15%, 16%, 17%, 18%, 19%, 20%, 21%, 22%, 23%, 24%, 25%, or more of AR2.

In one embodiment, a low AR composition has improved biological and functional properties, including increased efficacy in the treatment or prevention of a disorder in a subject, e.g., a disorder in which TNFα activity is detrimental, as compared to a non-low acidic species composition. In one embodiment, the low AR composition comprises an anti-TNFα antibody, or antigen-binding portion thereof, such as adalimumab or a fragment thereof. For example, in one embodiment, a low AR composition comprising an antibody, or antigen-binding portion thereof, exhibits increased cartilage penetration, decreased bone erosion, and/or reduced cartilage destruction, as compared to a non-low acidic species composition comprising the same antibody or antigen binding portion thereof, when administered to a subject suffering from a disorder in which TNFα activity is detrimental.

In another embodiment, a low AR composition comprising an antibody, or antigen-binding portion thereof, exhibits increased protection against the development of arthritic scores and/or histopathology scores as compared to a non-low acidic species composition when administered to an animal model of arthritis, e.g., the TNF-Tg197 model of arthritis, as described above.

In another embodiment, a low AR composition comprising an antibody, or antigen-binding portion thereof, exhibits reduced synovial proliferation, reduced cell infiltration, reduced chondrocyte death, and/or reduced proteoglycan loss as compared to a non-low acidic species composition. In another embodiment, a low AR composition comprising an anti-TNFα antibody, or antigen-binding portion thereof, exhibits increased TNFα affinity as compared to a non-low acidic species composition.

In another embodiment, the impurity is a lysine variant species. As used herein, the term "lysine variant species" refers to an antibody, or antigen-binding portion thereof, comprising heavy chains with either zero, one or two C-terminal lysines. For example, the "Lys 0" variant comprises an antibody, or antigen-binding portion thereof, with heavy chains that do not comprise a C-terminal lysine. The "Lys 1" variant comprises an antibody, or antigen-binding portion thereof, with one heavy chain that comprises a C-terminal lysine. The "Lys 2" variant comprises an antibody with both heavy chains comprising a C-terminal lysine. Lysine variants can be detected, for example, by weak cation exchange chromatography (WCX) of the expression product of a host cell expressing the antibody, or antigen-binding portion thereof. With respect specifically to adalimumab, three main basic lysine variant species have been identified, i.e., Lys 0, Lys 1, and Lys 2.

The term "load buffer", as used herein refers to a salt solution passed through the HIC media upon contacting the sample with the HIC media. In certain embodiments, the load buffer is passed through the HIC media simultaneously or substantially simultaneously with passage of the sample through the HIC media. In certain embodiments, the load buffer is combined with the sample prior to passage through the HIC media.

The term "flow through fraction", as used herein refers to the liquid that passes through without binding the hydrophobic column upon contacting the sample with the HIC media during the load cycle. According to the methods of the present invention, the flow through fraction includes protein of interest that does not bind to the HIC media. The flow through fraction may also include load buffer that passes through the HIC media during the load cycle and/or a portion of the impurity that does not bind to the HIC media.

The term "wash buffer", as used herein refers to a salt solution passed through the HIC media during the wash cycle.

The term "wash fraction", as used herein refers to the liquid eluted from the column upon washing the HIC media with the wash buffer. According to the methods of the present invention, the wash fraction includes protein of interest that is released from the HIC media upon exposure to the wash buffer. The wash fraction may also include wash buffer that passes through the HIC media during the wash cycle and/or a portion of the impurity that does not bind to the HIC media.

The term "isocratic", as used herein, refers to wash and load conditions which are identical or vary only slightly in terms of, for example, the nature of the buffer, the salt concentration, the pH, and the temperature. In particular embodiments, the wash and load conditions are substantially the same, for example, the salt concentration and/or the pH of the wash buffer are identical to or are adjusted to within about 20%, about 15%, about 10%, or about 5% of the salt concentration, and/or pH of the loading buffer. In a particular embodiment, the wash and load conditions are identical.

The term "load challenge", as used herein refers to the total mass of sample (e.g., protein of interest and at least one protein) loaded onto the column in chromatography applications or applied to the resin in batch binding, measured in units of mass of product per unit volume of resin.

As used herein, the term "dynamic binding capacity" refers to the amount of total protein that binds to the HIC media upon breakthrough of 10% of the total protein load.

As used herein, the term "apparent binding capacity" refers to the amount of protein of interest that binds to the HIC media upon breakthrough of 10% of the total protein load, in reversible HIC binding applications.

As used herein, the term "actual binding capacity" refers to the amount of protein of interest that remains bound to the chromatographic media under isocratic wash conditions.

As used herein, the term "equilibrium binding capacity" refers to the maximum amount of total protein that can be bound under certain conditions.

As used herein, the term "partition coefficient" (Kp) refers to the equilibrium ratio of the concentration of protein of interest adsorbed to the HIC media to the concentration of protein of interest in the solution comprising the unbound protein of interest, under specified conditions of pH and solution composition. The partition coefficient Kp corresponds to the slope of the protein of interest adsorption isotherm at very low solution concentrations. Kp can be calculated from the Qmax (maximum capacity of the HIC media for the protein of interest) and Kd (dissociation constant for the HIC media-protein of interest interaction) as follows: $Kp=Q/C=Qmax/Kd$.

Protein Purification
Protein Purification Generally

The present invention provides a method for producing a preparation including a protein of interest, e.g., an antibody, and having a reduced level of at least one impurity, e.g., an aggregate, by contacting a sample including the protein of interest and at least one impurity, to a hydrophobic interaction chromatography media.

In certain embodiments, the compositions of the present invention include, but are not limited to, a preparation comprising a protein of interest having a reduced level of at least one impurity. For example, but not by way of limitation, the present invention is directed to preparations of adalimumab having a reduced level of at least one impurity, for example, aggregate. Such preparations having a reduced level of at least one impurity address the need for improved product characteristics, including, but not limited to, product stability, product safety and product efficacy. In further embodiments, compositions of the present invention include pharmaceutical compositions comprising the preparation produced by the methods of the invention (e.g., protein of interest having a reduced level of the at least on impurity) and a pharmaceutically acceptable carrier.

In certain embodiments, the purification process of the invention begins at the separation step when the protein of interest has been produced using production methods described above and/or by alternative production methods conventional in the art. Once a clarified solution or sample comprising the protein of interest has been obtained, separation of the protein of interest from at least one impurity, such as process-related impurities, e.g., other proteins produced by the cell, as well as any product-related substances, e.g., charge variants and/or size variants (aggregates and fragments), can be performed using a HIC separation step, or a combination of a HIC separation step and one or more purification techniques, including filtration and/or affinity, ion exchange, and/or mixed mode chromatographic step(s), as outlined herein.

Primary Recovery

In certain embodiments, the initial steps of the purification methods of the present invention involve the clarification and primary recovery of protein of interest, for example, antibody, following production. In certain embodiments, the primary recovery will include one or more centrifugation steps to separate the protein of interest from cells and cell debris. Centrifugation of the protein containing composition can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample and thereby aid in purifying the protein of interest in the present invention. In other embodiments, the primary recovery will include the use of one or more depth filtration steps post centrifugation to further clarify the sample. Non-limiting examples of depth filters that can be used in the context of the instant invention include the Millistak+X0HC, F0HC, D0HC, A 1HC, B1HC depth filters (EMD Millipore), Cuno™ model 30/60ZA, 60/90 ZA, VR05, VR07, delipid depth filters (3M Corp.). A 0.2 μm filter such as Sartorius's 0.45/0.2 μm Sartopore™ bi-layer or Millipore's Express SHR or SHC filter cartridges typically follows the depth filters.

In certain embodiments, the primary recovery process can also be a point at which to reduce or inactivate viruses that can be present in the sample. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972. In certain embodiments of the present invention, the sample is exposed to detergent viral inactivation during the primary recovery phase. In other embodiments, the sample may be exposed to low pH inactivation during the primary recovery phase.

In those embodiments where viral reduction/inactivation is employed, the sample can be adjusted, as needed, for further purification steps. For example, following low pH viral inactivation, the pH of the sample is typically adjusted to a more neutral pH, e.g., from about 4.5 to about 8.5, prior to continuing the purification process. Additionally, the mixture may be diluted with water for injection (WFI) to obtain a desired conductivity.

Hydrophobic Interaction Chromatography

The instant invention features methods for producing a preparation comprising a protein of interest (e.g., the anti-TNFα antibody adalimumab, or a fragment thereof) having a reduced level of at least one impurity, for example, aggregate, from a sample comprising the protein of interest and at least one impurity by contacting the sample with HIC media.

According to the present invention, HIC purification of a protein of interest comprises reversible binding of the protein of interest and binding of one or more impurities through hydrophobic interaction with hydrophobic moieties attached to a solid matrix support (e.g., agarose). The hydrophobic interaction between molecules results from the tendency of a polar environment to exclude non-polar (i.e., hydrophobic) molecules. HIC relies on this principle of hydrophobicity of molecules (i.e., the tendency of a given protein to bind adsorptively to hydrophobic sites on a hydrophobic adsorbent body) to separate biomolecules based on their relative strength of interaction with the hydrophobic moieties (see, e.g., U.S. Pat. No. 4,000,098 and U.S. Pat. No. 3,917,527 which are herein incorporated by reference in their entirety). An advantage of this separation technique is its non-denaturing characteristics and the stabilizing effects of salt solutions used during loading, washing and or eluting.

Hydrophobic interaction chromatography employs the hydrophobic properties of molecules (e.g., proteins, polypeptides, lipids) to achieve separation of even closely-related molecules. Hydrophobic groups on the molecules interact with hydrophobic groups of the media or the membrane. In certain embodiments, the more hydrophobic a molecule is, the stronger it will interact with the column or the membrane.

Thus, HIC steps, such as those disclosed herein, can be used to remove a variety of impurities, for example, process-related impurities (e.g., DNA) as well as product-related species (e.g., high and low molecular weight product-related species, such as protein aggregates and fragments).

In one aspect, the present invention provides a method for producing a preparation including a protein of interest, e.g., an antibody, and having a reduced level of at least one impurity, e.g., an aggregate, by (a) contacting a sample including the protein of interest and at least one impurity, to a hydrophobic interaction chromatography media, in the presence of a load buffer such that (i) a portion of the protein of interest binds to the hydrophobic interaction chromatography (HIC) media and (ii) a substantial portion of the at least one impurity binds to the HIC media; (b) collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein each of the flow through and wash fractions include the protein of interest and have a reduced level of the at least one impurity. In a particular embodiment, the portion of the protein of interest binds to the HIC media at a Kp of greater than 10. In a particular embodiment, the portion of the protein of interest binds to the HIC media at a Kp of greater than 20. In a particular embodiment, the portion of the protein of interest binds to the HIC media at a Kp of greater than 100.

In another aspect, the present invention provides a method for producing a preparation including a protein of interest, e.g., an antibody, and having a reduced level of at least one impurity, e.g., an aggregate, by (a) contacting a sample including the protein of interest and at least one impurity, to a HIC media, in the presence of a load buffer such that (i) a portion of the protein of interest binds to the HIC media and (ii) a substantial portion of the at least one impurity binds to the HIC media; collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein either (i) the substantial portion of the at least one impurity binds to the HIC media at a Kp greater than 200 and/or (ii) the protein of interest and the at least on impurity have a Kp ratio less than 1:7; and wherein each of the flow through and wash fractions include the protein of interest and have a reduced level of the at least one impurity.

In yet another aspect, the present invention provides a method for producing a preparation including a protein of interest, e.g., an antibody, and having a reduced level of at least one impurity, e.g., an aggregate, by (a) contacting a sample including the protein of interest and at least one impurity, to a HIC media, in the presence of a load buffer such that (i) a portion of the protein of interest binds to the HIC media, and (ii) a substantial portion of the at least one impurity binds to the HIC media; (b) collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein the $K_d$ for the binding of the protein of interest to the HIC media is less than 60, 50, 45, 40, 35, 30, 25, 20, 15, 10, 5 or 2 times the $K_d$ for the binding of the at least one impurity to the HIC media, and wherein each of the flow through and wash fractions include the protein of interest and have a reduced level of the at least one impurity.

According to the present invention, a portion of the protein of interest reversibly binds to the HIC media while a portion of the protein of interest flows through to form a flow through fraction which has a reduced level of impurity. The portion of the protein of interest that binds to the HIC media binds reversibly in that the bound protein of interest may be released therefrom under isocratic conditions, for example, by use of a wash buffer that is substantially the same as the load buffer. In contrast, a substantial portion of the at least impurity in the sample binds the HIC media upon loading and a substantial portion thereof remains bound upon washing the HIC media with the wash buffer.

The present invention is based, at least in part, on the finding that such reversible binding can be achieved at relatively high binding strength. For example, contrary to the teachings of U.S. Pat. No. 8,067,182 which teaches weak partitioning binding of a product, i.e., at a Kp of between 0.1 and 20 and less than 10 for HIC, according to the methods of the present invention, the protein of interest may bind at higher Kp levels so as to achieve higher purification and greater recovery of the protein of interest. For example, in a particular embodiment, the protein of interest binds to the HIC media at a Kp of greater than 10, 15, 20, 50, 60, 70, 80, 90, 100, 110, 120, 130, 140, 150, 160, 170, 180, 190, 200, 220, 250, 300, 400 or 500. In one embodiment, the protein of interest binds to the HIC media at a Kp greater than 10. In another embodiment, the protein of interest binds to the HIC media at a Kp greater than 20. In another embodiment, the protein of interest binds to the HIC media at a Kp of greater than 90.

According to the present invention, the impurity binds at a higher strength and, thus to a greater degree to the HIC media, thereby allowing for selective release of the bound protein of interest upon wash. For example, in particular embodiments, the at least one impurity binds to the HIC media at a Kp of greater than 200, greater than 250, greater than 300, greater than 400, greater than 500, greater than 600, greater than 700, greater than 800, greater than 900, greater than 1000, or greater than 2000. In a specific embodiment, the at least one impurity binds to the HIC media at a Kp of greater than 600.

In a further embodiment, the protein of interest and the at least one impurity have a Kp ratio less than 1:10, less than 1:9, less than 1:8, less than 1:7, less than 1:6, less than 1:5, less than 1:4, less than 1:3 or less than 1:2. In a specific embodiment, the protein of interest and the at least one impurity have a Kp ratio less than 1:7.

The relative strength of binding may also be assessed by determining $K_d$, the dissociation constant for the media-protein of interest interaction, or the media-impurity interaction. In one embodiment of the invention, the $K_d$ for the binding of the protein of interest to the HIC media is at least about 0.2, at least about 0.3, at least about 0.4, at least about 0.5, at least about 0.6, at least about 0.7, or at least about 0.8. In a preferred embodiment, the $K_d$ for the binding of the protein of interest to the HIC media is at least about 0.4.

In another embodiment of the invention, the $K_d$ of the binding of the at least one impurity to the HIC media is less than or equal to about 0.001, about 0.005, about 0.01, about 0.02, about 0.05, about 0.1, about 0.15, about 0.2, about 0.3, about 0.4, about 0.5, or about 1.0. In a particular embodiment the $K_d$ for the at least one impurity is less than or equal to about 0.01.

In another embodiment of the invention, the $K_d$ for the binding of the protein of interest to the HIC media is less than 60, 50, 45, 40, 35, 30, 25, 20, 15, 10, 5 or 2 times the $K_d$ for the binding of the at least one impurity to the HIC media.

The relative binding capacity of the protein of interest may also be assessed by determining Qmax, the maximum capacity of the media for the protein of interest, or for the at least one impurity. In one embodiment of the invention, the protein of interest has a Qmax of at least about 20, at least about 30, at least about 40, at least about 50, at least about 60, at least about 100, at least about 250, or at least about 500. In a preferred embodiment, the protein of interest has a Qmax of at least about 40.

In another embodiment, the at least one impurity has a Qmax of at least about 2, at least about 5, at least about 10, at least about 20, at least about 30, at least about 40, at least about 50, at least about 75, or at least about 100. In a preferred embodiment, the at least one impurity has a Qmax of at least about 5.

In performing the HIC separation, the sample is contacted with the HIC media, e.g., using a batch purification technique or using a column or membrane chromatography or monolithic material (referred to as HIC media or resin). For example, in the context of chromatographic separation, a chromatographic apparatus, commonly cylindrical in shape, is employed to contain the chromatographic support media (e.g., HIC media) prepared in an appropriate buffer solution. Once the chromatographic material is added to the chromatographic apparatus, a sample containing the protein of interest, e.g., an antibody, and the protein of interest is contacted to the chromatographic material in the presence of a loading buffer to allow binding of a portion of the protein of interest and a substantial portion of the impurity to the HIC media. A portion of the protein of interest in the sample binds to the HIC media while a portion of the protein interest flows through, forming a flow through fraction having a reduced level of impurity which is collected.

In one embodiment, the portion of the protein of interest that binds to the HIC media is at least about 20%, at least about 30%, at least about 40%, at least about 50%, at least about 60%, at least about 70%, at least about 80%, at least about 90%, at least about 95% or at least about 98% of the amount of the protein of interest in the sample.

Alternatively or in combination, the substantial portion of the at least one impurity that binds to the HIC media is at least about 60%, at least about 65%, at least about 70%, at least about 75%, at least about 80%, at least about 85%, at least about 90%, at least about 95%, at least about 98% or about 100% of the level of the at least one impurity in the sample.

Alternatively or in combination, the portion of the protein of interest that flows through without binding to the HIC media is at least about 20%, at least about 30%, at least about 40%, at least about 50%, at least about 60%, at least about 70%, at least about 80%, at least about 90%, at least about 95% or at least about 98% of the amount of the protein of interest in the sample.

The media is then subjected to a wash buffer, thereby allowing for a portion of the bound protein of interest to release from the HIC media in a wash fraction which is collected, while a substantial portion of the impurity remains bound to the HIC media. After loading, the column can be regenerated with water and cleaned with caustic solution to remove the bound impurities before next use.

In one embodiment, the substantial portion of the protein of interest released from the HIC media upon washing with the wash buffer is at least about at least about 50%, at least about 60%, at least about 70%, at least about 80%, at least about 90%, at least about 95%, at least about 98%, or about 100% of the amount of protein of interest bound to the HIC media.

Alternatively or in combination, the substantial portion of the impurity that remains bound to the HIC media is at least about 50%, at least about 60%, at least about 65%, at least about 70%, at least about 75%, at least about 80%, at least about 85%, at least about 90%, at least about 95%, at least about 98% or about 100% of the impurity bound to the HIC media during the load cycle.

In order to achieve the desired reversible binding of the protein of interest and the comparable strong binding of the at least one impurity, appropriate selection of resin, buffer, concentration, pH and sample load is required. Techniques to identify optimal conditions for achieving such desired binding profile are set forth in the Examples below.

Hydrophobic interactions are strongest at high salt concentration (and hence the ionic strength of the anion and cation components). Adsorption of the protein of interest to a HIC column is favored by high salt concentrations, but the actual concentrations can vary over a wide range depending on the nature of the protein of interest, salt type and the particular HIC ligand chosen. In various embodiments, the salt concentration may be in the range of, for example, about 50 mM to about 5000 mM, about 100 mM to about 4000 mM, about 1000 mM to about 4000 mM, about 50 mM to about 2000 mM, depending, in part, on the salt type and HIC adsorbent. In one embodiment the salt concentration is about 50 mM, about 55 mM, about 60 mM, about 65 mM, about 70 mM, about 75 mM, about 80 mM, about 85 mM, about 90 mM, about 100 mM, about 200 mM, about 300 mM, about 400 mM, about 500 mM, about 600 mM, about 700 mM, about 800 mM, about 900 mM, about 1000 mM, about 1200 mM, about 1400 mM, about 1600 mM, about 1800 mM or about 2000 mM.

Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In certain embodiments, the anionic part of the salt is chosen from among sulfate, citrate, chloride, or a mixture thereof. In certain embodiments, the cationic part of the salt is chosen from among ammonium, sodium, potassium, or a mixture thereof. In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4$>$Na_2SO_4$>NaCl>$NH_4Cl$>NaBr>NaSCN. In general, salt concentrations of between about 0.75 and about 2 M ammonium sulfate or between about 1 and 4 M NaCl are useful. In another embodiment, the load buffer and the wash buffer comprise a salt of the Hofmeister series or lyotropic series of salts.

In one embodiment, the load buffer and the wash buffer comprise a sulfate salt, a citrate salt, or a combination thereof. In another embodiment, the sulfate salt in ammonium sulfate. In another embodiment, the sulfate salt is a sodium sulfate. In yet another embodiment, the citrate salt is sodium citrate. In certain embodiments, the load and/or wash buffer may be comprised of at least 2 salts.

In certain embodiments, the HIC adsorbent material is composed of a chromatographic backbone with pendant hydrophobic interaction ligands. For example, but not by way of limitation, the HIC media can be composed of convective membrane media with pendent hydrophobic interaction ligands, convective monolithic media with pendent hydrophobic interaction ligands, and/or convective filter media with embedded media containing the pendant hydrophobic interaction ligands.

In certain embodiments, the HIC adsorbent material can comprise a base matrix (e.g., derivatives of cellulose, polystyrene, synthetic poly amino acids, synthetic polyacrylamide gels, cross-linked dextran, cross-linked agarose, synthetic copolymer material or even a glass surface) to which hydrophobic ligands (e.g., alkyl, aryl and combinations thereof) are coupled or covalently attached using difunctional linking groups such as —NH—, —S—, —COO—, etc. The hydrophobic ligand may be terminated in a hydrogen but can also terminate in a functional group such as, for example, $NH_2$, $SO_3H$, $PO_4H_2$, SH, imidazoles, phenolic groups or non-ionic radicals such as OH and $CONH_2$. In one embodiment, the HIC media comprises at least one hydrophobic ligand. In another embodiment, the hydrophobic ligand is selected from the group consisting of butyl, hexyl, phenyl, octyl, or polypropylene glycol ligands.

One, non-limiting, example of a suitable HIC media comprises an agarose media or a membrane functionalized with phenyl groups (e.g., a Phenyl Sepharose™ from GE Healthcare or a Phenyl Membrane from Sartorius). Many HIC medias are available commercially. Examples include, but are not limited to, Tosoh Hexyl, CaptoPhenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, New Jersey); Toyopearl™ ether, phenyl or butyl (TosoHaas, PA); Toyo-Screen PPG, ToyoScreen Phenyl, ToyoScreen Butyl, and ToyoScreen Hexyl are a rigid methacrylic polymer bead. GE HiScreen Butyl FF and HiScreen Octyl FF are high flow agarose based beads.

In one embodiment, the HIC media has a dynamic binding capacity of at least about 2 g, at least about 5 g, at least about 10 g, at least about 20 g, at least about 30 g, at least about 40 g, at least about 50 g, at least about 60 g, at least about 70 g, at least about 80 g, at least about 90 g, at least about 100 g, or at least about 200 g of sample per one liter of media.

Because the pH selected for any particular purification process must be compatible with protein stability and activity, particular pH conditions may be specific for each application. A high or low pH may serve to weaken hydrophobic interactions and retention of proteins changes.

The pH of the HIC purification process is dependent, in part, on the pH of the buffers used to load, equilibrate and or wash the chromatographic resin or media.

Accordingly, in one embodiment, the pH of any of the buffers is between about 4.0 and 8.5. In a further embodiment, the pH of any of the buffers is between about 5.0 and 7.0. In one embodiment, the pH of any of the buffers may be about 4.0, about 4.5, about 5.0, about 5.5, about 6.0, about 6.5, about 7.0, about 7.5, about 8.0, or about 8.5. In a preferred embodiment the pH of any of the buffers is 5.0. In a related embodiment the pH of any of the buffers is 5.6. In yet another embodiment, the pH of any of the buffers is 7.0.

In certain embodiments, the load challenge of the sample comprising the protein of interest and at least one impurity is adjusted to a total protein load to the column of between about 50 and 1000 g/L, or between about 250 and 700 g/L, or between about 350 and 500 g/L of HIC media. In certain embodiments, the protein concentration of the load challenge is adjusted to a total protein concentration of about 0.5 and 50 g/L, or between about 1 and 20 g/L, or between about 3 and 10 g/L. In one embodiment the load challenge is about 50 g, about 100 g, about 150 g, about 200 g, about 250 g, about 300 g, about 350 g, about 400 g, about 450 g, about 500 g, about 550 g, about 600 g, about 650 g, about 700 g, about 750 g, about 800 g, about 850 g, about 900 g, about 950 g, or about 1000 g of sample per one liter of HIC media. In a particular embodiment, the load challenge of the sample is 200 g/L. In another embodiment, the load challenge is 350 g/L. In yet another embodiment, load challenge of the sample is 500 g/L. In yet another embodiment, the load challenge of the sample is 700 g/L.

In another embodiment, the load challenge for the impurity alone is about 0.1 g, about 0.2 g, about 0.3 g, about 0.4 g, about 0.5 g, about 0.6 g, about 0.7 g, about 0.8 g, about 0.9 g, about 1.0 g, about 1.5 g, about 2.0 g, about 2.5 g, about 3.0 g, about 3.5 g, about 4.0 g, about 4.5 g, or about 5.0 g of the at least one impurity per one liter of HIC media.

In certain embodiments, impurity (e.g., aggregate) concentration is measured and used as a parameter for controlling impurity clearance in the present invention. For example, but not by way of limitation, the data presented in the Examples below, demonstrates that impurity concentration influences the impurity reduction by hydrophobic interaction chromatography. Thus, in certain embodiments, the at least one impurity concentration is adjusted from about 0.5 to 0.1 g/L, to about 0.1 to 0.05 g/L or to below 0.05 g/L. In another embodiment, the at least one impurity contacting the HIC media has a concentration of about 0.01, about 0.02, about 0.03, about 0.04, about 0.05, about 0.06, about 0.07, about 0.08, about 0.09, about 0.1, about 0.15, about 0.2, about 0.3, about 0.4, about 0.5, about 0.6, about 0.7, about 0.8, about 0.9, about 1.0, about 2.0, about 3.0, about 4.0 or about 5.0 g/L.

In certain embodiments, protein of interest concentration (e.g., antibody monomer) is measured and used as a parameter for controlling impurity (e.g., aggregate) clearance in the present invention. For example, but not by way of limitation, the data presented in the Examples below demonstrates that control of the concentration of the protein of interest can be used to achieve improved impurity clearance. Thus, in certain embodiments, the protein of interest concentration is adjusted from about 15 to 8 g/L, to about 8 to 4 g/L or to below 4 g/L. In another embodiment, the protein of interest contacting the HIC media has a concentration of less than about 1, about 2, about 3, about 4, about 5, about 6, about 7, about 8, about 9, about 10, about 15, about 20, about 25, about 30, about 35, about 40 about 45, about 50, or about 55 g/L.

In certain embodiments, protein of interest (e.g., antibody monomer) and impurity (e.g., aggregate) concentration is measured and used as a parameter for controlling impurity clearance in the present invention. For example, but not by way of limitation, the data presented in the Examples demonstrates that control of the protein of interest and monomer concentrations within certain ranges can be used to achieve improved impurity clearance. Thus, in certain embodiments, the protein of interest concentration is adjusted from about 20 to 15 g/L, about 15 to 8 g/L or to below 4 g/L and the impurity concentration is adjusted to 0.5 to 0.1 g/L, about 0.1 to 0.05 g/L or to below 0.05 g/L to achieve impurity reduction in the present invention. In another embodiment, the protein of interest contacting the HIC media has a concentration of about 1, about 2, about 3, about 4, about 5, about 6, about 7, about 8, about 9, about 10, about 15, about 20, about 25, about 30, about 35, about 40 about 45, or about 55 g/L and the at least one impurity contacting the HIC media has a concentration of less than about 0.01, about 0.02, about 0.03, about 0.04, about 0.05, about 0.06, about 0.07, about 0.08, about 0.09, about 0.1, about 0.15, about 0.2, about 0.3, about 0.4, about 0.5, about 0.6, about 0.7, about 0.8, about 0.9, or about 1.0 g/L.

In another embodiment, the sample contacting the HIC media has a concentration of about 1, about 2, about 3, about 4, about 5, about 6, about 7, about 8, about 9, about 10, about 15, about 20, about 25, about 30, about 35, about 40 about 45, or about 55 g/L.

In one embodiment, the at least one impurity is an aggregate of the protein of interest, for example, selected from the group consisting of a dimer, a trimer, a tetramer, an oligomer and other high molecular weight species. In a particular embodiment, the protein of interest is adalimumab and the at least one impurity is an aggregate of adalimumab. For example, the aggregate may be selected from the group consisting of multimer 1, multimer 2 and multimer 3.

In another embodiment, the impurity is a process-related impurity or a product-related substance. For example, the impurity may be a process-related impurity selected from the group consisting of a host cell protein, a host cell nucleic acid, a media component, and a chromatographic material. Alternatively, the impurity may be a product-related substance selected from the group consisting of a charge variant, an aggregate of the protein of interest, a fragment of the protein of interest and a modified protein.

In a particular embodiment the impurity is an acidic or basic variant, for example, of adalimumab. In a particular embodiment, the basic variant is a lysine variant species, for example, an antibody, or antigen-binding portion thereof, having heavy chains with either zero, one or two C-terminal lysines. In another embodiment, the impurity is an acidic species (AR), for example, selected from the group consisting of a charge variant, a structure variant, a fragmentation variant, a process-related impurity and a product-related impurity. In a particular embodiment, the acidic species is AR1 and the charge variant is a deamidation variant, a glycation variant, an afucosylation variant, a MGO variant and/or a citric acid variant. In another embodiment, the acidic species is AR1 and the structure variant is a glycosylation variant and/or an acetonation variant. In yet another embodiment, the acidic species is AR1 and the fragmentation variant is a Fab fragment variant, a C-terminal truncation variant or a variant missing a heavy chain variable domain. In yet a further embodiment, the acidic species is AR2 and the charge variant comprises a deamidation variant and/or glycation variant.

In a particular embodiment, the impurity is a fragment such as an Fc or a Fab fragment. In another embodiment, the impurity is a modified protein such as a deamidated protein or glycosylated protein.

In certain embodiments, HIC chromatographic fractions are collected during the load and/or wash cycles and are combined after appropriate analysis to provide a protein preparation that contains the reduced level of impurities. In certain embodiments, the flow through fraction is combined with certain wash fractions to improve the yield of the process while still achieving the desired, e.g., reduced level of impurities in the preparation.

Additionally, the flow through or wash fractions, or combination thereof may be contacted with HIC media again to further purify the sample. In various embodiments, the method may be repeated at least 1, 2, 3, 4, 5, 6, 7, 8, 9, 10, 15 or 20 times.

In certain embodiments, spectroscopy methods such as UV, NIR, FTIR, Fluorescence, Raman may be used to monitor levels of impurities such as aggregates and low molecular weight variants (e.g., fragments of the protein of interest) in an on-line, at-line or in-line mode, which can then be used to control the level of aggregates in the pooled material collected from the HIC methods of the present invention. In certain embodiments, on-line, at-line or in-line monitoring methods can be used either on the wash line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback, thereby facilitating product quality control.

In one embodiment, the reduced level of the at least one impurity of the flow through fractions and/or the wash fractions is at least about 60%, at least about 65%, at least about 70%, at least about 75%, at least about 80%, at least about 85%, at least about 90%, at least about 95%, at least about 98% or about 100% of the amount of the at least on impurity, e.g., aggregate or host cell protein in the sample.

In another embodiment, the impurity is a host cell protein and is reduced by at least 0.25, at least 0.5, at least 0.75, at least 1.0, at least 1.25, at least 1.5, at least 1.75, at least 2.0, or at least 5.0 LFR.

In another embodiment, the accumulative aggregate reduction of the at least one impurity in any one flow through fraction and/or wash fraction collected during the preparation is at least about 0.1%, at least about 0.2%, at least about 0.5%, at least about 1.0%, at least about 2.0%, at least about 3.0%, at least about 4.0%, at least about 5.0%, at least about 10%, at least about 20%, or at least about 50%.

In another embodiment, the accumulative aggregate reduction of the at least one impurity in the flow through fraction and the wash fractions is at least about 0.1%, at least about 0.2%, at least about 0.5%, at least about 1.0%, at least about 2.0%, at least about 3.0%, at least about 4.0%, at least about 5.0%, at least about 10.0%, or at least about 20.0%.

In another embodiment, the accumulative yield of the protein of interest in the flow through fraction and in the wash fraction is at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

In yet another embodiment, the accumulative yield of the protein of interest in any one flow through fraction or wash fraction is at least about 4%, at least about 10%, at least about 20%, at least about 30%, at least about 40%, at least about 50%, at least about 55%, at least about 60%, at least about 65%, at least about 70%, at least about 75%, at least about 80%, at least about 85, at least about 90%, at least about 95% or about 100%.

Complementary Purification Techniques

In certain embodiments, a combination of HIC and at least one of AEX (anion exchange chromatography) and CEX (cation exchange chromatography) and MM (mixed-mode chromatography) methods can be used to prepare preparations of protein of interest having a reduced level of impurity, including certain embodiments where one technology is used in a complementary/supplementary manner with another technology. In certain embodiments, such a combination can be performed such that certain sub-species are removed predominantly by a particularly technology, such that the combination provides the desired final composition/product quality. In certain embodiments, such combinations include the use of additional intervening chromatography, filtration, pH adjustment, UF/DF (ultrafiltration/diafiltration) steps so as to achieve the desired product quality, ion concentration, and/or viral reduction.

Affinity Chromatography

In certain embodiments, a precursor sample is subjected to affinity chromatography to purify the protein of interest, prior to the methods of the present invention. Alternatively or in addition, the wash and/or flow through fractions generated by the methods of the present invention can be subjected to affinity chromatography to further purify the protein of interest. As noted above, certain embodiments of the present invention will employ one or more affinity chromatography steps prior to the HIC purification step, while others will employ an affinity chromatography step after or both before and after the HIC purification step. In certain embodiments, the affinity chromatography media is a Protein A, G, A/G, or L media, although alternative affinity chromatography medias are known in the art. There are a variety of commercial sources for Protein A media. Suitable medias include, but are not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies.

In certain embodiments, the Protein A column can be equilibrated with a suitable buffer prior to sample loading. Following the loading of the column, the column can be washed one or multiple times using a suitable sets of buffers. The Protein A column can then be eluted using an appropriate elution buffer. The eluate can be monitored using techniques well known to those skilled in the art. The eluate fractions of interest can be collected and then prepared for further processing.

The Protein A eluate may be subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but are not limited to, Millistak+X0HC, F0HC, D0HC, A 1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

Ion Exchange Chromatography

In certain embodiments, a precursor sample is subjected to ion exchange chromatography to purify the protein of interest, prior to the methods of the present invention. Alternatively or in addition, the wash and/or flow through fractions generated by the methods of the present invention can be subjected to ion exchange chromatography to further purify the protein of interest. As noted above, certain embodiments of the present invention will employ one or more ion exchange chromatography steps prior to the HIC purification step, while others will employ an ion exchange chromatography step after or both before and after the HIC purification step.

As used herein, ion exchange separations includes any method by which two substances are separated based on the difference in their respective ionic charges, either on the protein of interest and/or chromatographic material as a whole or locally on specific regions of the protein of interest and/or chromatographic material, and thus can employ either cationic exchange material or anionic exchange material.

The use of a cationic exchange material versus an anionic exchange material is based on the local charges of the protein of interest in a given solution. Therefore, it is within the scope of this invention to employ an anionic exchange step prior to the use of a HIC step, or a cationic exchange step prior to the use of an HIC step. Furthermore, it is within the scope of this invention to employ only a cationic exchange step, only an anionic exchange step, or any serial combination of the two either prior to or subsequent to the HIC step.

In performing the separation, the sample containing the protein of interest (e.g., an antibody or antigen-binding fragment thereof) can be contacted with the ion exchange material by using any of a variety of techniques, e.g., using a batch purification technique or a chromatographic technique, as described above in connection with HIC.

Ion exchange chromatography separates molecules based on differences between the local charges of the proteins of interest and the local charges of the chromatographic material. A packed ion-exchange chromatography column or an ion-exchange membrane device can be operated in a bind-elute mode, a flow-through, or a hybrid mode. After washing the column or the membrane device with the equilibration buffer or another buffer with different pH and/or conductivity, the product recovery is achieved by increasing the ionic strength (i.e., conductivity) of the elution buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). The column is then regenerated before next use.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange medias such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNOSphere™ S from BioRad, Hercules, Calif., Eshmuno® S from EMD Millipore, Billerica, Calif.

Mixed Mode Chromatography

In certain embodiments, a precursor sample is subjected to mixed mode chromatography to purify the protein of interest, prior to the HIC methods of the present invention. Alternatively or in addition, the wash and/or flow through fractions generated by the methods of the present invention can be subjected to mixed mode chromatography to further purify the protein of interest. As noted above, certain embodiments of the present invention will employ one or more mixed mode chromatography steps prior to the HIC purification step, while others will employ a mixed mode chromatography step after or both before and after the HIC purification step.

Mixed mode chromatography is chromatography that utilizes a mixed mode media, such as, but not limited to CaptoAdhere available from GE Healthcare. Such a media comprises a mixed mode chromatography ligand. In certain embodiments, such a ligand refers to a ligand that is capable of providing at least two different, but co-operative, sites which interact with the substance to be bound. One of these sites gives an attractive type of charge-charge interaction between the ligand and the protein of interest. The other site typically gives electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. The mixed mode functionality can give a different selectivity compared to traditional anion exchangers. For example, CaptoAdhere is designed for post-Protein A purification of monoclonal antibodies, where removal of leached Protein A, aggregates, host cell proteins, nucleic acids and viruses from monoclonal antibodies is performed in flow-through mode (the antibodies pass directly through the column while the contaminants are adsorbed). Mixed mode chromatography ligands are also known as "multimodal" chromatography ligands.

In certain embodiments, the mixed mode chromatography media is comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

Viral Filtration

In certain embodiments, a precursor sample is subjected to viral filtration to purify the protein of interest, prior to the HIC methods of the present invention. Alternatively or in addition, the wash and/or flow through fractions generated by the methods of the present invention can be subjected to viral filtration to further purify the protein of interest. As noted above, certain embodiments of the present invention will employ one or more viral filtration steps prior to the HIC purification step, while others will employ viral filtration after or both before and after the HIC purification step.

Viral filtration is a dedicated viral reduction step in the entire purification process. This step is usually performed as a post chromatographic polishing step. Viral reduction can be achieved via the use of suitable filters including, but not limited to, Planova 20N™, 50 N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

Ultrafiltration/Diafiltration

In certain embodiments, a precursor sample is subjected to ultrafiltration and/or diafiltration to purify the protein of interest, prior to the HIC methods of the present invention. Alternatively or in addition, the wash and/or flow through fractions generated by the methods of the present invention can be subjected to ultrafiltration and/or diafiltration to further purify the protein of interest. As noted above, certain embodiments of the present invention will employ one or more ultrafiltration and/or diafiltration steps prior to the HIC purification step, while others will employ ultrafiltration and/or diafiltration after or both before and after the HIC purification step.

Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultrafiltration rate. This washes microspecies from the solution at a constant volume, effectively purifying the retained antibody. In certain embodiments of the present invention, a diafiltration step is employed to exchange the various buffers used in connection with the instant invention, optionally prior to further chromatography or other purification steps, as well as to remove impurities from the antibody preparations.

Exemplary Purification Strategies

In certain embodiments, primary recovery can proceed by sequentially employing pH reduction, centrifugation, and filtration steps to remove cells and cell debris (including HCPs) from the production bioreactor harvest.

Additionally, the HIC methodology as described herein is utilized to further purify the protein of interest. As set forth herein, such methods involve (a) contacting a sample including the protein of interest and at least one impurity, to a hydrophobic interaction chromatography (HIC) media, in the presence of a load buffer such that (i) a portion of the protein of interest binds to the HIC media, for example, at a Kp of at least 10, 20 or 100 and (ii) a substantial portion of the at least one impurity binds to the HIC media; (b) collecting a flow through fraction including the protein of interest unbound to the HIC media; (c) washing the HIC media with a wash buffer that is substantially the same as the load buffer such that a substantial portion of the protein of interest bound to the HIC media is released from the media; and (d) collecting a wash fraction including the protein of interest released from the HIC media, wherein each of the flow through and wash fractions include the protein of interest and have a reduced level of the at least one impurity.

Examples of buffers that can be used in the context of both the loading and wash steps of the present invention include, but are not limited to, the following: about 0.1 M to about 0.6 M sodium citrate (NaCit), pH 5.6; or about 0.5 M to about 1.1 M ammonium sulfate ($AmSO_4$), pH 7.0 as well as buffers substantially the same, in that any differences result in insubstantial changes to the binding of impurities, but do not substantially affect the ability to wash and release antibody product. Such buffers can span a range of varying "hydrophobicities" based on the rationales discussed in above.

In certain embodiments, the HIC media employed in the HIC step is CaptoPhenyl (GE) resin. In certain embodiments, the CaptoPhenyl (GE) resin is buffer exchanged into 0.4 M sodium citrate (NaCit), pH 5.6, and then distributed in 100 □L aliquots into microcentrifuge tubes. Each tube is then challenged with 2 mL of antibody produce source material, e.g., a partially purified cell culture harvest sample, in 0.4 M NaCit, pH 5.6, at a range of concentrations from 0.5-15.0 mg/mL and incubated for 3 hours at room temperature with mixing. The resin is allowed to settle and the supernatant removed and replaced with 1 mL of fresh 0.4 M NaCit, pH 5.6, buffer and incubated for 2 hours at room temperature with mixing. This step was repeated one more time.

In alternative embodiments, the CaptoPhenyl (GE) HIC resin can be packed in 1.0 cm×10.0 cm (OmniFit) columns. Antibody product HIC-load can be prepared by diluting the source material, e.g., a partially purified cell culture harvest sample, with a 1.2 M stock solution of sodium citrate (NaCit), pH 5.6, to final concentration in the range of 0.3 to 0.5 M NaCit, pH 5.6. CaptoPhenyl columns can then be equilibrated with 7 column volumes (CVs) of a NaCit buffer, pH 5.6, corresponding to the load concentration. The antibody product solution can then be loaded to the column in the range of 200-500 g/L, after which the column is washed with 20 CVs of the wash buffer. The column can then be regenerated (3 CVs f 25 mM sodium phosphate/20% (v/v) isopropyl alcohol, pH 6.5), cleaned in place (3 CVs 1M NaOH, 60 min hold), and stored (5 CVs of 25 mM sodium phosphate/20% (v/v) isopropyl alcohol, pH 6.5). The released solution from the column can be fractionated during the entire run and used to monitor the breakthrough of both the protein of interest, e.g., antibody product monomer, as well as impurities, e.g., aggregates and host cell protein (HCP).

Such HIC purification steps can be preceded by affinity chromatography, for example, but not limited to, the use of Protein A-base affinity chromatography. There are several commercial sources for Protein A media. One suitable media is MabSelect™ from GE Healthcare. An example of a suitable column packed with MabSelect™ is a column about 1.0 cm diameter×about 21.6 cm long (~17 mL bed volume). This size column can be used for bench scale. This can be compared with other columns used for scale ups. For example, a 20 cm×21 cm column whose bed volume is about 6.6 L can be used for commercial production. Regardless of the column, the column can be packed using a suitable media such as MabSelect™.

In certain aspects, the Protein A column can be equilibrated with a suitable buffer prior to sample loading. An example of a suitable buffer is a Tris/NaCl buffer, pH of about 6 to 8, and in certain embodiments about 7.2. A specific example of suitable conditions is 25 mM Tris, 100 mM NaCl, pH 7.2. Following this equilibration, the sample can be loaded onto the column. Following the loading of the column, the column can be washed one or multiple times using, e.g., the equilibrating buffer. Other washes including washes employing different buffers can be used before eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. An example of a suitable elution buffer is an acetic acid/NaCl buffer, pH around 3.5. Suitable conditions are, e.g., 0.1 M acetic acid, pH 3.5. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

In certain embodiments, the HIC purification step can also be preceded by an ion exchange chromatography step. The ion exchange purification step can occur before, after, or in place of an affinity chromatography step. In certain embodiments, where a Protein A step precedes the ion exchange step, a Protein A eluate is purified using a cation exchange column. In certain embodiments, the equilibrating buffer used in the cation exchange column is a buffer having a pH of about 5.0. An example of a suitable buffer is about 210 mM sodium acetate, pH 5.0. Following equilibration, the column is loaded with sample prepared from HIC purification step above. The column is packed with a cation exchange media, such as CM Sepharose™ Fast Flow from GE Healthcare. The column is then washed using the equilibrating buffer. The column is next subjected to an elution step using a buffer having a greater ionic strength as compared to the equilibrating or wash buffer. For example, a suitable elution buffer can be about 790 mM sodium acetate, pH 5.0. The antibodies will be eluted and can be monitored using a UV spectrophotometer set at $OD_{280nm}$. In a particular example, elution collection can be from upside 3 $OD_{280nm}$ to downside 8 $OD_{280nm}$. It should be understood that one skilled in the art may vary the conditions and yet still be within the scope of the invention.

In certain embodiments where a Protein A step precedes an ion exchange step, a Protein A eluate is purified using an anion exchange column. A non-limiting example of a suitable column for this step is a 60 cm diameter×30 cm long column whose bed volume is about 85 L. The column is packed with an anion exchange media, such as Q Sepharose™ Fast Flow from GE Healthcare. The column can be equilibrated using about seven column volumes of an appropriate buffer such as Tris/sodium chloride. An example of suitable conditions is 25 mM Tris, 50 mM sodium chloride at pH 8.0. A skilled artisan may vary the conditions but still be within the scope of the present invention. The column is loaded with the collected sample from the HIC purification step outlined above. In another aspect, the column is loaded from the eluate collected during cation exchange. Following the loading of the column, the column is washed with the equilibration buffer (e.g., the Tris/sodium chloride buffer). The flow-through comprising the antibodies can be monitored using a UV spectrophotometer at $OD_{280nm}$. This anion exchange step reduces process related impurities such as nucleic acids like DNA, and host cell proteins. The separation occurs due to the fact that the antibodies of interest do not substantially interact with nor bind to the solid phase of the column, e.g., to the Q Sepharose™, but many impurities do interact with and bind to the column's solid phase. The anion exchange can be performed at about 12° C.

In certain embodiments, the cation exchange or anion exchange eluate, depending on which ion exchange step is employed, or employed first, is next filtered using, e.g., a 16 inch Cuno™ delipid filter. This filtration, using the delipid filter, can be followed by, e.g., a 30-inch 0.45/0.2 µm Sartopore™ bi-layer filter cartridge. The ion exchange elution buffer can be used to flush the residual volume remaining in the filters and prepared for ultrafiltration/diafiltration.

In order to accomplish the ultratfiltration/diafiltration step, the filtration media is prepared in a suitable buffer, e.g., 20 mM sodium phosphate, pH 7.0. A salt such as sodium chloride can be added to increase the ionic strength, e.g., 100 mM sodium chloride. This ultrafiltration/diafiltration step serves to concentrate the anti-IL-12, anti-TNFα, or anti-IL-18 antibodies, remove the sodium acetate and adjust the pH. Commercial filters are available to effectuate this step. For example, Millipore manufactures a 30 kD molecular weight cut-off (MWCO) cellulose ultrafilter membrane cassette. This filtration procedure can be conducted at or around room temperature.

In certain embodiments, the sample from the capture filtration step above is subjected to a second ion exchange separation step. In certain embodiments, this second ion exchange separation will involve separation based on the opposite charge of the first ion exchange separation. For example, if an anion exchange step is employed after HIC purification, the second ion exchange chromatographic step may be a cation exchange step. Conversely, if the HIC purification step was followed by a cation exchange step, that step would be followed by an anion exchange step. In certain embodiments the first ion exchange eluate can be subjected directly to the second ion exchange chromatographic step where the first ion exchange eluate is adjusted to the appropriate buffer conditions. Suitable anionic and cationic separation materials and conditions are described above.

In certain embodiments, a mixed mode chromatography step will precede the HIC chromatography step, thereby forming a mixed mode chromatography sample that can be exposed to the HIC media in the HIC chromatography step. Examples of mixed mode medias include, but are not limited to: CaptoAdhere (GE Healthcare), PPA-HyperCel (Pall Life Sciences), and HEA-HyperCel (Pall Life Sciences). In certain embodiments, the mixed mode chromatography step is a CaptoAdhere chromatography step. In certain embodiments, the mixed mode chromatography sample is further subject to a filtration step. Filters well known to those skilled in the art can be used in this embodiment. In one aspect, the filtration step is a nanofiltration step. In certain embodiments, a depth filtration step follows a filtration step.

In certain embodiments of the invention, the wash and/or flow through fractions from the hydrophobic chromatography step are subjected to filtration for the removal of viral particles, including intact viruses, if present. A non-limiting example of a suitable filter is the Ultipor DV50™ filter from Pall Corporation. Other viral filters can be used in this filtration step and are well known to those skilled in the art. The HIC eluate is passed through a pre-wetted filter of about 0.1 µm and a 2×30-inch Ultipor DV50™ filter train at around 34 psig. In certain embodiments, following the filtration process, the filter is washed using, e.g., the HIC wash buffer in order to remove any antibodies retained in the filter housing. The filtrate can be stored in a pre-sterilized container at around 12° C.

In a certain embodiments, the filtrate from the above is again subjected to ultrafiltration/diafiltration. This step is important if a practitioner's end point is to use the antibody in a, e.g., pharmaceutical formulation. This process, if employed, can facilitate the concentration of antibody, removal of buffering salts previously used and replace it with a particular formulation buffer. In certain embodiments, continuous diafiltration with multiple volumes, e.g., two volumes, of a formulation buffer is performed. A non-limiting example of a suitable formulation buffer is 5 mM methionine, 2% mannitol, 0.5% sucrose, pH 5.9 buffer (no Tween). Upon completion of this diavolume exchange the antibodies are concentrated. Once a predetermined concentration of antibody has been achieved, then a practitioner can calculate the amount of 10% Tween that should be added to arrive at a final Tween concentration of about 0.005% (v/v).

Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™ further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

In certain embodiments the unbound flow through and wash fractions can be further fractionated and a combination of fractions providing a target protein of interest purity can be pooled.

In certain embodiments the protein concentration can be adjusted to achieve a differential partitioning behavior between the protein of interest and the impurities such that the purity and/or yield can be further improved.

In certain embodiments the loading can be performed at different protein concentrations during the loading operation to improve the product quality/yield of any particular purification step.

In certain embodiments the column temperature, can be independently varied to improve the separation efficiency and/or yield of any particular purification step.

In certain embodiments, the loading and washing buffers can be different or composed of mixtures of chemicals, while achieving similar "hydrophobic interaction" behavior such that the above novel separation can be effected.

In certain embodiments, the loading and washing buffers can be different, in terms of ionic strength or pH, while remaining substantially the same in function in terms of the washout of the protein of interest achieved during the wash step.

In certain embodiments, the loading & washing steps can be controlled by in-line, at-line or off-line measurement of the impurity levels, either in the column effluent, or the collected pool or both, so as to achieve the protein of interest quality and/or yield.

In certain embodiments, the loading concentration can be dynamically controlled by in-line or batch or continuous dilutions with buffers or other solutions to achieve the partitioning necessary to improve the separation efficiency and/or yield.

In certain embodiments, additives such as amino acids, sugars, PEG, etc can be added to the load or wash steps to modulate the partitioning behavior to achieve the separation efficiency and/or yield.

In certain embodiments, the separation can be performed on any type of HIC media such as membranes, monoliths or depth filters that have hydrophobic interaction characteristics.

Mixed mode media can also be employed to enable this method, provided the same functionality is achieved by appropriately adjusting the column loading and/or washing conditions.

Methods of Assaying Sample Purity
Assaying Aggregates

In certain embodiments, the levels of product-related substances, such as aggregates, in either the initial sample or the flow through and/or wash fractions following the HIC steps of the present invention are analyzed. For example, but not by way of limitation, the aggregates present in the Adalimumab process samples can be quantified according to the following methods.

Aggregates may be measured using a size exclusion chromatographic (SEC) method whereby molecules are separated based on size and/or molecular weight such that larger molecules elute earlier from the column. For example, but not by way of limitation, a SEC columns useful for the detection of aggregates include: TSK-gel G3000SWxL, 5 µm, 125 Å, 7.8×300 mm column (Tosoh Bioscience), TSK-gel Super SW3000, 4 µm, 250 Å, 4.6×300 mm column (Tosoh Bioscience), or Zorbax GF450 column (Agilent Technologies). A further example of an SEC column for analysis of monomers and aggregates is the MAbPac™ SEC-1 (Thermo Scientific) column which may be used under non-denaturing conditions, in both high- and low-salt mobile phases, and with volatile eluents. In certain embodiments, the aforementioned columns are used along with an Agilent or a Shimazhu HPLC system. In a particular embodiment of SEC, aggregates may be quantified using a Zorbax GF450 column on an Agilent HPLC system.

In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm.

The elution profile may be further analyzed using multi-angle laser light-scattering (MALS), to determine the apparent molecular weight of each peak, and allow identification as a dimer, tetramer, or other high molecular weight species (FIG. 1). The elution profile may also be further analyzed using sodium dodecyl sulfate-polyacrylamide gel electrophoresis (SDS-PAGE). For example, the fraction is mixed with either a non-reducing or reducing denaturing sample buffer, treated for two minutes at 98° C. in an Eppendorf Thermomixer Confort, then loaded in a 5% polyacrylamide tris-HCL gel alongside pre-stained broad range molecular weight markers. Electrophoresis is performed using a buffer comprising 0.3% (w/v) Tris, 1.44% (w/v) glycine and 0.1% SDS, pH 8.3. Separation is performed at a constant current of 100 V and at maximally 50 mA for about 1 hour, followed by staining of the gel. In another embodiment, the aggregates may be analyzed and the molecular weight determined using high performance-size exclusion chromatography followed by native electrospray ionization time-of-flight mass spectrometry (ESI-TOF MS). Further methods for assaying levels of aggregates are provided in the Examples below.

Assaying Host Cell Protein

The present invention also provides methods for determining the residual levels of host cell protein (HCP) concentration in the initial sample or the flow through and/or wash fractions following the HIC steps of the present invention. As described above, HCPs are desirably excluded from the final preparation. Exemplary HCPs include proteins originating from the source of the protein of interest production. Failure to identify and sufficiently remove HCPs from the target protein of interest may lead to reduced efficacy and/or adverse subject reactions when administered in a therapeutic setting.

As used herein, the term "HCP ELISA" refers to an ELISA where the antibody used in the assay is specific to the HCPs produced from cells, e.g., CHO cells, used to generate the protein of interest. The antibody may be produced according to conventional methods known to those of skill in the art. For example, the antibody may be produced using HCPs obtained by sham production and purification runs, i.e., the same cell line used to produce the protein of interest is used, but the cell line is not transfected with antibody DNA. In an exemplary embodiment, the antibody is produced using HPCs similar to those expressed in the cell expression system of choice, i.e., the cell expression system used to produce the protein of interest.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments, the first and second antibodies are polyclonal antibodies. In certain embodiments, the first and second antibodies are blends of polyclonal antibodies raised against HCPs. The amount of HCP contained in the sample is determined using the appropriate test based on the label of the second antibody.

HCP ELISA may be used for determining the level of HCPs in preparation or fraction, such as a wash fraction or a flow-through obtained using the process described above. The present invention also provides a preparation comprising a protein of interest, wherein the composition has no detectable level of HCPs as determined by an HCP Enzyme Linked Immunosorbent Assay ("ELISA"). In one embodiment, the protein of interest is adalimumab.

Assaying Charge and Size Variants

In certain embodiments, the levels of product-related substances, such as acidic species and other charge variants, in the chromatographic samples produced using the techniques described herein are analyzed. For example, but not by way of limitation, the acidic species and other charge variants present in the Adalimumab process samples can be quantified according to the following methods. Cation exchange chromatography was performed on a Dionex ProPac WCX-10, Analytical column 4 mm×250 mm (Dionex, CA). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

In certain embodiments, the levels of aggregates, monomer, and fragments in the chromatographic samples produced using the techniques described herein are analyzed. In certain embodiments, the aggregates, monomer, and fragments are measured using a size exclusion chromatographic (SEC) method for each molecule. For example, but not by way of limitation, a TSK-gel G3000SWxL, 5 µm, 125 Å, 7.8×300 mm column (Tosoh Bioscience) can be used in connection with certain embodiments, while a TSK-gel Super SW3000, 4 µm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

Antibody Generation

Antibodies to be purified by the methods of the present invention can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

In certain embodiments, the animal system for preparing hybridomas is the murine system. Hybridoma production is a well-established procedure. Immunization protocols and techniques for isolation of immunized splenocytes for fusion are known in the art. Fusion partners (e.g., murine myeloma cells) and fusion procedures are also known.

An antibody can be, in certain embodiments, a human, a chimeric, or a humanized antibody. Humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and U.S. Pat. No. 6,180,370 to Queen et al.).

Human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise the antibodies of this disclosure.

In certain embodiments, the antibodies of this disclosure are recombinant human antibodies, which can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies or antigen-binding portions thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173: 1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767, 704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to the antigen to which the putative antibody of interest binds. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the one to which the putative antibody of interest binds, depending on the specificity of the antibody of the invention, by crosslinking an antibody of the invention to a second antibody by standard chemical crosslinking methods.

In a suitable system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

Methods of Treatment Using the Low Impurity Compositions of the Invention

The low impurity compositions, for example, low aggregate compositions, of the invention may be used to treat any disorder in a subject for which the therapeutic protein of interest (e.g., an antibody or an antigen binding portion thereof) comprised in the composition is appropriate for treating.

A "disorder" is any condition that would benefit from treatment with the protein of interest. This includes chronic and acute disorders or diseases including those pathological conditions which predispose the subject to the disorder in question. In the case of an anti-TNFα antibody, or antigen binding portion thereof, such as adalimumab, a therapeutically effective amount of the low impurity composition may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the low impurity compositions of the invention may be used to treat an autoimmune disease, such as rheumatoid arthritis, juvenile idiopathic arthritis, or psoriatic arthritis, an intestinal disorder, such as Crohn's disease or ulcerative colitis, a spondyloarthropathy, such as ankylosing spondylitis, or a skin disorder, such as psoriasis.

Disorders in which TNFα activity is detrimental are well known in the art and described in detail in U.S. Pat. No. 8,231,876 and U.S. Pat. No. 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina, and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, cardiomyopathy, coronary artery spasm, coronary artery disease, valvular disease, arrhythmias, and cardiomyopathies), spondyloarthropathies (including ankylosing spondylitis, psoriatic arthritis/spondylitis, enteropathic arthritis, reactive arthritis or Reiter's syndrome, and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis), hepatic disorders (including hepatitis, alcoholic hepatitis, viral hepatitis, alcoholic cirrhosis, a1 antitypsin deficiency, autoimmune cirrhosis, cryptogenic cirrhosis, fulminant hepatitis, hepatitis B and C, and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), pemphigus vulgaris, scleroderma, atopic dermatitis (eczema), sarcoidosis, erythema nodosum, hidradenitis suppurativa, lichen planus, Sweet's syndrome, scleroderma and vitiligo), vasculitides (including Behcet's disease), and other disorders, such as juvenile rheumatoid arthritis (JRA), endometriosis, prostatitis, choroidal neovascularization, sciatica, Sjogren's syndrome, uveitis, wet macular degeneration, osteoporosis and osteoarthritis.

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering a low impurity composition comprising an anti-TNFα antibody, or antigen binding portion thereof, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab, also referred to as HUMIRA®.

The low impurity compositions can be administered by a variety of methods known in the art. Exemplary routes/modes of administration include subcutaneous injection, intravenous injection or infusion. In certain aspects, a low impurity compositions may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a low impurity composition of the invention is 0.01-20 mg/kg, or 1-10 mg/kg, or 0.3-1 mg/kg. With respect to low impurity compositions comprising an anti-TNFα antibody, or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg, and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Pharmaceutical Formulations Containing the Low Impurity Compositions of the Invention The present invention further provides preparations and formulations comprising low impurity compositions, for example, low aggregate compositions, of the invention. It should be understood that any of the proteins of interest, such as antibodies and antibody fragments described herein, including proteins of interest having any one or more of the structural and functional features described in detail throughout the application, may be formulated or prepared as described below. When various formulations are described in this section as including a protein of interest, such as an antibody, it is understood that such a protein of interest may be a protein having any one or more of the characteristics of the proteins of interest described herein. In one embodiment, the antibody is an anti-TNFα antibody, or antigen-binding portion thereof.

In certain embodiments, the low impurity compositions, for example, low aggregate compositions, of the invention may be formulated with a pharmaceutically acceptable carrier as pharmaceutical (therapeutic) compositions, and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the proteins of interest (e.g., antibodies) of the present invention, and with each other, in a manner such that there is no interaction which would substantially impair the desired pharmaceutical efficacy.

The low impurity compositions, for example, low aggregate compositions, of the invention are present in a form known in the art and acceptable for therapeutic uses. In one embodiment, a formulation of the low impurity compositions, for example, low aggregate compositions, of the invention is a liquid formulation. In another embodiment, a formulation of the low impurity compositions, for example, low aggregate compositions, of the invention is a lyophilized formulation. In a further embodiment, a formulation of the low impurity compositions, for example, low aggregate compositions, of the invention is a reconstituted liquid formulation. In one embodiment, a formulation of the low impurity compositions, for example, low aggregate compositions, of the invention is a stable liquid formulation. In one embodiment, a liquid formulation of the low impurity compositions, for example, low aggregate compositions, of the invention is an aqueous formulation. In another embodiment, the liquid formulation is non-aqueous. In a specific embodiment, a liquid formulation of the low impurity compositions, for example, low aggregate compositions, of the invention is an aqueous formulation wherein the aqueous carrier is distilled water.

The formulations of the low impurity compositions, for example, low aggregate compositions, of the invention comprise a protein of interest (e.g., an antibody) in a concentration resulting in a w/v appropriate for a desired dose. The protein of interest may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In a specific embodiment, a formulation of the low impurity compositions, for example, low aggregate compositions, of the invention comprises at least about 100 mg/ml, at least about 125 mg/ml, at least 130 mg/ml, or at least about 150 mg/ml of protein of interest (e.g., an antibody) of the invention.

In one embodiment, the concentration of protein of interest (e.g., antibody), which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml, or between about 25 mg/ml and about 50 mg/ml.

In a specific embodiment, a formulation of the low impurity compositions, for example, low aggregate compositions, of the invention comprises between about 90 mg/ml and about 110 mg/ml or between about 100 mg/ml and about 210 mg/ml of a protein of interest (e.g., an antibody).

The formulations of the low impurity compositions, for example, low aggregate compositions, of the invention comprising a protein of interest (e.g., an antibody) may further comprise one or more active compounds as necessary for the particular indication being treated, typically those with complementary activities that do not adversely affect each other. Such additional active compounds are suitably present in combination in amounts that are effective for the purpose intended.

The formulations of the low impurity compositions, for example, low aggregate compositions, of the invention may be prepared for storage by mixing the protein of interest (e.g., antibody) having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12$^{th}$ edition, L. Brunton, et al. and *Remington's Pharmaceutical Sciences*, 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, $MgCl_2$, or $CaCl_2$ The formulations of the low impurity compositions, for example, low aggregate compositions, of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0. One of skill in the art understands that the pH of a formulation generally should not be equal to the isoelectric point of the particular protein of interest (e.g., antibody) to be used in the formulation.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the low impurity compositions, for example, low aggregate compositions, of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a formulation may comprise about 10 mM, about 25 mM, or no histidine.

The formulations of the low impurity compositions, for example, low aggregate compositions, of the invention may comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In a specific embodiment, the formulations of the low impurity compositions, for example, low aggregate compositions, of the invention may comprise trehalose. In one embodiment, a formulation of the invention comprises at least about 1%, at least about 2%, at least about 4%, at least about 8%, at least about 20%, at least about 30%, or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a formulation of the invention comprises about 1%, about 2%, about 4%, about 6%, about 8%, about 15%, about 20%, about 30%, or about 40% trehalose. In a specific embodiment, a formulation of the invention comprises about 4%, about 6% or about 15% trehalose.

In certain embodiments, a formulation of the low impurity compositions, for example, low aggregate compositions, of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, $CaCl_2$, and $MgCl_2$. In a specific embodiment, the formulation comprises NaCl.

A formulation of the low impurity compositions, for example, low aggregate compositions, of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM, or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM, or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM, or about 300 mM sodium chloride.

A formulation of the low impurity compositions, for example, low aggregate compositions, of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM, or about 400 mM of an amino acid.

The formulations of the low impurity compositions, for example, low aggregate compositions, of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc.), can optionally be added to the formulations of the invention to reduce aggregation. In one embodiment, a formulation of the invention comprises Polysorbate 20, Polysorbate 40, Polysorbate 60, or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

The formulations of the low impurity compositions, for example, low aggregate compositions, of the invention may optionally further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of protein of interest (e.g., an antibody), as well known those in the art or as described herein.

In one embodiment, the low impurity compositions, for example, low aggregate compositions, of the invention are formulated with the same or similar excipients and buffers as are present in the commercial adalimumab (HUMIRA®) formulation, as described in the "Highlights of Prescribing Information" for HUMIRA® (adalimumab) Injection (Revised January 2008) the contents of which are hereby incorporated herein by reference. For example, each prefilled syringe of HUMIRA®, which is administered subcutaneously, delivers 0.8 mL (40 mg) of drug product to the subject. Each 0.8 mL of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for Injection, USP. Sodium hydroxide is added as necessary to adjust pH.

It will be understood by one skilled in the art that the formulations of the low impurity compositions, for example, low aggregate compositions, of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonicity of the formulation. Tonicity modifiers suitable for this invention include, but are not limited to, saccharides, salts and amino acids.

In certain embodiments, the formulations of the low impurity compositions, for example, low aggregate compositions, of the invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

The concentration of any one component or any combination of various components, of the formulations of the low impurity compositions, for example, low aggregate compositions, of the invention is adjusted to achieve the desired tonicity of the final formulation. For example, the ratio of the carbohydrate excipient to protein of interest (e.g., antibody) may be adjusted according to methods known in the art (e.g., U.S. Pat. No. 6,685,940). In certain embodiments, the molar ratio of the carbohydrate excipient to protein of interest (e.g., antibody) may be from about 100 moles to about 1000 moles of carbohydrate excipient to about 1 mole of protein of interest, or from about 200 moles to about 6000 moles of carbohydrate excipient to about 1 mole of protein of interest, or from about 100 moles to about 510 moles of carbohydrate excipient to about 1 mole of protein of interest, or from about 100 moles to about 600 moles of carbohydrate excipient to about 1 mole of protein of interest.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate, and calcium chloride. In specific embodiments, formulations of the invention comprise NaCl, $MgCl_2$, and/or $CaCl_2$. In one embodiment, concentration of NaCl is between about 75 mM and about 150 mM. In another embodiment, concentration of $MgCl_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine, and histidine.

In one embodiment the formulations of the low impurity compositions, for example, low aggregate compositions, of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the low impurity compositions, for example, low aggregate compositions, of the invention should be sterile. The formulations of the invention may be sterilized by various sterilization methods, including sterile filtration, radiation, etc. In one embodiment, the protein of interest (e.g., antibody) formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising proteins of interest (e.g., antibodies), such as those disclosed herein, ordinarily will be stored in lyophilized form or in solution. It is contemplated that sterile compositions comprising proteins of interest (e.g., antibodies) are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the low impurity compositions, for example, low aggregate compositions, of the invention is a lyophilized formulation. The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein of interest (such as an antibody of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS™; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and protein of interest (e.g., antibody) molecules of a formulation of the invention is at least about 10, at least about 50, at least about 100, at least about 200, or at least about 300. In another embodiment, the molar ratio of a lyoprotectant (e.g., trehalose) and protein of interest molecules of a formulation of the invention is about 1, is about 2, is about 5, is about 10, about 50, about 100, about 200, or about 300.

A "reconstituted" formulation is one which has been prepared by dissolving a lyophilized protein of interest (e.g., antibody) formulation in a diluent such that the protein of interest is dispersed in the reconstituted formulation. The reconstituted formulation is suitable for administration (e.g., parenteral administration) to a patient to be treated with the protein of interest and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the low impurity compositions, for example, low aggregate compositions, of the invention is a lyophilized formulation comprising a protein of interest (e.g., antibody) of the invention, wherein at least about 90%, at least about 95%, at least about 97%, at least about 98%, or at least about 99% of said protein of interest may be recovered from a vial upon shaking said vial for 4 hours at a speed of 400 shakes per minute wherein the vial is filled to half of its volume with the formulation. In another embodiment, a formulation of the invention is a lyophilized formulation comprising a protein of interest of the invention, wherein at least about 90%, at least about 95%, at least about 97%, at least about 98%, or at least about 99% of the protein of interest may be recovered from a vial upon subjecting the formulation to three freeze/thaw cycles wherein the vial is filled to half of its volume with said formulation. In a further embodiment, a formulation of the invention is a lyophilized formulation comprising a protein of interest of the invention, wherein at least about 90%, at least about 95%, at least about 97%, at least about 98%, or at least about 99% of the protein of interest may be recovered by reconstituting a lyophilized cake generated from said formulation.

In one embodiment, a reconstituted liquid formulation may comprise a protein of interest (e.g., antibody) at the same concentration as the pre-lyophilized liquid formulation.

In another embodiment, a reconstituted liquid formulation may comprise a protein of interest (e.g., antibody) at a higher concentration than the pre-lyophilized liquid formulation, e.g., about 2 fold, about 3 fold, about 4 fold, about 5 fold, about 6 fold, about 7 fold, about 8 fold, about 9 fold, or about 10 fold higher concentration of a protein of interest than the pre-lyophilized liquid formulation.

In yet another embodiment, a reconstituted liquid formulation may comprise a protein of interest (e.g., antibody) of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of a protein of interest than the pre-lyophilized liquid formulation.

The pharmaceutical formulations of the low impurity compositions, for example, low aggregate compositions, of the invention are typically stable formulations, e.g., stable at room temperature.

The terms "stability" and "stable" as used herein in the context of a formulation comprising a protein of interest (e.g., an antibody) of the invention refer to the resistance of the protein of interest in the formulation to aggregation, degradation or fragmentation under given manufacture, preparation, transportation and storage conditions. The "stable" formulations of the invention retain biological activity under given manufacture, preparation, transportation and storage conditions. The stability of the protein of interest can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of a protein of interest of the invention in PBS.

Therapeutic formulations of the low impurity compositions, for example, low aggregate compositions, of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the protein of interest (e.g., antibody) and the particular therapeutic effect to be achieved, and (b) the limitations inherent in the art of compounding such a protein of interest for the treatment of sensitivity in individuals.

Therapeutic compositions of the low impurity compositions, for example, low aggregate compositions, of the invention can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. By way of example, in certain embodiments, the proteins of interest (including fragments of the protein of interest) are formulated for intravenous administration. In certain other embodiments, the proteins of interest (e.g., antibodies), including fragments of the proteins of interest (e.g., antibody fragments) are formulated for local delivery to the cardiovascular system, for example, via catheter, stent, wire, intramyocardial delivery, intrapericardial delivery, or intraendocardial delivery.

Formulations of the low impurity compositions, for example, low aggregate compositions, of the invention which are suitable for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required (U.S. Pat. Nos. 7,378,110; 7,258,873; 7,135,180; 7,923,029; and US Publication No. 20040042972).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the low impurity compositions, for example, low aggregate compositions, of the invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In certain embodiments, the proteins of interest (e.g., antibodies) of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant Protein A receptor (Briscoe et al. (1995) *Am. J. Physiol.* 1233:134), different species of which may comprise the formulations of the invention, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the proteins of interest (e.g., antibodies) of the invention may be delivered locally to the brain to mitigate the risk that the blood brain barrier slows effective delivery.

In certain embodiments, the low impurity compositions, for example, low aggregate compositions, of the invention may be administered with medical devices known in the art. For example, in certain embodiments a protein of interest (e.g., antibody) or a fragment of protein of interest (e.g., antibody fragment) is administered locally via a catheter, stent, wire, or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multichamber compartments; and U.S. Pat. No. 4,475,196, which discloses an osmotic drug delivery system. Many other such implants, delivery systems, and modules are known to those skilled in the art.

The efficient dosages and the dosage regimens for the reduced level of at least one impurity compositions of the invention depend on the disease or condition to be treated and can be determined by the persons skilled in the art. One of ordinary skill in the art would be able to determine such amounts based on such factors as the subject's size, the severity of the subject's symptoms, and the particular composition or route of administration selected.

Alternative Formulations Containing the Low Impurity Compositions of the Invention Alternative Aqueous Formulations The invention also provides a low impurity composition, for example a low aggregate composition, formulated as an aqueous formulation comprising a protein of interest and water, as described in U.S. Pat. No. 8,420,081, the contents of which are hereby incorporated by reference. In these aqueous formulations, the protein of interest is stable without the need for additional agents. This aqueous formulation has a number of advantages over conventional formulations in the art, including stability of the protein of interest in water without the requirement for additional excipients, increased concentrations of protein of interest without the need for additional excipients to maintain solubility of the protein of interest, and low osmolality. These also have advantageous storage properties, as the proteins of interest in the formulation remain stable during storage, e.g., stored as a liquid form for more than 3 months at 7° C. or freeze/thaw conditions, even at high protein of interest concentrations and repeated freeze/thaw processing steps. In one embodiment, formulations described herein include high concentrations of proteins of interest such that the aqueous formulation does not show significant opalescence, aggregation, or precipitation.

In one embodiment, an aqueous low impurity composition comprising a protein of interest, e.g., an antibody, an anti-TNFα antibody or antigen biding portion thereof, and water is provided, wherein the formulation has certain characteristics, such as, but not limited to, low conductivity, e.g., a conductivity of less than about 2.5 mS/cm, a protein of interest concentration of at least about 10μg/mL, an osmolality of no more than about 30 mOsmol/kg, and/or the protein of interest has a molecular weight (Mw) greater than about 47 kDa. In one embodiment, the formulation has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized, or spray-dried.

In one embodiment, the formulation has a low conductivity, including, for example, a conductivity of less than about 2.5 mS/cm, a conductivity of less than about 2 mS/cm, a conductivity of less than about 1.5 mS/cm, a conductivity of less than about 1 mS/cm, or a conductivity of less than about 0.5 mS/cm.

In another embodiment, low impurity compositions included in the formulation have a given concentration, including, for example, a concentration of at least about 1 mg/mL, at least about 10 mg/mL, at least about 50 mg/mL, at least about 100 mg/mL, at least about 150 mg/mL, at least about 200 mg/mL, or greater than about 200 mg/mL. In another embodiment, the formulation of the invention has an osmolality of no more than about 15 mOsmol/kg.

The aqueous formulations described herein do not rely on standard excipients, e.g., a tonicity modifier, a stabilizing agent, a surfactant, an anti-oxidant, a cryoprotectant, a bulking agent, a lyroprotectant, a basic component, and an acidic component. In other embodiments of the invention, the formulation contains water, one or more proteins of interest, and no ionic excipients (e.g., salts, free amino acids).

In certain embodiments, the aqueous formulation as described herein comprise a low impurity composition comprising a protein of interest concentration of at least 50 mg/mL and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg, and also have a high protein of interest concentration, e.g., the concentration of the protein of interest is at least 100 mg/mL, and may be as much as 200 mg/mL or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation as described herein is not limited by the protein of interest size and the formulation may include any size range of proteins. Included within the scope of the invention is an aqueous formulation comprising at least 40 mg/mL and as much as 200 mg/mL or more of a protein of interest, for example, 40 mg/mL, 65 mg/mL, 130 mg/mL, or 195 mg/ml, which may range in size from 5 kDa to 150 kDa or more. In one embodiment, the protein of interest in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation as described herein may be characterized by the hydrodynamic diameter ($D_h$) of the proteins of interest in solution. The hydrodynamic diameter of the protein of interest in solution may be measured using dynamic light scattering (DLS), which is an established analytical method for determining the $D_h$ of proteins. Typical values for monoclonal antibodies, e.g., IgG, are about 10 nm. Low-ionic formulations may be characterized in that the $D_h$ of the proteins of interest are notably lower than protein of interest formulations comprising ionic excipients. It has been discovered that the $D_h$ values of antibodies in aqueous formulations made using the disfiltration/ultrafilteration (DF/UF) process, as described in U.S. Pat. No. 8,420,081, using pure water as an exchange medium, are notably lower than the $D_h$ of antibodies in conventional formulations independent of protein concentration. In one embodiment, antibodies in the aqueous formulation as described herein have a $D_h$ of less than 4 nm, or less than 3 nm.

In one embodiment, the $D_h$ of the protein of interest in the aqueous formulation is smaller relative to the $D_h$ of the same protein of interest in a buffered solution, irrespective of protein of interest concentration. Thus, in certain embodiments, a protein of interest in an aqueous formulation made in accordance with the methods described herein, will have a $D_h$ which is at least 25% less than the $D_h$ of the protein of interest in a buffered solution at the same given concentration. Examples of buffered solutions include, but are not limited to phosphate buffered saline (PBS). In certain embodiments, proteins of interest in the aqueous formulation of the invention have a $D_h$ that is at least 50% less than the $D_h$ of the protein of interest in PBS in at the given concentration; at least 60% less than the $D_h$ of the protein of interest in PBS at the given concentration; at least 70% less than the $D_h$ of the protein of interest in PBS at the given concentration; or more than 70% less than the $D_h$ of the protein of interest in PBS at the given concentration. Ranges intermediate to the above recited percentages are also intended to be part of this invention, e.g., about 55%, 56%, 57%, 64%, 68%, and so forth. In addition, ranges of values using a combination of any of the above recited values as upper and/or lower limits are intended to be included, e.g., about 50% to about 80%.

In one aspect, the aqueous formulation includes the protein of interest at a dosage of about 0.01 mg/kg-10 mg/kg. In another aspect, the dosages of the protein of interest include approximately 1 mg/kg administered every other week, or approximately 0.3 mg/kg administered weekly. A skilled practitioner can ascertain the proper dosage and regime for administering to a subject.

Alternative Solid Unit Formulations

The invention also provides a low impurity composition of the invention formulated as a stable composition of a protein of interest, e.g., an antibody, or antigen binding portion thereof, and a stabilizer, referred to herein as solid units, as described in Ser. No. 61/893,123, the contents of which are hereby incorporated by reference herein.

Specifically, it has been discovered that despite having a high proportion of sugar, the solid units comprising the low impurity compositions of the invention maintain structural rigidity and resist changes in shape and/or volume when stored under ambient conditions, e.g., room temperature and humidity, for extended periods of time (e.g., the solid units comprising the low impurity compositions of the invention do not require storage in a sealed container) and maintain long-term physical and chemical stability of the protein of interest without significant degradation and/or aggregate formation. Moreover, despite having a high proportion of sugar, the solid units comprising the low impurity compositions of the invention remain free-flowing when stored under ambient conditions, e.g., room temperature and humidity, for extended periods of time, and yet are easily dissolved in an aqueous solvent, e.g., water (e.g., the solid units require minimal mixing when contacted with a solvent for reconstitution). Furthermore, the solid units comprising the low impurity compositions of the invention may be prepared directly in a device for patient use. These properties, when compared to existing techniques which require a vial containing a lyophilized protein of interest provided as a cake (which may not stabilize a protein of interest for extended periods of time), a separate vial for a diluent, one or more sterile syringes, and several manipulation steps, thus provides alternative approaches for reconstitution since the solid units comprising the low impurity compositions of the invention may be provided, e.g., in a dual chambered cartridge, to make reconstitution invisible during patient delivery. Furthermore, the solid units comprising the low impurity compositions of the invention are versatile in that they can be readily and easily adapted for numerous modes of administration, such as parenteral and oral administration.

As used herein, the term "solid unit," refers to a composition which is suitable for pharmaceutical administration and comprises a protein of interest, e.g., an antibody or peptide, and a stabilizer, e.g., a sugar. The solid unit comprising the low impurity compositions of the invention has a structural rigidity and resistance to changes in shape and/or volume. In one embodiment, the solid unit comprising the low impurity compositions of the invention is obtained by freeze-drying a pharmaceutical formulation of a therapeutic protein of interest. The solid unit comprising the low impurity compositions of the invention may be any shape, e.g., geometric shape, including, but not limited to, a sphere, a cube, a pyramid, a hemisphere, a cylinder, a teardrop, and so forth, including irregularly shaped units. In one embodiment, the solid unit has a volume ranging from about 1 □1 to about 20 □1. In another embodiment, the solid unit is not obtained using spray drying techniques, e.g., the solid unit is not a powder or granule.

As used herein, the phrase "a plurality of solid units" refers to a collection or population of solid units comprising the low impurity compositions of the invention, wherein the collection comprises two or more solid units having a substantially uniform shape, e.g., sphere, and/or volume distribution. A substantially uniform size distribution is intended to mean that the individual shapes and/or volumes of the solid units comprising the low impurity compositions of the invention are substantially similar and not greater than a 10% standard deviation in volume. For example, a plurality of solid units which are spherical in shape would include a collection of solid units having no greater than 10% standard deviation from an average volume of the spheres. In one embodiment, the plurality of solid units is free-flowing.

Kits and Articles of Manufacture Comprising the Low Impurity Compositions of the Invention Also within the scope of the present invention are kits comprising the low impurity compositions of the invention and instructions for use. The term "kit" as used herein refers to a packaged product comprising components with which to administer the protein of interest (e.g., antibody, or antigen-binding portion thereof)), of the invention for treatment of a disease or disorder. The kit may comprise a box or container that holds the components of the kit. The box or container is affixed with a label or a Food and Drug Administration approved protocol. The box or container holds components of the invention which may be contained within plastic, polyethylene, polypropylene, ethylene, or propylene vessels. The vessels can be capped-tubes or bottles. The kit can also include instructions for administering a protein of interest (e.g., an antibody) of the invention.

The kit can further contain one more additional reagents, such as an immunosuppressive reagent, a cytotoxic agent or a radiotoxic agent or one or more additional proteins of interest of the invention (e.g., an antibody having a complementary activity which binds to an epitope in the TNFα antigen distinct from a first anti-TNFα antibody). Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation or lyophilized formulation of a protein of interest (e.g., an antibody or antibody fragment thereof) of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. No. 6,792,743, U.S. Pat. No. 5,607,400, U.S. Pat. No. 5,893,842, U.S. Pat. No. 7,081,107, U.S. Pat. No. 7,041,087, U.S. Pat. No. 5,989,227, U.S. Pat. No. 6,807,797, U.S. Pat. No. 6,142,976, U.S. Pat. No. 5,899,889, U.S. Pat. No. 7,699,811, U.S. Pat. No. 7,540,382, U.S. Pat. No. 7,998,120, U.S. Pat. No. 7,645,267, and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising proteins of interest (e.g., antibodies) of the invention are also provided that are useful for various purposes, e.g., research and diagnostic including for purification or immunoprecipitation of protein of interest from cells, detection of the protein of interest in vitro or in vivo. For isolation and purification of a protein of interest, the kit may contain an antibody coupled to beads (e.g., sepharose beads). Kits may be provided which contain the antibodies for detection and quantitation of a protein of interest in vitro, e.g., in an ELISA or a Western blot. As with the article of manufacture, the kit comprises a container and a label or package insert on or associated with the container. The container holds a composition comprising at least one protein of interest (e.g., antibody) of the invention. Additional containers may be included that contain, e.g., diluents and buffers, control proteins of interest (e.g., antibodies). The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising a protein of interest (e.g., an antibody) that is suitable for parenteral administration. In another embodiment, the unit dosage form is provided as a sterile lyophilized powder comprising a protein of interest (e.g., an antibody) that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within said packaging material, wherein said pharmaceutical agent comprises a liquid formulation containing a protein of interest (e.g., an antibody). The packaging material includes instruction means which indicate how that said protein of interest (e.g., antibody) can be used to prevent, treat and/or manage one or more symptoms associated with a disease or disorder.

The present invention is further illustrated by the following examples which should not be construed as limiting in any way. The contents of all cited references, including literature references, issued patents, and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference: U.S. Provisional Patent Application 61/893,123, entitled "STABLE SOLID PROTEIN COMPOSITIONS AND METHODS OF MAKING SAME", filed on Oct. 18, 2013; U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013; U.S. Provisional Patent Application 61/892,710, entitled "MUTATED ANTI-TNFa ANTIBODIES AND METHODS OF THEIR USE", filed on Oct. 18, 2013; U.S. Provisional Patent Application 61/893,068, entitled "LOW ACIDIC SPECIES COMPOSITIONS AND METHODS FOR PRODUCING THE SAME", filed on Oct. 18, 2013; and U.S. Provisional Patent Application 61/893,088, entitled "MODULATED LYSINE VARIANT SPECIES AND METHODS FOR PRODUCING AND USING THE SAME", filed on Oct. 18, 2013.

EXAMPLES

General Materials and Methods

Except where noted, the materials and methods described in connection with the instant example were also employed in Examples 1-3, below.

Chromatography Method

Pre-packed media columns were used in the following experiments, except where specified. The column was equilibrated in a buffer system with appropriate pH and conductivity. The column load was prepared from Protein A affinity chromatography eluates or concentrated CEX chromatography elutes by buffer exchange (if the eluates were with different buffer components from the mixed mode target buffer system) or addition of the stock solutions and/or water to obtain the target pH and conductivity as specified (if the eluates were with the same buffer components as the mixed mode target buffer system). The prepared load material was filtered and loaded on the column according to the target load amount (g protein/L media) as specified followed by washing with the equilibration buffer or buffer similar to equilibration buffer with volumes as specified. The column Flow Through/Wash were collected as fractions or as a pool. HIC column was cleaned with 20% Isopropyl Alcohol solution. 1M NaOH solution was used for column cleaning.

Buffer Preparation Method

Buffers were prepared targeting a specific salt concentration in a buffered system, and titrating to a specific pH with the conjugate acid or base. For example, an 800 mM Ammonium Sulfate ($AmSO_4$) pH 7.0 solution was made by dissolving AmSO4 salt in a 20 mM Tris-Acetate buffered solution, titrating with acetate, and subsequently bringing up to volume with water to achieve the desired $AmSO_4$ concentration. Load samples were prepared targeting a specific salt concentration by addition of concentrated salt solution in a buffered system, and titrating to a specific pH with the conjugate acid or base. For example, an 800 mM AmSO4 pH 7.0 load was made by mixing the load in a 1:1 ratio with a 1600 mM AmSO4 pH 7.0 stock buffer in a 40 mM Tris-Acetate, and subsequently titrating with Tris or acetate to achieve a final pH 7.0.

Size Exclusion Chromatography

The molecular weight distribution of collected samples were quantified according to the following methods. Size exclusion chromatography (SEC) was performed using a TSK-gel G3000SWxL, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification is based on the relative area of detected peaks.

Host Cell Protein (HCP) ELISA

HCP assay is based on process specific antigen based ELISA. Sample dilutions were applied to achieve readings within the calibration range. The limit of quantitation of the assay is 0.625 ng/mL.

UV Spectroscopy $A_{280}$

UV A280 was used to determine protein concentrations for the samples post protein A elution. The assay was performed on an Agilent UV Spectrophotometer following the method. The protein concentration was determined using Beer-Lambert's Law, $A=\epsilon l c$, where A is Absorbance, $\epsilon$ is the extinction coefficient, l is the path length, and c is the concentration. The absorbance was taken at 280 nm, the path length was 1 cm, and the extinction coefficients were 1.39 for Adalimumab, 1.38 for mAb B, and 1.43 for mAb C.

Example 1

Determining Operating Conditions Appropriate for an mAb:Media:Buffer Combination The demonstration of the current invention for a specific antibody & media is provided in this example, and consists of: 1) Choosing a salt concentration that allows product and impurities to bind at a given pH; 2) Loading a small amount of protein to the column and then performing a linear gradient elution by decreasing the salt concentration; 3) Determining salt concentration range in which the protein elutes from the HIC media.

Figure 4:
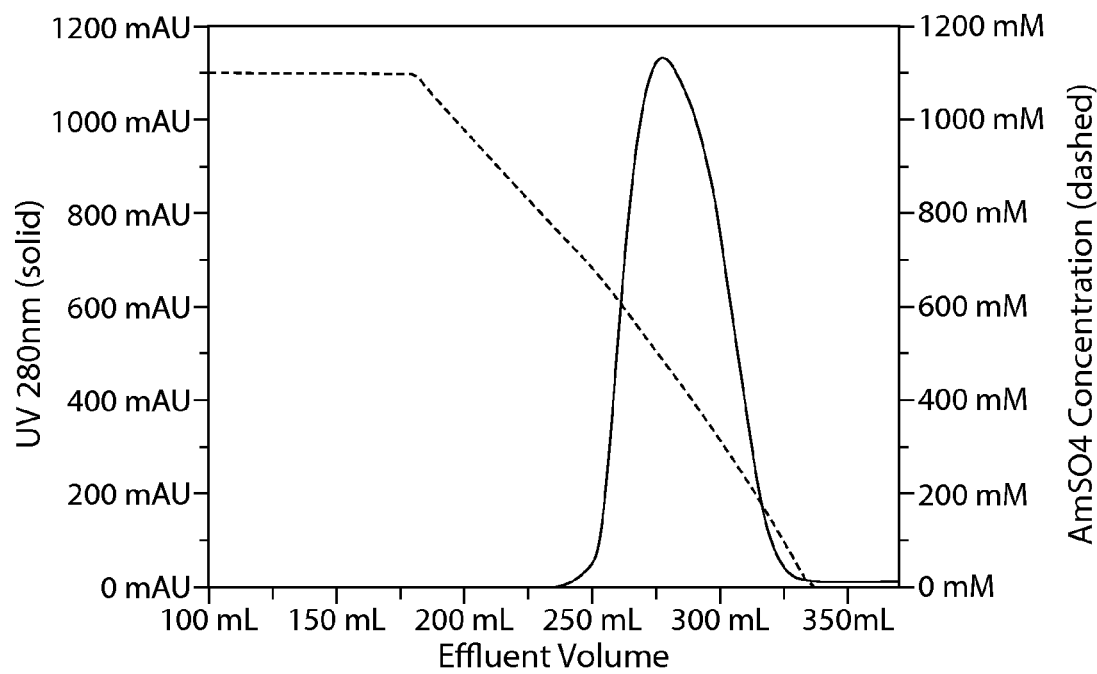

In this example, adalimumab and GE CaptoPhenyl were chosen. The column was equilibrated at 1.1 M $AmSO_4$ pH 7.0 (Tris/Acetate) for 10 CVs. Adalimumab was prepared at 1.1 M $AmSO_4$ and loaded to the column at 20 g-protein/L of resin. The column was washed with 10 CVs of the equilibration buffer. A linear gradient from 1.1M to 0M $AmSO_4$ pH 7.0 (Tris/Acetate) over 20CVs was performed. The process chromatogram is shown in FIG. 4.

This process can be repeated for any given mAb-media combination for a given buffer system. Table 1 shows the DOE parameters determined using the method described above for adlimumab in AmSO4 pH 7.0 (Tris/acetate) for 3 different HIC adsorbents.

TABLE 1

Example Experimental Design Scope
determined from LGE with different resins
Adlimumab - Ammonium Sulfate pH 7.0 (Tris/Acetate)

| Resin | Buffer Concentration Range |
|---|---|
| Tosoh Hexyl | 250-750 mM |
| GE CaptoPhenyl | 300-650 mM |
| GE Butyl FF | 800-950 mM |

In practicing the current invention, the aggregate reduction desired can be achieved by appropriate pooling of the load and wash fractions. By collecting and subsequently determining the product quality of each fraction throughout the load and wash, the accumulative aggregate reduction and accumulative yield can be calculated using the weighted averages up to a given fraction. Additionally, the instantaneous yield can be estimated by comparing the protein recovered against the total protein loaded to the column at a given fraction. Sample calculations are shown below:

Sample Calculation A: Accumulative Yield up to a given fraction $$\text{Accumulative Yield} = \frac{\text{Accumulated Protein Mass Recovered up to Fraction}}{\text{Total Mass Protein Load}}$$

Sample Calculation B: Accumulative Aggregate Reduction up to a given fraction $$\text{Accumulative Aggregate Reduction} = \ldots$$

$$\text{Load } Agg\% - \frac{\text{Accumulated Aggregate Mass Recovered up to Fraction}}{\text{Accumulated Total Protein Mass Recovered up to Fraction}}$$

Sample Calculation C: Instantaneous Yield up to a given fraction $$\text{Instantaneous Yield} = \frac{\text{Accumulated Protein Mass Recovered up to Fraction}}{\text{Total Protein Mass Loaded to Column at Fraction}}$$

The demonstration of the current invention for a specific antibody & resin is provided in this example, and consists of
1. For a given salt concentration and optionally pH and HIC media.
2. Loading the HIC media in excess of the dynamic binding capacity for the product for the given condition.
3. Washing the column with a buffer containing a similar salt concentration and optionally pH used for the equilibration and loading steps.
4. Collecting fractions throughout the loading and wash steps and subsequently determining the product quality profile (e.g. Aggregate, HCP etc.)

Figure 5:
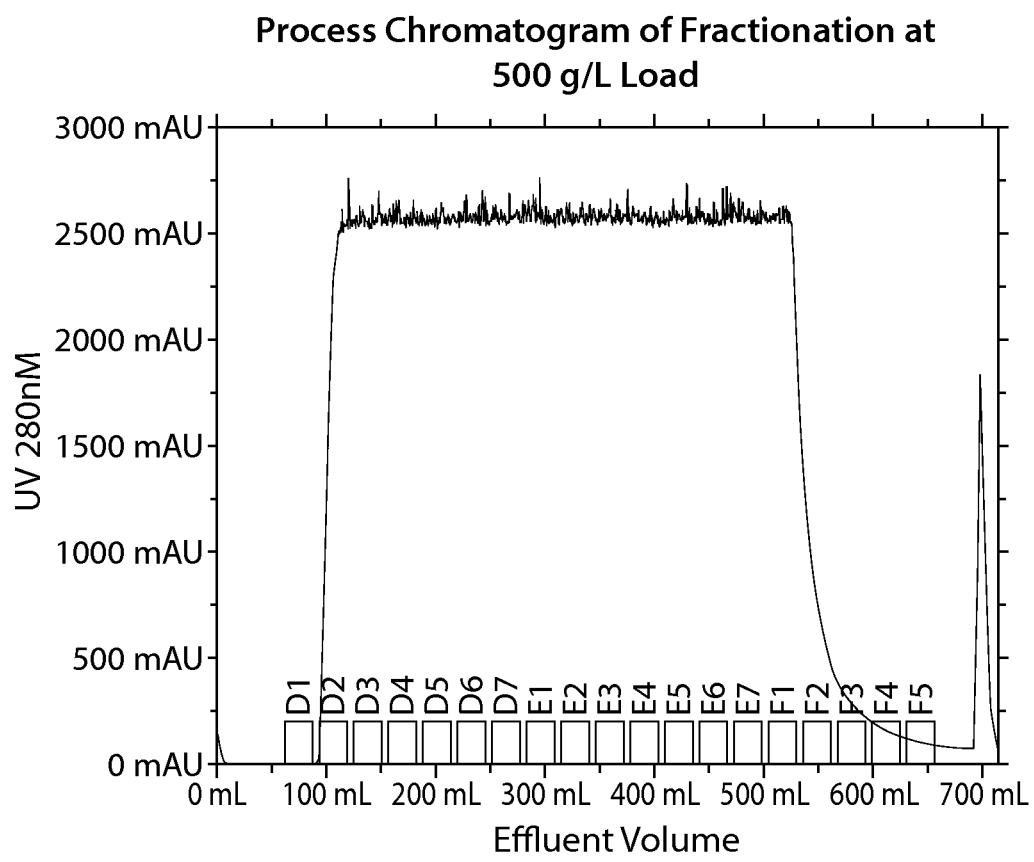

In this example, adalimumab and GE CaptoPhenyl were chosen. The experiment was performed at 400 mM sodium citrate (NaCit) pH 5.6. The column was equilibrated with 400 mM NaCit pH 5.6 for 10 CVs. Adalimumab was prepared at 400 mM NaCit pH 5.6 and loaded to the column at 500 g-protein/L-resin. The column was washed with 7 CVs of the equilibration buffer. The process chromatogram is shown in FIG. 5. Fractions were collected and analyzed for product quality and the accumulative yield and accumulative aggregate reduction calculated, shown in Table 2. From this example, it is clear to one skilled in the art to determine a run condition which delivers a targeted product quality and/or step yield.

This general approach is used to evaluate the performance for a given operating condition for any resin/mAb/buffer combination.

TABLE 2

Accumulative Yield and Aggregate Reduction from FIG. 5

| Fraction | Load | Accumulative Recovery | Accumulative ΔAgg |
|---|---|---|---|
| D1 | 8 g/L | 0% | 0.82% |
| D2 | 45 g/L | 4% | 0.77% |
| D3 | 82 g/L | 12% | 0.71% |
| D4 | 119 g/L | 19% | 0.67% |
| D5 | 156 g/L | 26% | 0.62% |
| D6 | 193 g/L | 33% | 0.56% |
| D7 | 231 g/L | 41% | 0.51% |
| E1 | 268 g/L | 48% | 0.47% |
| E2 | 305 g/L | 55% | 0.43% |
| E3 | 342 g/L | 62% | 0.40% |
| E4 | 379 g/L | 70% | 0.37% |
| E5 | 416 g/L | 77% | 0.34% |
| E6 | 454 g/L | 84% | 0.32% |
| E7 | 491 g/L | 91% | 0.29% |
| F1 | 500 g/L | 93% | 0.29% |
| F2 | WASH | 99% | 0.28% |
| F3 | WASH | 100% | 0.28% |
| F4 | WASH | 101% | 0.29% |
| F5 | WASH | 101% | 0.29% |

Example 2

Demonstration of Aggregate Reduction with HIC Resins

This data set is compiled to demonstrate the aggregate reduction achieved with six different HIC adsorbents. Each resin was evaluated with a 500 g/L load of adalimumab at a NaCit concentration near, and slightly higher than, the peak elution concentration determined from the process outlined in Example 1. Table 3 outlines the results from these experiments.

TABLE 3

Effect of HIC Resins on Aggregate Reduction of Adalimumab

| HIC Resin | NaCit, pH 5.6 | ΔAgg | Yield |
|---|---|---|---|
| Butyl | 400 mM | 1.5% | 99.8% |
|  | 450 mM | 1.2% | 85.7% |
| Hexyl | 240 mM | 1.2% | 93.9% |
|  | 300 mM | 1.1% | 100.9% |
| Phenyl | 400 mM | 1.5% | 96.5% |
|  | 450 mM | 1.2% | 90.7% |
| Octyl | 350 mM | 0.4% | 98.5% |
|  | 400 mM | 0.1% | 103.3% |
| GE Butyl FF | 550 mM | 1.2% | 88.1% |
|  | 600 mM | 1.7% | 83.0% |
| PPG | 450 mM | 0.2% | 97.5% |
|  | 600 mM | 1.0% | 38.1% |

Example 3

Demonstration of Aggregate Reduction with Other Antibodies, mAb B and mAb C

Aggregate reduction technology of the current invention has been demonstrated with multiple antibodies using HIC adsorbents. Antibodies have different hydrophobic properties, leading to interaction behavior on a HIC column that differs from one antibody to another. Therefore the impact of salt type and concentration is different for each antibody.

Table 4 and Table 5, presented below, provide the data obtained for mAb B and mAB C. The data clearly demonstrates that the aggregate reduction technology is effective for alternatives to adalimumab.

TABLE 4

Aggregate reduction for mAb B, pI~9.1

| HIC Resin | AmSO4, pH 5.0 | ΔAgg | Yield |
|---|---|---|---|
| Hexyl | 370 mM | 0.8% | 100% |
|  | 710 mM | 0.6% | 93% |
| Phenyl | 340 mM | 0.6% | 95% |
|  | 790 mM | 0.5% | 95% |
| Butyl | 840 mM | 0.6% | 99% |
|  | 1000 mM | 0.6% | 96% |

TABLE 5

Aggregate reduction for mAb C, pI~7.0

| HIC Resin | AmSO4, pH 5.0 | ΔAgg | Yield |
|---|---|---|---|
| Hexyl | 80 mM | 5.0% | 89.0% |
|  | 330 mM | 4.5% | 99.8% |
| Phenyl | 130 mM | 3.5% | 92.8% |
|  | 480 mM | 2.9% | 92.8% |
| Butyl | 690 mM | 5.2% | 93.5% |
|  | 880 mM | 5.4% | 87.9% |

Example 4

Demonstration of Aggregate Reduction with Different Salt Concentrations—Adalimumab Ion concentration is a key variable in the performance of hydrophobic interaction chromatography. For every combination of antibody/resin/pH there is a range of ion concentrations that provide aggregate reduction; the strategy outlined in Example 1. can be followed to determine the aggregate reduction and the corresponding recovery for each salt concentration.

Table 6, below, shows the effect of salt concentration on aggregate reduction and step yield. In this example CaptoPhenyl and adalimumab were chosen, and evaluated at a loading of 200-500 g/L in NaCit pH 5.6 at the concentration specified. The data demonstrates that the aggregate reduction can be effectively achieved over a range of salt concentrations, and that the salt concentration and column loading can be balanced to achieve a desired step yield and final product quality

TABLE 6

Effect of Ion Concentration on Aggregate Reduction

| NaCit pH 5.6 | Load | Yield | ΔAgg |
|---|---|---|---|
| 300 mM | 200 g/L | 92% | 0.59% |
|  | 350 g/L | 96% | 0.33% |
|  | 500 g/L | 97% | 0.24% |
| 400 mM | 200 g/L | 90% | 0.76% |
|  | 350 g/L | 94% | 0.43% |
|  | 500 g/L | 96% | 0.35% |

TABLE 6-continued

Effect of Ion Concentration on Aggregate Reduction

| NaCit pH 5.6 | Load | Yield | ΔAgg |
|---|---|---|---|
| 500 mM | 200 g/L | 85% | 1.09% |
|  | 350 g/L | 91% | 0.97% |
|  | 500 g/L | 94% | 0.86% |

Example 5

Demonstration of Aggregate Reduction with Different Buffer Systems with Adalimumab In addition to the salt concentration, the salt anion and cation types are key variables in hydrophobic interaction chromatography. The invention has been demonstrated with ammonium sulfate, sodium sulfate, and sodium citrate. As one skilled in the art would appreciate the optimal salt concentration and optionally pH are different for each salt type and was derived by using the strategy outlined in Example 1. Table 7 shows the data of aggregate reduction and corresponding recovery for the different anion/cation types and different HIC adsorbents.

TABLE 7

Effect of Anion/Cation Type Aggregate Reduction

| Resin | Buffer System | Load | Yield | ΔAgg |
|---|---|---|---|---|
| CaptoPhenyl | 630 mM AmSO4 pH 7.0 | 300 g/L | 95% | 2.1% |
|  | 300 mM AmSO4 pH 7.0 | 300 g/L | 99% | 1.1% |
|  | 425 mM NaSO4 pH 7.0 | 300 g/L | 95% | 1.9% |
|  | 240 mM NaSO4 pH 7.0 | 300 g/L | 101% | 1.1% |
|  | 500 mM NaCit pH 5.6 | 350 g/L | 91% | 1.0% |
|  | 300 mM NaCit pH 5.6 | 350 g/L | 96% | 0.2% |
| Tosoh Hexyl | 725 mM AmSO4 pH 7.0 | 300 g/L | 94% | 1.7% |
|  | 275 mM AmSO4 pH 7.0 | 300 g/L | 103% | 0.9% |
|  | 460 mM NaSO4 pH 7.0 | 300 g/L | 97% | 0.7% |
|  | 180 mM NaSO4 pH 7.0 | 300 g/L | 101% | 0.6% |
|  | 440 mM NaCit pH 5.6 | 300 g/L | 87% | 0.5% |
|  | 150 mM NaCit pH 5.6 | 300 g/L | 97% | 0.5% |
| Butyl FF | 800 mM AmSO4 pH 7.0 | 300 g/L | 100% | 0.7% |
|  | 1000 mM AmSO4 pH 7.0 | 300 g/L | 94% | 1.6% |
|  | 750 mM NaSO4 pH 7.0 | 300 g/L | 96% | 1.8% |
|  | 700 mM NaSO4 pH 7.0 | 300 g/L | 101% | 1.7% |
|  | 700 mM NaCit pH 5.6 | 300 g/L | 98% | 1.6% |
|  | 600 mM NaCit pH 5.6 | 300 g/L | 95% | 1.5% |

Example 6

Demonstration of Aggregate Reduction with Different Loading

Furthermore, the strategy outlined in Example 1. to reduce aggregates through careful control of ion concentration, ion type, HIC adsorbent, and pH can be applied to various ranges of protein loading. Aggregate reduction for a range of protein loadings (e.g. 250-700 g/L) for CaptoPhenyl using a 400 mM NaCit pH 5.6 buffer is shown in Table 8, displaying a robust aggregate reduction across an expansive loading range.

TABLE 8

Impact of Column loading

| Load | Yield | ΔAgg | ΔAgg/LoadAgg |
|---|---|---|---|
| 250 g/L | 95% | 0.29% | 87% |
| 500 g/L | 100% | 0.25% | 77% |
| 700 g/L | 100% | 0.21% | 65% |

Example 7

Figure 6:
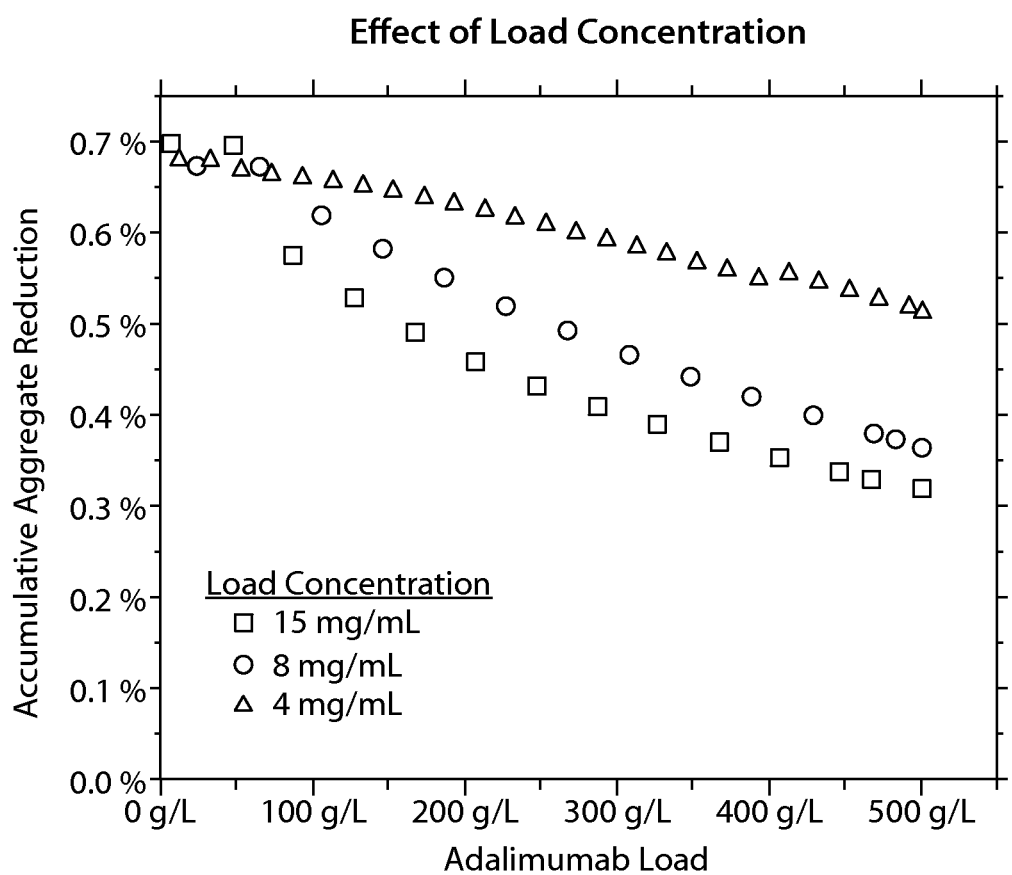

Demonstration of Aggregate Reduction with Different Load Concentration—Adalimumab In addition to the strategy outlined in Example 6. to reduce aggregates through careful control of ion concentration, ion type, and HIC adsorbent, it has been shown that the concentration of the load protein can have an effect on aggregate reduction. In this example, a feed stream was serial diluted to cover a range of load concentrations from 4 to 15 mg/mL and loaded at 500 g/L to a CaptoPhenyl column in 400 mM NaCit pH 5.6. The effect of decreasing the concentration of the load protein is shown in FIG. 6.

Example 8

Demonstration of HCP Reduction in Addition to Aggregate Reduction

HIC chromatography can also be effective in reducing host cell protein (HCP) levels. In the present invention, it has been demonstrated that HCP levels can be effectively reduced under operating conditions selected for aggregate reduction.

Table 9 shows HCP removal achieved along with aggregate reduction. The data clearly shows that other process related substances/impurities can be achieved using the current invention on the HIC adsorbents, and hence functions as an effective polishing step in the large scale purification of monoclonal antibodies.

TABLE 9

HCP Removal during HIC Chromatography

| NaCit pH 5.6 | Load | Yield | ΔAgg | HCP Load | HCP Pool |
|---|---|---|---|---|---|
| 300 mM | 200 g/L | 92% | 0.59% | 1398 ng/mg | NA |
|  | 350 g/L | 96% | 0.33% |  | 150 ng/mg |
|  | 500 g/L | 97% | 0.24% |  | 348 ng/mg |
|  | 200 g/L | 99% | 0.34% |  | 5 ng/mg |
| 400 mM | 200 g/L | 90% | 0.76% | 1599 ng/mg | 104 ng/mg |
|  | 350 g/L | 94% | 0.43% |  | 148 ng/mg |
|  | 500 g/L | 96% | 0.35% |  | 350 ng/mg |
|  | 350 g/L | 97% | 0.35% |  | 6 ng/mg |
| 500 mM | 200 g/L | 85% | 1.09% | 1528 ng/mg | 169 ng/mg |
|  | 350 g/L | 91% | 0.97% |  | 203 ng/mg |
|  | 500 g/L | 94% | 0.86% |  | 301 ng/mg |
|  | 500 g/L | 87% | 0.35% | 38 ng/mg | 11 ng/mg |

Example 9

Demonstration of Impact of Dynamic and Equilibrium Binding

Figure 10:
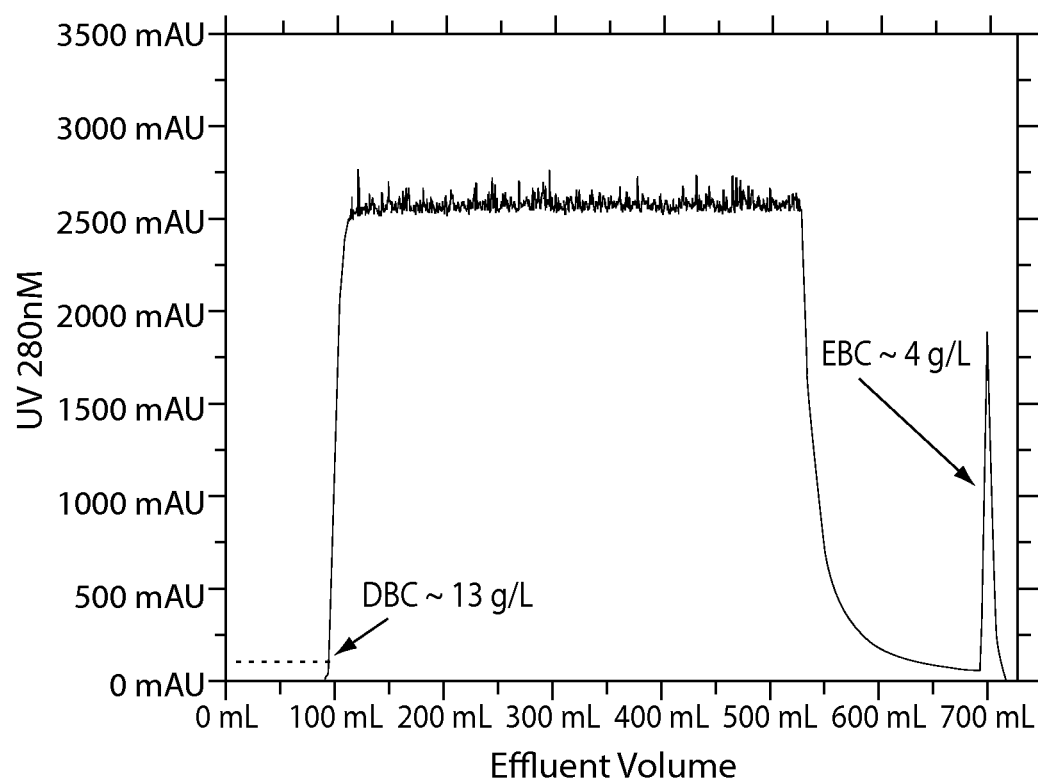
FIG. 10 depicts dynamic binding capacity (DBC), conventionally measured at 10% breakthrough, as greater than the equilibrium binding capacity (EBC), based on the data presented in FIG. 5. See Example 1.
Figure 11:
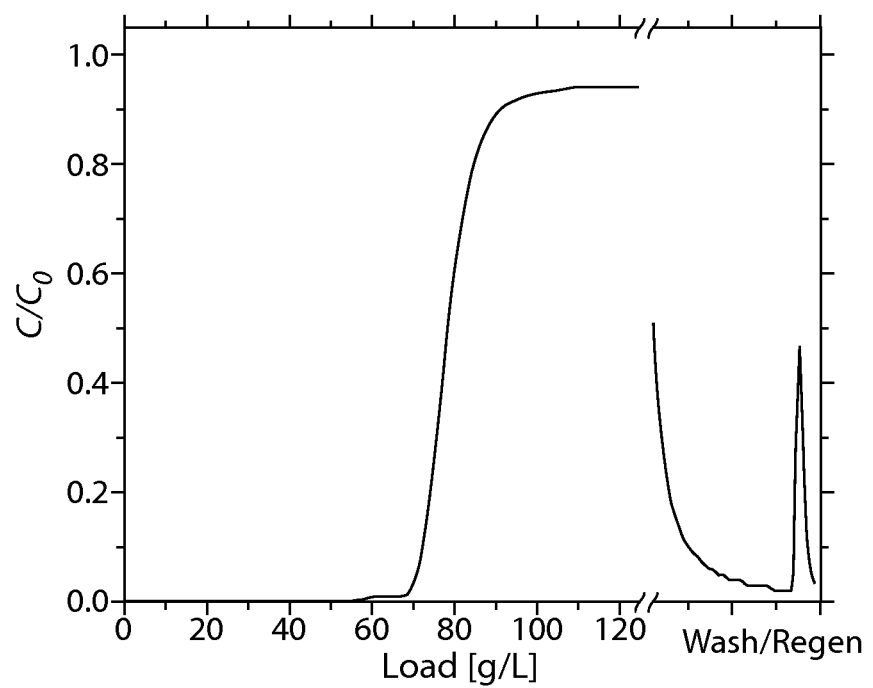
FIG. 11 depicts a dynamic binding capacity of >75 g/L. Following an isocratic wash and regeneration step, the remaining protein bound to the resin is <35 g/L.

In the HIC-based separation strategies described herein, the measured dynamic binding capacity (DBC), which is conventionally measured at 10% breakthrough, was found to be greater than the amount of protein that remained bound after washing the column (a.k.a equilibrium binding capacity, EBC) with a buffer with similar pH and salt concentration to the equilibration and load conditions. For example, but not by way of limitation, FIG. 10 shows an example of the DBC and EBC for the data presented in FIG. 5. In addition, Table 10 shows effect of salt type, concentration, and HIC resin on DBC and EBC values for Adalimumab.

TABLE 10

Comparison of DBC and EBC values for Adilmumab

| Resin | Buffer System | ΔAgg | DBC | EBC |
|---|---|---|---|---|
| CaptoPhenyl | 630 mM AmSO4 pH 7.0 | 2.1% | 27 g/L | 16 g/L |
|  | 300 mM AmSO4 pH 7.0 | 1.1% | 6 g/L | 4 g/L |
|  | 425 mM NaSO4 pH 7.0 | 1.9% | 22 g/L | 15 g/L |
|  | 240 mM NaSO4 pH 7.0 | 1.1% | 6 g/L | 4 g/L |
| Butyl FF | 1000 mM AmSO4 pH 7.0 | 1.6% | 17 g/L | 11 g/L |
|  | 800 mM AmSO4 pH 7.0 | 0.7% | 4 g/L | 4 g/L |
|  | 750 mM NaSO4 pH 7.0 | 1.8% | 29 g/L | 13 g/L |
|  | 700 mM NaSO4 pH 7.0 | 1.7% | 22 g/L | 11 g/L |
|  | 700 mM NaCit pH 5.6 | 1.6% | 39 g/L | 24 g/L |
|  | 600 mM NaCit pH 5.6 | 1.5% | 17 g/L | 11 g/L |

Example HIC 10

Combinations of HIC with Alternative Separation Strategies

The methods described herein for reducing aggregates using HIC can be used as an independent operation or in combination with other process steps that provide additional aggregate reduction or those providing additional complementary and supplementary purification. Data for specific separation strategies is provided in Tables 11 and 12. For example, but not by way of limitation, the following process combinations can be used:

1. Affinity→HIC
2. Affinity→AEX→HIC
3. Affinity→Mixed Mode→HIC

TABLE 11

Aggregate reduction with different source materials

| Load Source | Buffer Condition | Load | Yield | ΔAgg | HCP LRF (log reduction fraction) |
|---|---|---|---|---|---|
| ProteinA Eluate | 400 mM NaCit pH 5.6 | 500 g/L | 96% | 1.49% | NA |
|  | 450 mM NaCit pH 5.6 | 500 g/L | 91% | 1.22% | NA |
| ProteinA/ AEX FTW | 300 mM NaCit pH 5.6 | 200 g/L | 92% | 0.59% | 1.0 |
|  | 400 mM NaCit pH 5.6 | 350 g/L | 94% | 0.43% | 1.0 |
|  | 500 mM NaCit pH 5.6 | 500 g/L | 94% | 0.86% | 0.7 |
| ProteinA/ Mixed Mode FTW | 300 mM NaCit pH 5.6 | 200 g/L | 99% | 0.34% | 0.8 |
|  | 400 mM NaCit pH 5.6 | 350 g/L | 97% | 0.35% | 0.8 |
|  | 500 mM NaCit pH 5.6 | 500 g/L | 87% | 0.35% | 0.5 |

TABLE 12

Complete Process Train with Protein A Capture - Aggregate, HMW and HCP reduction

| Process | Yield (%) | % HMW reduction | HCP LRF |
|---|---|---|---|
| Clarified Harvest | 97.00% | n/a | n/a |
| Prt-A Eluate Pool | 89.60% | n/a | 1.87 |
| Viral Inactivated Filtrate | 99.70% | 0.07 | 0.39 |
| MM FT pool | 91.90% | 0.83 | 1.63 |
| HIC FT-pool | 98.50% | 0.23 | 0.46 |
| VF(FT) Filtrate | 96.10% | No reduction | 0.1 |
| BDS (FT) | 103.80% | No reduction | 0.13 |

Example 11

Hybrid HIC Binding Mechanism

By estimating the partitioning coefficient $K_p$, it can be demonstrated that certain strategies described in the instant application do not fall under the category of "Weak-Partitioning (WP)" or "Flow-Through Overload (FT)" modes as those are described in the art, e.g., US2007/0060741. For example, FIGS. 13A-13B depict the results of experiments wherein aliquots of resin are incubated with a load covering a range of protein concentrations at room temperature for 3 hours, after which the protein solution is then removed, and replaced with equilibration buffer (Wash simulation) and incubated at room temperature for 3 hours (repeated, Wash II). After each incubation, the concentration of the protein solution is measured and used to calculated the amount of protein ((A) monomer D2E7, a.k.a. Adalimumab, and (B) aggregate D2E7) bound to the resin (g protein/L resin) and plotted against the concentration of the protein solution at the end of the incubation (e.g. equilibrium). FIGS. 14A-14B depict the results outlined in FIGS. 13A-13B, highlighting the fact that at initial equilibrium a significant amount of monomer/aggregate is bound to the resin. However, after the protein solution is replaced with equilibration buffer (see arrow), the monomer de-sorbs from the resin and back into solution, whereas the aggregate remains bound.

FIGS. 15A-15B depict a determination of the binding monomer and aggregate D2E7 (based on data provided in FIGS. 13A-13B) by fitting the experimental equilibrium binding data to the Langmuir Isotherm using the equation: $q = (q_{max} \times C_{equil})/(K_d + C_{equil})$; where q=amount of protein bound to resin [=] g/L-resin; $q_{max}$=maximum amount of protein bound to resin [=] g/L-resin; $C_{equil}$=solution concentration of protein [=] g/L-soln; and $K_d$=equilibrium dissociation constant.

By fitting the experimental data, the $q_{max}$ and $K_d$ for the monomer and the aggregates can be calculated.

| Species | $Q_{max}$[mg/mL] | $K_d$[mg/mL] |
|---|---|---|
| Monomer | 41.9 | 0.47 |
| Aggregate | 6.0 | 0.01 |

Significantly, $q_{max}$ for both monomer/aggregate and the $K_d$ values (i.e. strength of binding) are similar to those of strong hydrophobic interactions, therefore it is not expected for this interaction to be "reversible." In addition, by calculating $K_p$ where:

| Species | $Q_{max}$ [mg/mL] | $K_d$ [mg/mL] | $K_p \equiv \frac{Q}{C} \cong \frac{Q_{max}}{K_d}$ |
|---|---|---|---|
| Monomer | 41.9 | 0.47 | 90 |
| Aggregate | 6.0 | 0.01 | 600 | it is apparent that the instant technique does not fall within the category of flow-through (where $K_p \leq 1$) or weak portioning (where $K_p$=1-10), but rather fall within the category of bind-elute (where $K_p \geq 10$).

Example 12

Determination of Binding Capacity at Saturation

The following protocol exemplifies the determination of (i) apparent binding capacity, i.e., the binding capacity at saturation (when outlet protein concentration equals inlet protein concentration) under flow conditions and (ii) the actual binding capacity, i.e., the amount of protein that remains bound after an isocratic wash.

A column packed with resin containing a hydrophobic interaction ligand was equilibrated with a buffer at a given salt concentration and pH. A protein load in the same buffer condition as the equilibration solution was loaded to the column until the protein breaks through the column, and the protein concentration at the effluent of the column was equal to the protein concentration at the inlet of the column (i.e., saturated). The column was then washed with the equilibration solution until the protein concentration at the effluent was effectively zero. The remaining protein bound to the column was then eluted with a buffer condition that will cause the protein to desorb from the resin.

Figure 12A:
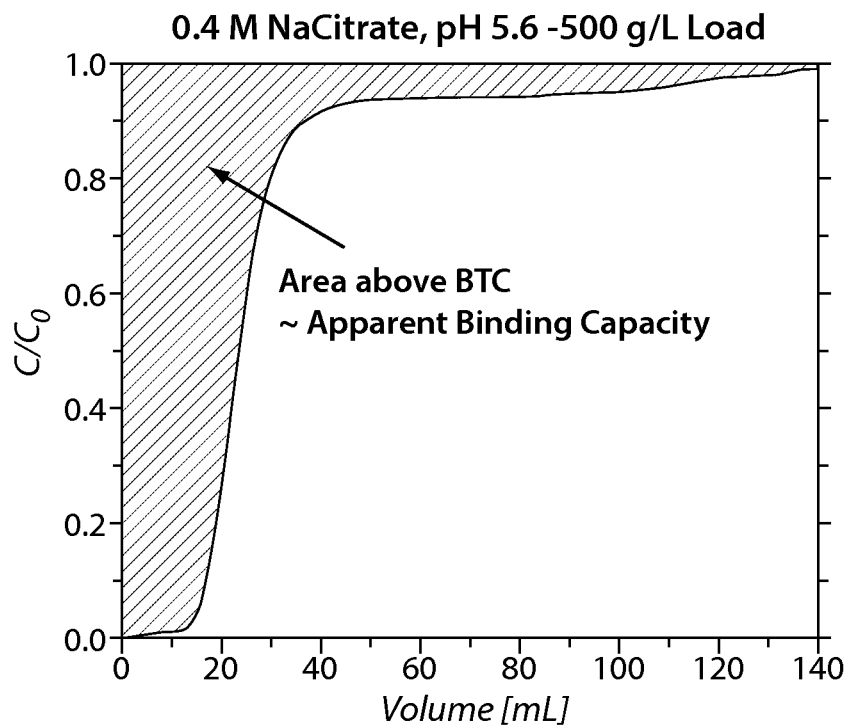
FIGS. 12A-12B depicts determination of Apparent Binding Capacity (FIG. 12A), and Actual Binding Capacity (FIG. 12B). See Example 12.
Figure 12B:
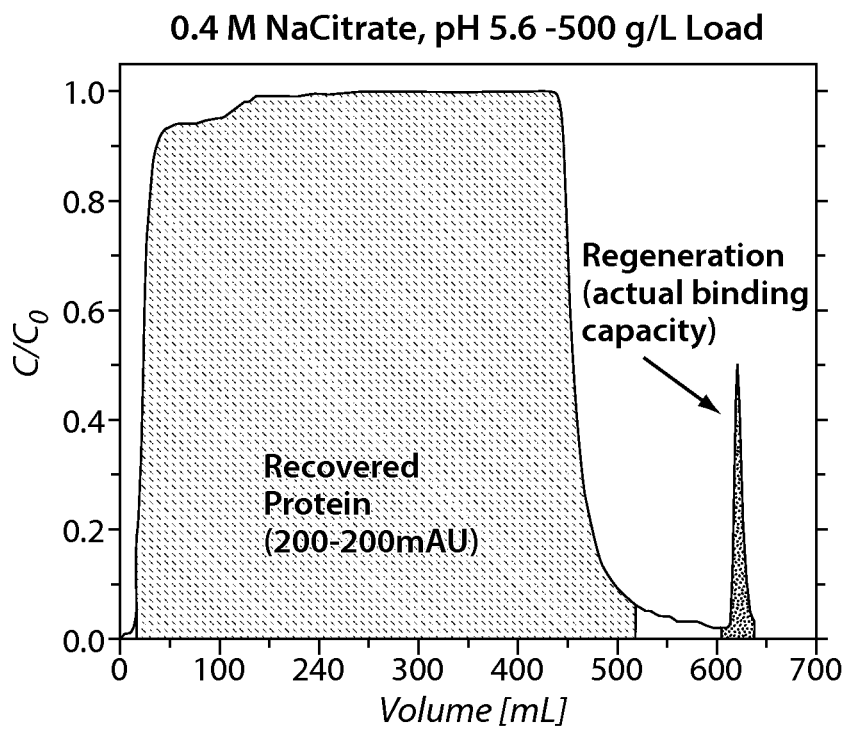

Taking into account the void volume of the column and chromatography system, one can calculate the amount of protein bound to the column at the saturation point by integrating the area above the breakthrough curve at the effluent of the column (FIGS. 12A-12B). After the isocratic wash, one can calculate the protein that remained bound to the resin by integrating the area under the curve of the elution peak.

The differences between these two values is the 'reversible' binding capacity, which is significant when compared to the binding capacity observed at the saturation point (e.g., "apparent binding capacity"). This difference is also a function of the salt concentration, which is shown in FIG. 16. FIG. 16 is a comparison of apparent and actual bound protein under flow conditions. Binding of the antibody during loading is significant (>10 g/l). The majority (>65%) of the antibody monomer bound during load desorbs during the isocratic wash (i.e., reversibly bound). The mass balance of the impurity demonstrates irreversible binding.

Example 13

Determination of Binding Capacity at Saturation

A column was conditioned and loaded, as described in Example 12, at different inlet protein concentrations. In these experiments, the flow-through fractionated to determine the product quality at different times during the loading and breakthrough. Using the protein mass and product quality for each of the fractions, the accumulative impurity (e.g., aggregate) breakthrough can be calculated using the weighted average:

Accumulative % Aggregates =

$$\frac{(\text{Sum of total aggregate mass up to fraction}_i)}{(\text{Sum of total protein mass up to fraction}_i)}$$

Figure 8A:
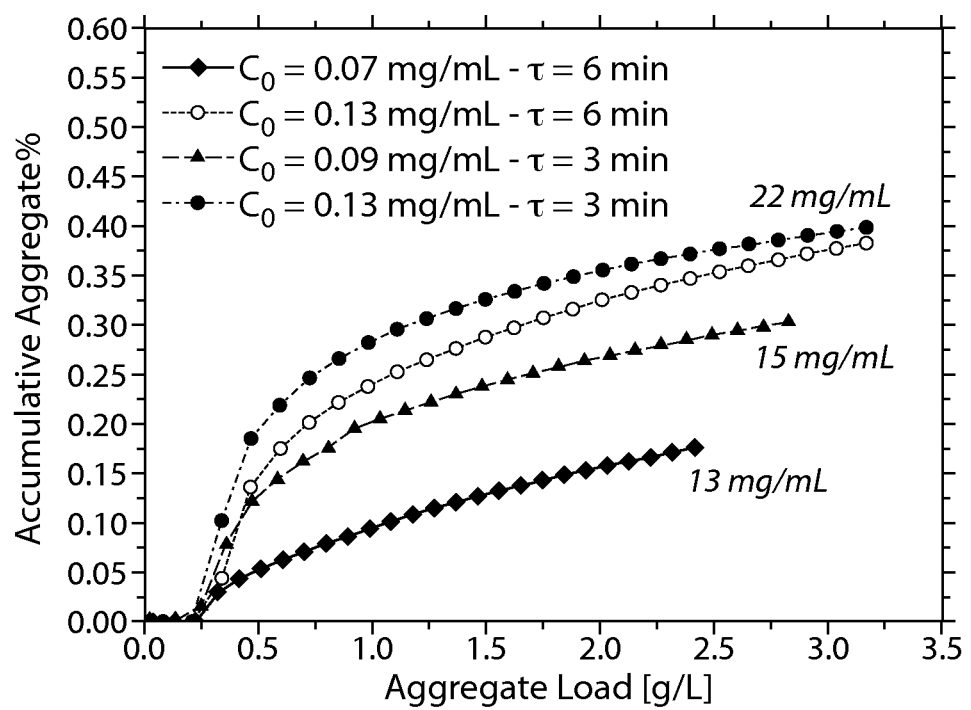
Figure 8B:
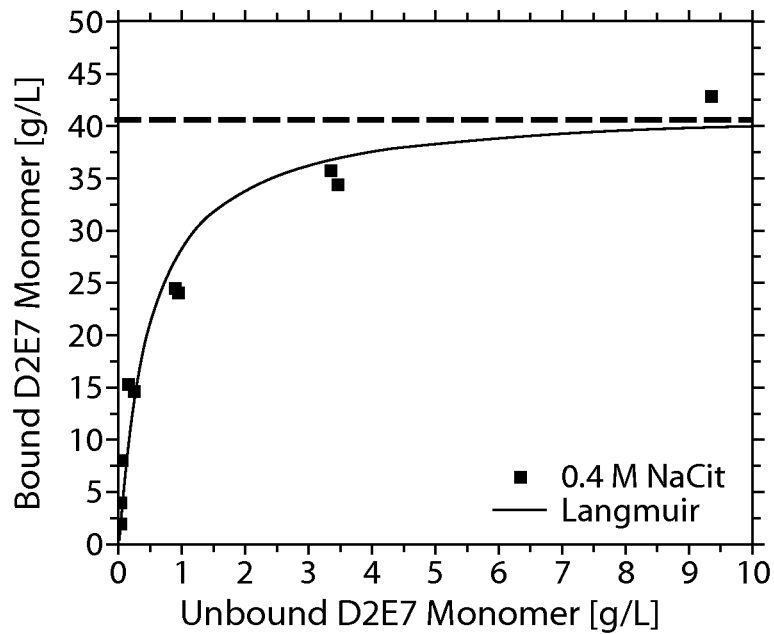
Figure 8C:
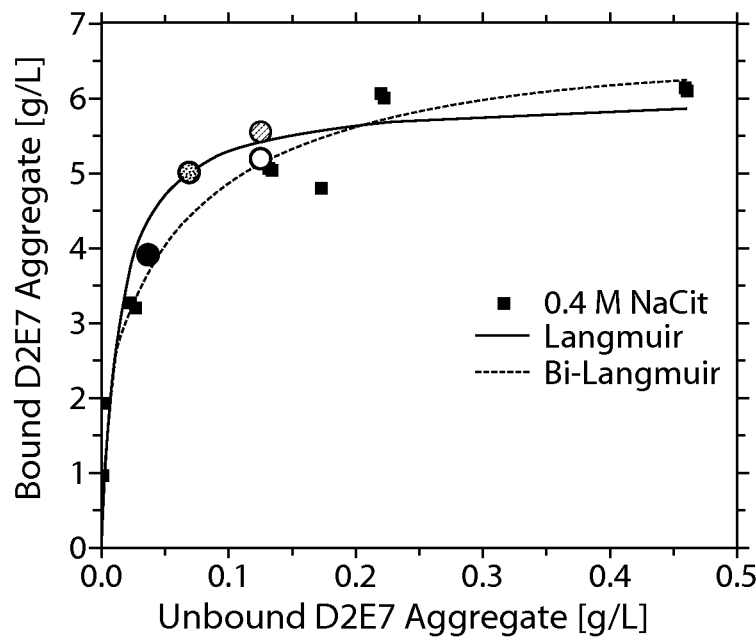

This calculation can be plotted for each successive fraction (FIG. 8A) and used to compare different loading conditions. The Equilibrium Binding Isotherms for both the monomer and aggregate show that for all of the loading conditions (FIGS. 8B-8C), the monomer was in the non-linear part of its binding isotherm (e.g., equilibrium binding capacity is independent of monomer concentration), and the aggregate was in or near the linear part of its binding isotherm (e.g., equilibrium binding capacity is dependent on aggregate concentration). The clearance of the aggregate improves by decreasing the overall load protein concentration, even though this results in the resin having a lower binding capacity for the aggregate.

Figure 7:
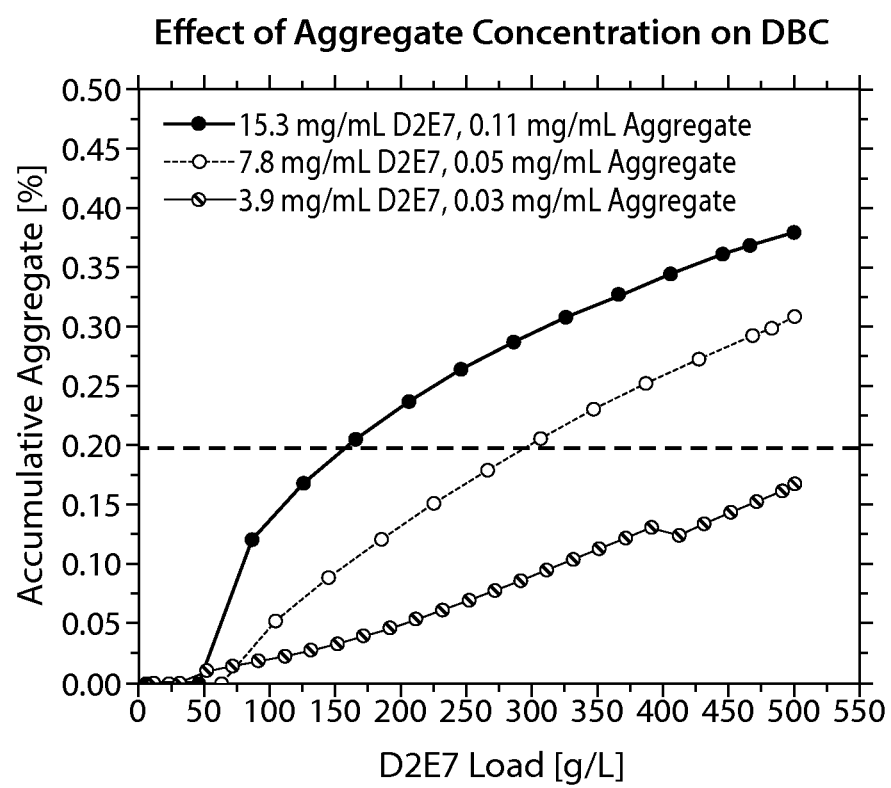

In FIG. 7, material from a single source was serially diluted to three different protein concentrations and subsequently loaded to a column to 500 g/L. This data clearly demonstrates that diluting the load material resulted in a better aggregate clearance, even though the same amount of impurity was loaded in each case. This is non-intuitive, especially when considering that diluting the load protein concentration results in a lower overall binding capacity for the impurity as the impurity is in the linear range of the equilibrium binding isotherm and therefore the binding capacity decreases linearly with concentration.

Figure 9:
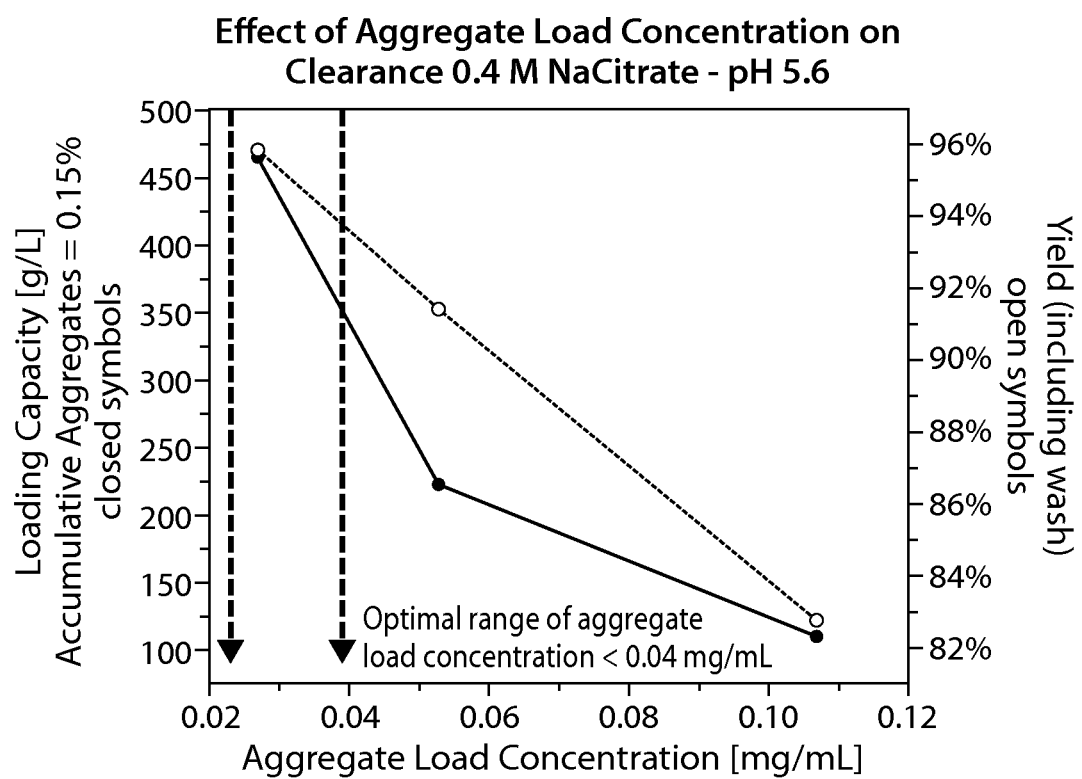
FIG. 9 depicts the modulation of the recovery-yield for a given target impurity clearance by diluting the load material to a specific range. See Example 13.

FIG. 9 is a re-plot of the same data as in FIG. 7 to demonstrate that, for a given target impurity clearance, the recovery-yield can be modulated by diluting the load material to a specific range.

---

What is claimed is:

1. A method for producing a preparation comprising a protein of interest and having a reduced level of at least one impurity, said method comprising:
   (a) contacting a sample comprising the protein of interest and at least one impurity, to a hydrophobic interaction chromatography (HIC) media, in the presence of a load buffer such that (i) a portion of the protein of interest binds to the HIC media at a Kp of greater than 20 and (ii) a substantial portion of the at least one impurity binds to the HIC media;
   (b) collecting a flow through fraction comprising the protein of interest unbound to the HIC media;
   (c) washing the HIC media with a wash buffer such that a substantial portion of the protein of interest bound to the HIC media is released from the media, wherein the salt concentration and/or the pH of the wash buffer are within 20% of the salt concentration and/or pH of the load buffer; and
   (d) collecting a wash fraction comprising the protein of interest released from the HIC media,
   wherein each of the flow through and wash fractions comprise the protein of interest and have a reduced level of the at least one impurity.

2. The method of claim 1, wherein the protein of interest is an antibody or antigen-binding fragment thereof, a soluble protein, a membrane protein, a structural protein, a ribosomal protein, an enzyme, a zymogen, an antibody molecule, a humanized antibody or antigen-binding portion thereof, a human antibody or antigen-binding portion thereof, a chimeric antibody or antigen-binding portion thereof, a multivalent antibody, a cell surface receptor protein, a transcription regulatory protein, a translation regulatory protein, a chromatin protein, a hormone, a cell cycle regulatory protein, a 0 protein, a neuroactive peptide, an immunoregulatory protein, a blood component protein, an ion gate protein, a heat shock protein, an antibiotic resistance protein, a functional fragment of any of the preceding proteins, an epitope-containing fragment of any of the preceding proteins, and combinations thereof.

3. The method of claim 1, wherein the portion of the protein of interest binds to the HIC media at a Kp of greater than 50.

4. The method of claim 1, wherein the portion of the protein of interest binds to the HIC media at a Kp of greater than 100.

5. The method of claim 1, wherein the portion of the protein of interest binds to the HIC media at a Kp of greater than 200.

6. A method for producing a preparation comprising adalimumab and having a reduced level of at least one impurity, said method comprising:
   (a) contacting a sample comprising adalimumab and at least one impurity, to a HIC media, in the presence of a load buffer such that (i) a portion of the adalimumab in the sample binds to the HIC media at a Kp of greater than 20 and (ii) a substantial portion of the at least one impurity binds to the HIC media;
   (b) collecting a flow through fraction comprising the adalimumab unbound to the HIC media;
   (c) washing the HIC media with a wash buffer such that a substantial portion of the adalimumab bound to the HIC media is released from the media, wherein the salt concentration and/or the pH of the wash buffer are within 20% of the salt concentration and/or pH of the load buffer; and
   (d) collecting a wash fraction comprising the adalimumab released from the HIC media,
   wherein each of the flow through and wash fractions comprise adalimumab and have a reduced level of the at least one impurity.

7. The method of claim 6, wherein a substantial portion of the impurity bound to the HIC media remains bound upon washing with the wash buffer.

8. The method of claim 6, wherein the flow through and/or wash fractions are substantially free of the at least one impurity.

9. The method of claim 6, wherein the at least one impurity is an aggregate of the protein of interest.

10. The method of claim 9, wherein the aggregate of the adalimumab is selected from the group consisting of a multimer, a dimer, a trimer, a tetramer, an oligomer or other high molecular weight species.

11. The method of claim 10, wherein the aggregate of adalimumab is selected from the group consisting of multimer 1, multimer 2 and multimer 3.

12. The method of claim 6, wherein the impurity is a process-related impurity.

13. The method of claim 12, wherein the process-related impurity is selected from the group consisting of a host cell protein, a host cell nucleic acid, a media component, and a chromatographic material.

14. The method of claim 6, wherein the impurity is an acidic species (AR).

15. The method of claim 14, wherein the acidic species (AR) is selected from the group consisting of AR1, AR2, a charge variant, a structure variant, a fragmentation variant, a process-related impurity and a product-related impurity.

16. The method of claim 6, further comprising repeating steps (a)-(d) at least 1 time using the flow through fraction, wash fraction, or combination thereof having a reduced level of the at least one impurity.

17. The method of claim 6, wherein the flow through fraction and the wash fraction are combined.

18. The method of claim 6, wherein the portion of the adalimumab that binds to the HIC media is at least 20% of the adalimumab in the sample.

19. The method of claim 6, wherein the at least one impurity binds to the HIC media at a Kp of greater than 250.

20. The method of claim 6, wherein the HIC media either (i) comprises at least one hydrophobic ligand, optionally selected from the group consisting of alkyl-, aryl-ligands, and butyl, hexyl, phenyl, octyl, or polypropylene glycol ligands.

21. The method of claim 6, wherein the load buffer and/or wash buffer comprise a salt selected from the group consisting of a sulfate salt, a citrate salt, ammonium sulfate, sodium sulfate, sodium chloride, ammonium chloride, sodium bromide and a combination thereof.

22. The method of claim 6, wherein 100 g to 800 g of the sample are contacted per one liter of HIC media.

23. The method of claim 6, wherein a precursor sample comprising the adalimumab has been subjected to affinity chromatography to generate the sample.

24. The method of claim 6, wherein a precursor sample comprising the adalimumab has been subjected to ion exchange chromatography to generate the sample.

25. The method of claim 6, wherein a precursor sample comprising the adalimumab has been subjected to mixed mode chromatography to generate the sample.

26. The method of claim 6, wherein a precursor sample comprising the adalimumab has been subjected to a filtration step to generate the sample.

27. The method of claim 6, wherein the HIC media has a dynamic binding capacity of at least 2 g.

28. The method of claim 6, wherein adalimumab binds to the HIC media at a Kp of greater than 50.

29. The method of claim 6, wherein the salt concentration and/or the pH of the wash buffer are within about 15% of the salt concentration and/or pH of the load buffer.

30. The method of claim 6, wherein the salt concentration and/or the pH of the wash buffer are within about 10% of the salt concentration and/or pH of the load buffer.

31. The method of claim 6, wherein the salt concentration and/or the pH of the wash buffer are within about 5% of the salt concentration and/or pH of the load buffer.

32. The method of claim 6, wherein the salt concentration and/or the pH of the wash buffer and the salt concentration and/or pH of the load buffer are isocratic.

33. The method of claim 6, wherein the impurity is a product-related substance.

34. The method of claim 33, wherein the product-related substance is selected from the group consisting of a charge variant, an acidic variant, a basic variant, a lysine variant species, an aggregate of the protein of interest, a fragment of the protein of interest, an Fc fragment of the protein of interest, a Fab fragment of the protein of interest, a modified protein, a deamidated protein, and a glycosylated protein.

35. The method of claim 6, further comprising repeating steps (a)-(d) at least 5, 10, or 20 times using the flow through fraction, wash fraction, or combination thereof having a reduced level of the at least one impurity.

36. The method of claim 6, wherein the portion of the adalimumab that binds to the HIC media is at least 90% of the adalimumab in the sample.

37. The method of claim 6, wherein the substantial portion of the adalimumab released from the HIC media upon washing with the wash buffer is at least 20% of the amount of adalimumab bound to the HIC media.

38. The method of claim 6, wherein the substantial portion of the adalimumab released from the HIC media upon washing with the wash buffer is at least 50% of the amount of adalimumab bound to the HIC media.

39. The method of claim 6, wherein the substantial portion of the adalimumab released from the HIC media upon washing with the wash buffer is at least 100% of the amount of adalimumab bound to the HIC media.

40. The method of claim 6, wherein the accumulative yield of the adalimumab in the flow through fraction and/or wash fraction is at least 35%.

41. The method of claim 6, wherein the accumulative yield of the adalimumab in the flow through fraction and/or wash fraction is at least 50%.

42. The method of claim 6, wherein the accumulative yield of the adalimumab in the flow through fraction and/or wash fraction is at least 100%.

43. The method of claim 6, wherein the accumulative yield of the adalimumab in any one flow through fraction and/or wash fraction is at least 4%.

44. The method of claim 6, wherein the accumulative yield of the adalimumab in any one flow through fraction and/or wash fraction is at least 50%.

45. The method of claim 6, wherein the accumulative yield of the adalimumab in any one flow through fraction and/or wash fraction is at least 100%.

46. The method of claim 6, wherein the substantial portion of the at least one impurity that binds to the HIC media is at least 50% of the at least one impurity in the sample.

47. The method of claim 6, wherein the substantial portion of the at least one impurity that binds to the HIC media is at least 70% of the at least one impurity in the sample.

48. The method of claim 6, wherein the substantial portion of the at least one impurity that binds to the HIC media is at least 100% of the at least one impurity in the sample.

49. The method of claim 6, wherein the reduced level of the at least one impurity of the flow through fraction and/or wash fraction is at least 50% of the at least one impurity in the sample.

50. The method of claim 6, wherein the reduced level of the at least one impurity of the flow through fraction and/or wash fraction is at least 70% of the at least one impurity in the sample.

51. The method of claim 6, wherein the reduced level of the at least one impurity of the flow through fraction and/or wash fraction is at least 100% of the at least one impurity in the sample.

52. The method of claim 6, wherein the accumulative aggregate reduction of the at least one impurity in any one flow through fraction and/or wash fraction is at least 0.1%.

53. The method of claim 6, wherein the accumulative aggregate reduction of the at least one impurity in any one flow through fraction and/or wash fraction is at least 5.0%.

54. The method of claim 6, wherein the accumulative aggregate reduction of the at least one impurity in any one flow through fraction and/or wash fraction is at least 20%.

55. The method of claim 6, wherein the accumulative aggregate reduction of the at least one impurity in the flow through fraction and/or wash fraction is at least 0.1%.

56. The method of claim 6, wherein the accumulative aggregate reduction of the at least one impurity in the flow through fraction and/or wash fraction is at least 5.0%.

57. The method of claim 6, wherein the accumulative aggregate reduction of the at least one impurity in the flow through fraction and/or wash fraction is at least 20.0%.

58. The method of claim 6, wherein the level of the at least one impurity is reduced by at least 60%, 80% or 95% of the at least one impurity in the sample.

59. The method of claim 6, wherein the at least one impurity binds to the HIC media at a Kp of greater than 500.

60. The method of claim 6, wherein the at least one impurity binds to the HIC media at a Kp of greater than 1000.

61. The method of claim 6, wherein the adalimumab and the at least one impurity have a Kp ratio less than 1:10, 1:5 or 1:2.

62. The method of claim 6, wherein the $K_d$ for the binding of the adalimumab to the HIC media is at least 0.2, 0.4 or 0.6.

63. The method of claim 6, wherein the $K_d$ for the binding of the at least one impurity to the HIC media is less than or equal to 0.001.

64. The method of claim 6, wherein the $K_d$ for the binding of the at least one impurity to the HIC media is less than or equal to 0.01.

65. The method of claim 6, wherein the $K_d$ for the binding of the at least one impurity to the HIC media is less than or equal to 0.1.

66. The method of claim 6, wherein the $K_d$ for the binding of the at least one impurity to the HIC media is less than or equal to 0.2.

67. The method of claim 6, wherein the $K_d$ for the binding of the adalimumab protein of interest to the HIC media is less than 50, 25 or 5 times the $K_d$ for the binding of the at least one impurity to the HIC media.

68. The method of claim 6, wherein the adalimumab has a Qmax of at least 20, 50 or 100.

69. The method of claim 6, wherein the at least one impurity has a Qmax of at least 2, 20 or 40.

70. The method of claim 6, wherein the load buffer and/or wash buffer comprise a cation selected from the group consisting of $Ba^{2+}$, $Ca^{2+}$, $Mg^{2+}$, $Li^+$, $Cs^+$, $Na^+$, $K^+$, $Rb^+$, $NH_4^+$ and a combination thereof.

71. The method of claim 6, wherein the load buffer and/or wash buffer comprise an anion selected from the group consisting of $PO_4^{3-}$, $SO_4^{2-}$, $CH_3CO_3^-$, $Cl^-$, $Br^-$, $NO_3^-$, $ClO_4^-$, $I^-$, $SCN^-$ and a combination thereof.

72. The method of claim 6, wherein the load buffer and/or wash buffer comprise a salt having a concentration of between 50 mM and 2000 mM.

73. The method of claim 6, wherein the load buffer and/or wash buffer have a pH between about 4.0 and 8.5.

74. The method of claim 6, wherein the load buffer and/or wash buffer have a pH between 5.0 and 7.0.

75. The method of claim 6, wherein the load buffer and/or wash buf

76. The method of claim 6, wherein the load buffer and/or wash buffer have a pH of 6.5.

77. The method of claim 6, wherein the load buffer and/or wash buffer have a pH of 8.5.

78. The method of claim 6, wherein 0.2 g to 120 g of the at least one impurity is contacted per one liter of HIC media.

79. The method of claim 6, wherein the sample has a protein concentration of 2 mg/ml to 50 mg/ml.

80. The method of claim 6, wherein the sample has an adalimumab a protein of interest concentration of 2 mg/ml to 50 mg/ml.

81. The method of claim 6, wherein the concentration of the at least one impurity in the sample is 0.01 to 5.0 mg/ml.

82. The method of claim 6, further comprising subjecting the preparation comprising adalimumab a protein of interest and having a reduced level of one impurity to affinity chromatography.

83. The method of claim 23 or 82, wherein the affinity chromatography is performed using affinity chromatographic media selected from the group consisting of Protein A, G, A/G and L media.

84. The method of claim 6, further comprising subjecting the preparation comprising adalimumab a protein of interest and having a reduced level of the at least one impurity to a filtration step.

85. The method of claim 26 or 84, wherein the filtration step is selected from the group consisting of a depth filtration step, a nanofiltration step, an ultrafiltration step, and an absolute filtration step, or a combination thereof.

86. The method of claim 6, wherein the HIC media has a dynamic binding capacity of at least 50 g.

87. The method of claim 6, wherein the HIC media has a dynamic binding capacity of at least 100 g.

88. The method of claim 6, wherein adalimumab binds to the HIC media at a Kp of greater than 100.

89. The method of claim 6, wherein adalimumab binds to the HIC media at a Kp of greater than 200.

90. The method of claim 6, further comprising subjecting the preparation comprising adalimumab and having a reduced level of the at least one impurity to ion exchange chromatography.

91. The method of claim 24 or 90, wherein ion exchange chromatography is performed using ion exchange chromatography media selected from the group consisting of a cation exchange media and an anion exchange media.

92. The method of claim 6, further comprising subjecting the preparation comprising adalimumab and having a reduced level of the at least one impurity to mixed mode chromatography.

* * * * *

UNITED STATES PATENT AND TRADEMARK OFFICE
CERTIFICATE OF CORRECTION

PATENT NO.         : 8,946,395 B1                                               Page 1 of 1
APPLICATION NO.    : 14/077574
DATED              : February 3, 2015
INVENTOR(S)        : Matthew Omon Herigstad et al.

It is certified that error appears in the above-identified patent and that said Letters Patent is hereby corrected as shown below:

In the Claims:

In claim 2 (column 89, lines 2-3), delete "a 0 protein" and replace with --a G protein--;

In claim 67 (column 92, line 21), delete "adalimumab protein of interest" and replace with --adalimumab--;

In claim 75 (column 92, lines 43 & 44), delete "wherein the load buffer and/or wash buf" and replace with --wherein the load buffer and/or wash buffer have a pH of 4.0.--;

In claim 80 (column 92, line 53), delete "adalimumab a protein of interest" and replace with --adalimumab--;

In claim 82 (column 92, line 57), delete "adalimumab a protein of interest" and replace with --adalimumab--; and In claim 84 (column 92, line 67), delete "adalimumab a protein of interest" and replace with --adalimumab--.

Signed and Sealed this
Seventeenth Day of November, 2015

Michelle K. Lee
*Director of the United States Patent and Trademark Office*